US011026672B2

(12) United States Patent
Niland et al.

(10) Patent No.: US 11,026,672 B2
(45) Date of Patent: Jun. 8, 2021

(54) METHOD AND APPARATUS FOR CARDIAC PROCEDURES

(71) Applicants: Harpoon Medical, Inc., Baltimore, MD (US); University of Maryland, Baltimore, Baltimore, MD (US)

(72) Inventors: William Niland, Arnold, MD (US); Felino V. Cortez, Jr., Bowie, MD (US); James S. Gammie, Stevenson, MD (US); Michael Nicholas D'ambra, Phoenix, AZ (US); Peter Wilson, Killingworth, CT (US); Stephen Cournane, Severn, MD (US)

(73) Assignees: Harpoon Medical, Inc., Baltimore, MD (US); University of Maryland, Baltimore, Baltimore, MD (US)

( * ) Notice: Subject to any disclaimer, the term of this patent is extended or adjusted under 35 U.S.C. 154(b) by 145 days.

(21) Appl. No.: 16/012,195

(22) Filed: Jun. 19, 2018

(65) Prior Publication Data
US 2018/0360439 A1 Dec. 20, 2018

Related U.S. Application Data

(60) Provisional application No. 62/521,784, filed on Jun. 19, 2017.

(51) Int. Cl.
*A61B 17/04* (2006.01)
*A61B 17/00* (2006.01)
(Continued)

(52) U.S. Cl.
CPC .... *A61B 17/0401* (2013.01); *A61B 17/00234* (2013.01); *A61B 17/0483* (2013.01);
(Continued)

(58) Field of Classification Search
CPC .... A61F 2/2427; A61F 2/2454; A61F 2/2457; A61B 17/0401; A61B 2017/0409;
(Continued)

(56) References Cited

U.S. PATENT DOCUMENTS 3,131,957 A 5/1964 Musto
3,752,516 A 8/1973 Mumma
(Continued)

FOREIGN PATENT DOCUMENTS

EP 0791330 A3 11/1997
EP 3505077 A1 7/2019
(Continued)

OTHER PUBLICATIONS

Alfieri, O. el al., "The double-orifice technique in mitral valve repair: a +A198:A225simple solution for complex problems," (2001) J. Thorne. Cardiovasc. Surg., 122(4):674-681.
(Continued)

Primary Examiner — Wade Miles
(74) Attorney, Agent, or Firm — David S. Barnhill; Chang & Hale

(57) ABSTRACT

Described herein are methods and apparatus for approximating targeted tissue by intertwining two or more sutures together. The sutures are attached to the targeted tissue and routed to a twister device. The twister device secures end portions of the sutures and twists them to intertwine the sutures. Controlling the number of twists provides control over the forces applied to the targeted tissue. In conjunction with visualization feedback, real-time adjustments can be made to achieved targeted results, such as elimination of mitral regurgitation when the disclosed methods and apparatus are applied to mitral valve repair.

19 Claims, 31 Drawing Sheets

(51) Int. Cl.
  *A61F 2/24*      (2006.01)
  *A61B 17/34*     (2006.01)
(52) U.S. Cl.
  CPC ........ *A61B 17/3423* (2013.01); *A61F 2/2427*
       (2013.01); *A61F 2/2457* (2013.01); *A61B*
          *17/0485* (2013.01); *A61B 2017/00243*
       (2013.01); *A61B 2017/0406* (2013.01); *A61B*
          *2017/0409* (2013.01); *A61B 2017/0417*
       (2013.01); *A61B 2017/0464* (2013.01); *A61B*
          *2017/0496* (2013.01); *A61B 2017/3425*
       (2013.01); *A61B 2017/3492* (2013.01); *A61F*
          *2/2442* (2013.01); *A61F 2/2466* (2013.01)
(58) Field of Classification Search
  CPC ........ A61B 17/0469; A61B 2017/0495; A61B
                                          2017/0496
  See application file for complete search history.

(56) References Cited

U.S. PATENT DOCUMENTS

| | | | |
|---|---|---|---|
| 4,403,797 A | 9/1983 | Ragland, Jr. |
| 4,662,376 A | 5/1987 | Belanger |
| 4,807,625 A | 2/1989 | Singleton |
| 5,144,961 A | 9/1992 | Chen et al. |
| 5,147,316 A | 9/1992 | Castillenti |
| 5,312,423 A | 5/1994 | Rosenbluth et al. |
| 5,391,176 A | 2/1995 | de la Torre |
| 5,405,352 A | 4/1995 | Weston |
| 5,454,821 A | 10/1995 | Harm et al. |
| 5,472,446 A | 12/1995 | de la Torre |
| 5,507,754 A | 4/1996 | Green et al. |
| 5,527,323 A | 6/1996 | Jervis et al. |
| 5,554,184 A | 9/1996 | Machiraju |
| 5,626,614 A | 5/1997 | Hart |
| 5,643,293 A | 7/1997 | Kogasaka et al. |
| 5,681,331 A | 10/1997 | de la Torre et al. |
| 5,716,368 A | 2/1998 | de la Torre et al. |
| 5,727,569 A | 3/1998 | Benetti et al. |
| 5,728,109 A | 3/1998 | Schulze et al. |
| 5,746,752 A | 5/1998 | Burkhart |
| 5,769,862 A | 6/1998 | Kammerer et al. |
| 5,797,928 A | 8/1998 | Kogasaka |
| 5,824,065 A | 10/1998 | Gross |
| 5,931,868 A | 8/1999 | Gross |
| 5,957,936 A | 9/1999 | Yoon et al. |
| 5,971,447 A | 10/1999 | Steck, III |
| 6,010,531 A | 1/2000 | Donlon et al. |
| 6,074,417 A | 6/2000 | Peredo |
| 6,269,819 B1 | 8/2001 | Oz et al. |
| 6,332,893 B1 | 12/2001 | Mortier et al. |
| 6,562,051 B1 | 5/2003 | Bolduc et al. |
| 6,626,930 B1 | 9/2003 | Allen et al. |
| 6,629,534 B1 | 10/2003 | St. Goer et al. |
| 6,752,810 B1 | 6/2004 | Gao et al. |
| 6,840,246 B2 | 1/2005 | Downing |
| 6,921,408 B2 | 7/2005 | Sauer |
| 6,940,246 B2 | 9/2005 | Mochizuki et al. |
| 6,978,176 B2 | 12/2005 | Lattouf |
| 6,991,635 B2 | 1/2006 | Takamoto et al. |
| 6,997,950 B2 | 2/2006 | Chawla |
| 7,112,207 B2 | 9/2006 | Allen et al. |
| 7,291,168 B2 | 11/2007 | Macoviak et al. |
| 7,294,148 B2 | 11/2007 | McCarthy |
| 7,309,066 B2 | 12/2007 | Carrier |
| 7,316,706 B2 | 1/2008 | Bloom et al. |
| 7,373,207 B2 | 5/2008 | Lattouf |
| 7,431,692 B2 | 10/2008 | Zollinger et al. |
| 7,513,908 B2 | 4/2009 | Lattouf |
| 7,534,260 B2 | 5/2009 | Lattout |
| 7,608,091 B2 | 10/2009 | Goldfarb et al. |
| 7,618,449 B2 | 11/2009 | Tremulis et al. |
| 7,632,308 B2 | 12/2009 | Loulmet |
| 7,635,386 B1 | 12/2009 | Gammie |
| 7,666,196 B1 | 2/2010 | Miles |
| 7,744,609 B2 | 6/2010 | Allen et al. |
| 7,837,727 B2 | 11/2010 | Goetz et al. |
| 7,871,368 B2 | 1/2011 | Zollinger et al. |
| 7,871,433 B2 | 1/2011 | Lattouf |
| 7,959,650 B2 | 6/2011 | Kaiser et al. |
| 8,029,518 B2 | 10/2011 | Goldfarb et al. |
| 8,029,565 B2 | 10/2011 | Lattouf |
| 8,043,368 B2 | 10/2011 | Crabtree |
| 8,147,542 B2 | 4/2012 | Maisano et al. |
| 8,187,323 B2 | 5/2012 | Mortier et al. |
| 8,226,711 B2 | 7/2012 | Mortier et al. |
| 8,241,304 B2 | 8/2012 | Bachman |
| 8,252,050 B2 | 8/2012 | Maisano et al. |
| 8,292,884 B2 | 10/2012 | Levine et al. |
| 8,303,622 B2 | 11/2012 | Aikhatib |
| 8,333,788 B2 | 12/2012 | Maiorino |
| 8,382,829 B1 | 2/2013 | Call et al. |
| 8,439,969 B2 | 5/2013 | Gillinov et al. |
| 8,454,656 B2 | 6/2013 | Tuval |
| 8,465,500 B2 | 6/2013 | Speziali |
| 8,475,525 B2 | 7/2013 | Maisano et al. |
| 8,500,800 B2 | 8/2013 | Maisano et al. |
| 8,608,758 B2 | 12/2013 | Singhatat et al. |
| 8,663,278 B2 | 3/2014 | Mabuchi et al. |
| 8,771,296 B2 | 7/2014 | Nobles et al. |
| 8,828,053 B2 | 9/2014 | Sengun et al. |
| 8,652,213 B2 | 10/2014 | Gammie et al. |
| 8,888,791 B2 | 11/2014 | Jaramillo et al. |
| 8,940,008 B2 | 1/2015 | Kunis |
| 9,131,884 B2 | 9/2015 | Holmes et al. |
| 9,192,287 B2 | 11/2015 | Saadat et al. |
| 2002/0013571 A1 | 1/2002 | Goldfarb et al. |
| 2003/0023254 A1 | 1/2003 | Chiu |
| 2003/0094180 A1 | 5/2003 | Benetti |
| 2003/0105519 A1 | 6/2003 | Fasol et al. |
| 2003/0120264 A1 | 6/2003 | Lattouf |
| 2003/0120341 A1 | 6/2003 | Shennib et al. |
| 2004/0044365 A1 | 3/2004 | Bachman |
| 2004/0093023 A1 | 5/2004 | Allen et al. |
| 2004/0199183 A1 | 10/2004 | Oz et al. |
| 2005/0004667 A1 | 1/2005 | Swinford et al. |
| 2005/0019735 A1 | 1/2005 | Demas |
| 2005/0075654 A1 | 4/2005 | Kelleher |
| 2005/0149067 A1 | 7/2005 | Takemoto et al. |
| 2005/0149093 A1 | 7/2005 | Pokorney |
| 2005/0154402 A1 | 7/2005 | Sauer |
| 2005/0216036 A1 | 9/2005 | Nakao |
| 2005/0216077 A1 | 9/2005 | Mathis et al. |
| 2005/0261710 A1 | 11/2005 | Sakamoto et al. |
| 2005/0267493 A1 | 12/2005 | Schreck et al. |
| 2006/0030866 A1 | 2/2006 | Schreck |
| 2006/0100698 A1 | 5/2006 | Lattouf |
| 2006/0111739 A1 | 5/2006 | Staufer et al. |
| 2006/0167541 A1 | 7/2006 | Lattouf |
| 2006/0190030 A1 | 8/2006 | To et al. |
| 2006/0282088 A1 | 12/2006 | Ryan |
| 2007/0001857 A1 | 1/2007 | Hartmann et al. |
| 2007/0049952 A1 | 3/2007 | Weiss |
| 2007/0055292 A1 | 3/2007 | Ortiz et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0149995 A1 | 6/2007 | Quinn et al. |
| 2007/0197858 A1 | 8/2007 | Goldfarb et al. |
| 2007/0213582 A1 | 9/2007 | Zollinger et al. |
| 2007/0270793 A1 | 11/2007 | Lattouf |
| 2008/0004597 A1 | 1/2008 | Lattouf et al. |
| 2008/0009888 A1 | 1/2008 | Ewers et al. |
| 2008/0065203 A1 | 3/2008 | Khalapyan |
| 2008/0140093 A1 | 6/2008 | Stone et al. |
| 2008/0167714 A1 | 7/2008 | St. Goar et al. |
| 2008/0188893 A1 | 8/2008 | Selvitelli et al. |
| 2008/0195126 A1 | 8/2008 | Solem |
| 2008/0228223 A1 | 9/2008 | Alkhatib |
| 2008/0249504 A1 | 10/2008 | Lattouf et al. |
| 2008/0269781 A1 | 10/2008 | Funamura et al. |
| 2008/0319458 A1 | 12/2008 | Reynolds |

(56) References Cited

U.S. PATENT DOCUMENTS

| | | | |
|---|---|---|---|
| 2009/0005863 A1 | 1/2009 | Goetz et al. | |
| 2009/0043153 A1 | 2/2009 | Zollinger et al. | |
| 2009/0105729 A1 | 4/2009 | Zentgraf | |
| 2009/0105751 A1 | 4/2009 | Zentgraf | |
| 2009/0276038 A1 | 11/2009 | Tremulis et al. | |
| 2010/0023056 A1 | 1/2010 | Johansson et al. | |
| 2010/0023117 A1 | 1/2010 | Yoganathan et al. | |
| 2010/0023118 A1 | 1/2010 | Medlock et al. | |
| 2010/0042147 A1 | 2/2010 | Janovsky et al. | |
| 2010/0174297 A1 | 7/2010 | Speziali | |
| 2010/0179574 A1 | 7/2010 | Longoria et al. | |
| 2010/0210899 A1 | 8/2010 | Schankereli | |
| 2010/0298929 A1* | 11/2010 | Thornton | A61F 2/2445 623/2.1 |
| 2010/0298930 A1 | 11/2010 | Oriov | |
| 2011/0015476 A1 | 1/2011 | Franco | |
| 2011/0022083 A1 | 1/2011 | DiMatteo et al. | |
| 2011/0022084 A1 | 1/2011 | Sengun et al. | |
| 2011/0028995 A1 | 2/2011 | Miraki et al. | |
| 2011/0029071 A1 | 2/2011 | Zlotnick et al. | |
| 2011/0060407 A1 | 3/2011 | Ketai et al. | |
| 2011/0106106 A1 | 5/2011 | Meier et al. | |
| 2011/0144743 A1 | 6/2011 | Lattouf | |
| 2011/0245868 A1 | 10/2011 | Teeslink et al. | |
| 2011/0264208 A1 | 10/2011 | Duffy et al. | |
| 2011/0270278 A1 | 11/2011 | Overes et al. | |
| 2011/0288637 A1 | 11/2011 | De Marchena | |
| 2011/0307055 A1 | 12/2011 | Goldfarb et al. | |
| 2012/0004669 A1 | 1/2012 | Overes et al. | |
| 2012/0143215 A1 | 6/2012 | Corrao et al. | |
| 2012/0150223 A1 | 6/2012 | Manos et al. | |
| 2012/0179184 A1 | 7/2012 | Orlov | |
| 2012/0184971 A1 | 7/2012 | Zentgraf et al. | |
| 2012/0203072 A1 | 8/2012 | Lattouf et al. | |
| 2012/0226294 A1 | 9/2012 | Tuval | |
| 2012/0226349 A1 | 9/2012 | Tuval et al. | |
| 2013/0018459 A1 | 1/2013 | Maisano et al. | |
| 2013/0035757 A1 | 2/2013 | Zentgraf et al. | |
| 2013/0253641 A1 | 9/2013 | Lattouf | |
| 2013/0282059 A1 | 10/2013 | Ketai et al. | |
| 2013/0345749 A1 | 12/2013 | Suilivan et al. | |
| 2014/0031926 A1 | 1/2014 | Kudlik et al. | |
| 2014/0039607 A1 | 2/2014 | Kovach | |
| 2014/0067052 A1 | 3/2014 | Chau et al. | |
| 2014/0094906 A1* | 4/2014 | Spence | A61F 2/2442 623/2.36 |
| 2014/0114404 A1 | 4/2014 | Gammie et al. | |
| 2014/0214152 A1 | 7/2014 | Bielefeld | |
| 2014/0243968 A1 | 8/2014 | Padala | |
| 2014/0364938 A1 | 12/2014 | Longoria et al. | |
| 2015/0032127 A1 | 1/2015 | Gammie et al. | |
| 2015/0045879 A1 | 2/2015 | Longoria et al. | |
| 2020/0155315 A1 | 5/2020 | Zhang et al. | |

FOREIGN PATENT DOCUMENTS

| | | |
|---|---|---|
| JP | 2013517110 A | 5/2013 |
| WO | 2004037463 A1 | 5/2004 |
| WO | 2006127509 A2 | 11/2006 |
| WO | 2007100268 A2 | 9/2007 |
| WO | 2007119057 A1 | 10/2007 |
| WO | 2008013869 A2 | 1/2008 |
| WO | 2008124110 A3 | 12/2008 |
| WO | 2008143740 A3 | 2/2009 |
| WO | 2006078694 A3 | 4/2009 |
| WO | 2009081396 A2 | 7/2009 |
| WO | 2010070649 A1 | 6/2010 |
| WO | 2010105046 A1 | 9/2010 |
| WO | 2013003228 A1 | 1/2013 |
| WO | 2014093861 A1 | 6/2014 |
| WO | 2015020816 A1 | 2/2015 |
| WO | 2016192481 A1 | 12/2016 |
| WO | 2012137208 A1 | 6/2018 |

OTHER PUBLICATIONS

Barbero-Marcial, M. et al., "Transxiphoid Approach Without Median Sternotomy for the Repair of Atrial Septal Defects," (1998) Ann. Thorne. Surg., 65(3):771-774

Braunberger, E. et al., "Very long-term results (more than 20 years) of valve repair with Carpentier's echniques in nonheumatic mitral valve insufficiency," (2001) Circulation, 104:1-8-1-11.

Carpentier, Alain, "Cardiac valve surgery—the 'French coffection'," The Journal of Thoracic and Cardiovascular Surgery, vol. 86, No. 3, Sep. 1983, 15 pages.

David, T. E. et al., "Mitral valve repair by replacement of chordae tendineae with polytetrafluoroethylene sutures," (1991) J. Thorne. Cardiovasc. Surg., 101 (3 ):495-50 I.

David, T. E. et al., "Replacement of chordae tendineae with Gore-Tex sutures: a ten-year experience," ( 1996) J. Heart Valve Dis., 5( 4 ):352-355.

Doty, D. B. et al., "Full-Spectrum Cardiac Surgery Through a Minimal Incision: Mini-Sternotomy (Lower Half) Technique." (1998) Ann. Thorne. Surg., 65(2):573-577.

Duran, C. M. G. et al., "Techniques for ensuring the correct length of new mitral chords," (2003) .I. Heart Valve Dis., 12(2)156-161.

Eishi, K. et al., "Long-term results of artificial chordae implantation in patients with mitral valve prolapse," (1997) J. Heall Valve Dis., 6(6):594-598.

Frater, R. W. M. et al., "Chordal replacement in mitral valve repair," (1990) Circulation, 82(suppl. IV):IV-125-IV-130.

Frater, R. W. M., "Anatomical rules for the plastic repair of a diseased mitral valve," (1964) Thorax. 19:458-464.

Huber, C.H. et al., "Direct Access Valve Replacement (DAVR)—are we entering a new era in cardiac surgery?" (2006) European Journal of Cardio-thoracic Surgery, 29:380-385.

Hvass, U. et al., "Papillary Muscle Sling: A New Functional Approach to Mitral Repair in Patients With Ischemic Left Ventricular Dysfunction and Functional Mitral Regurgitation," (2003) Ann. Thorne. Surg., 75:809-811

Kasegawa, H. et al., "Simple method for determining proper length of allificial chordae in mitral valve repair," (1994) Ann. Thorne. Surg., 57(1 ):237-239.

Kobayashi, J. et al., "Ten-year experience of chordal replacement with expanded polytetrafluoroethylene in mitral valve repair," (2000) Circulation, J 02(19 Suppl 3),1ii-30-Jii-34.

Kunzelman, K. et al., "Replacement of mitral valve posterior chordae tenclincae with expanded polytetrafluorocthylcnc suture: a finite element study," (1996) J. Card. Surg., 11(2):136-145.

Langer, F. et al., "RING plus STRING: Papillary muscle repositioning as an adjunctive repair technique for ischemic mitral regurgitation," (2007) J. Thorne. Cardiovasc. Surg., 133( I): 247-249.

Maisano, F. et al., "The double-orifice technique as a standardized approach to treat mitral regurgitation due to severe myxomatous disease: surgical technique," (2000) European Journal of Cardio-thorncic Surgery, 17(3):201-205.

Merendino, K. A. et al., "The open con-ection of rheumatic mitral regurgitation and/or stenosis with special reference to regurgitation treated by posterornedial annuloplasty utilizing a pump-oxygenator," (1959) Annals of Surgery, 150(1 ):5-22.

Minatoya, K. et al., "Pathologic aspects of polytetrafluoroethylene sutures in human heart," (1996) Ann. Thorac. Surg., 61 (3 ):883-887.

Mohty, D. et al., "Very long-term survival and durability of mitral valve repair for mitral valve prolapse," (2001) Circulation, 104:1-1-1-7.

*Neochord, Inc.* v. *University of Maryland, Baltimore*, Case No. JPR2016-00208, Decision on Institution of Inter Faries Review,37 Cfr §42. I 08, Paper 6, Entered May 24, 2016, 28 pages.

*Neochord, Inc.* v. *University of Maryland, Baltimore*, Case No, IPR2016-00208, Declaration of Dr. Lishan Aklog, dated Nov. 17, 2015, 91 pages.

*Neochord, Inc.* v. *University of Maryland, Baltimore*, Case No. IPR2016-00208, Petition for Inter Partes Review of U.S. Pat. No. 7,635,386, dated Nov. 18, 2015, 65 pages.

(56) References Cited

OTHER PUBLICATIONS

Nigro, J. J. et al., "Neochordal repair of the posterior mitral leaflet," (2004) J. Thorne. Cardiovasc. Surg., 127 (2):440-447.

Phillips, M. R. et al., "Repair of anterior leaflet mitral valve prolapse: chordal replacement versus chordal shrntening." (2000) Ann. Thorac. Surg., 69(1):25-29.

Russo, M. J. et al. ."Transapical Approach for Mitral Valve Repair during Insertion of a Left Ventricular Assist Device," Hindawi Publishing Corporation, The Scientific World Journal, vol. 2013, Article ID 925310, [online], Retrieved from the internet: <URL: http://dx.doi.org/J 0.1155/2013/92531 O> Apr. 11, 2013, 4 pages.

Sarsam, M.A. I., "Simplified technique for determining the length of artificial cl1ordae in milral valve repair," (2002) Ann. Thorac. Surg., 73(5): 1659-1660.

Savage, E. B. et al., Use of mitral valve repair: analysis of contemporary United States experience reported to the society of thoracic surgeons national cardiac database,. .(2003) Ann. Thorne. Surg., 75:820-825.

Speziali, G. et al., "Coll'ection of Mitral Valve Regurgitation by Off-Pump, Transapical Placement of Artificial Chordae Tendinae, Results of the European TACT Trial," AATS 93rd Annual Meeting 2013, www.aats.org, 26 pages.

Suematsu, Y. et al., "Three-dimensional echo-guided beating heaii surgery without cardiopulmonary bypass: Atrial septal defect closure in a swine model," (2005) J. Thorne. Cardiovasc. Surg., 130: 1348-1357

Von Oppell, Oppell, U. 0. et al., "Chordal replacement for both minimally invasive and conventional mitral valve surgery using premcasured Gore-Tex loops," (2000) Ann. Thorne. Surg., 70(6):2166-2168.

Zussa, C. et al., Artificial rnitral valve chordae: experimental and clinical experience; (1990) Ann. Thorne. Surg., 50 (3):367-373.

Zussa, C. et al., "Seven-year experience with chordal replacement with expanded polytetrafluoroethylene in floppyrnitral valve," (1994)1. Thorac. Cardiovasc. Surg., 108(1):37-41.

Zussa, C. et al., "Surgical technique for artificial mitral chordae implantation," (1991) Journal of Cardiac Surgery, 6 (4):432-438.

Zussa, C., "Artificial chordae," (1995) J. Heart Valve Dis., 4(2):S249-S256.

\* cited by examiner

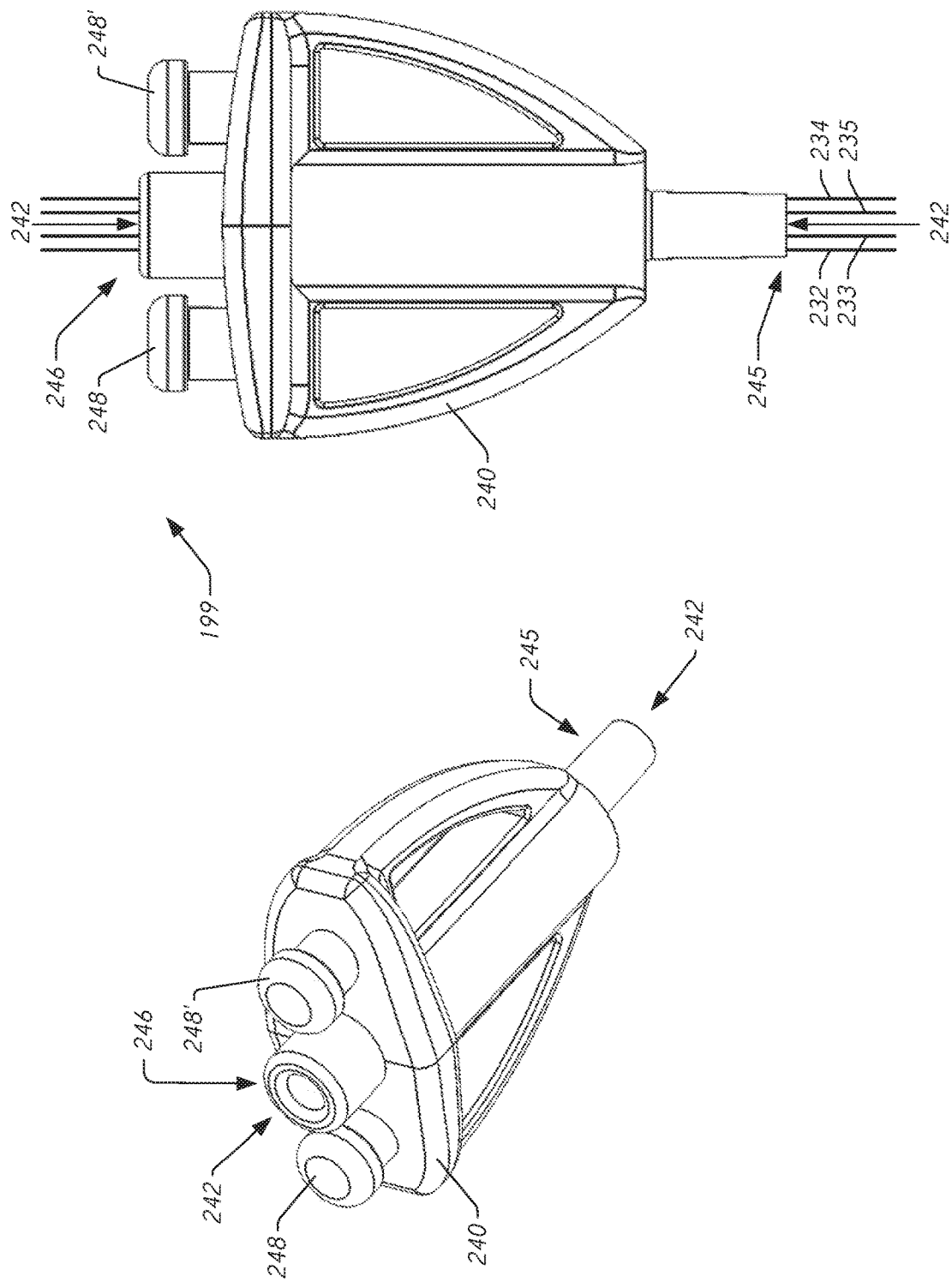

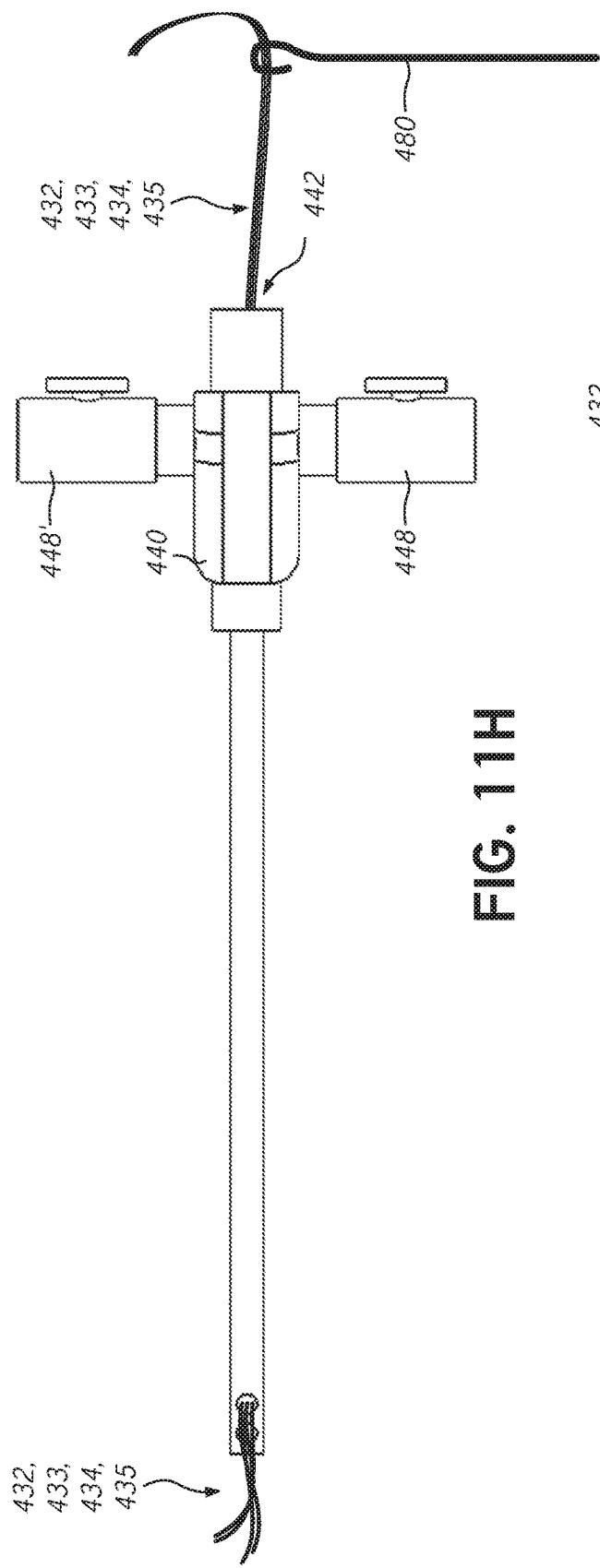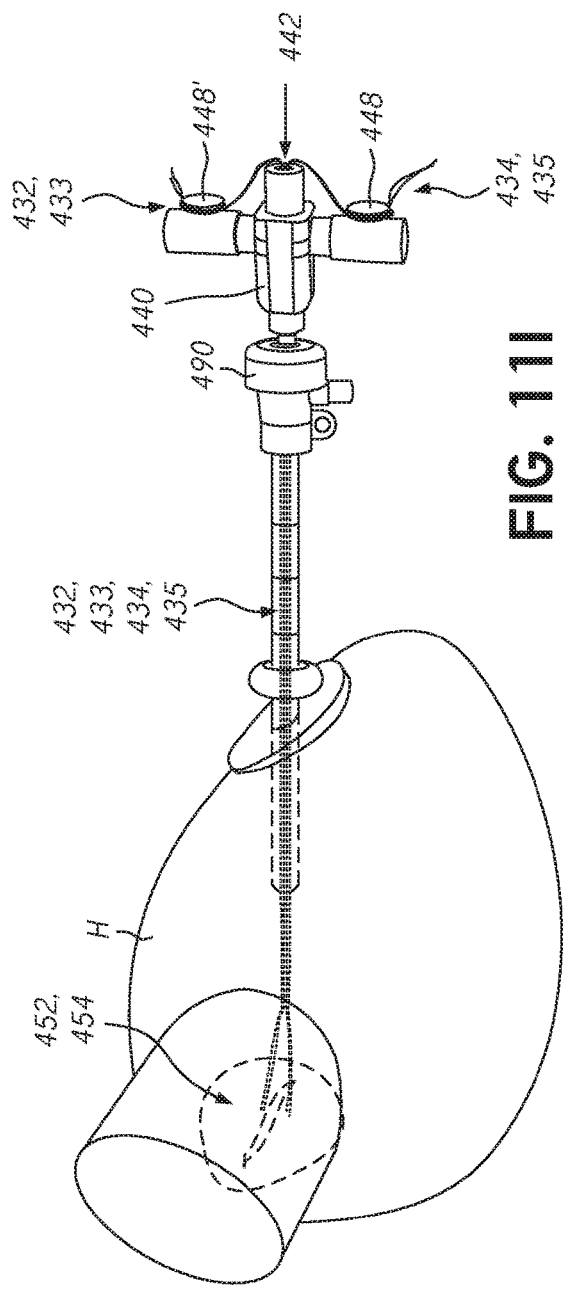

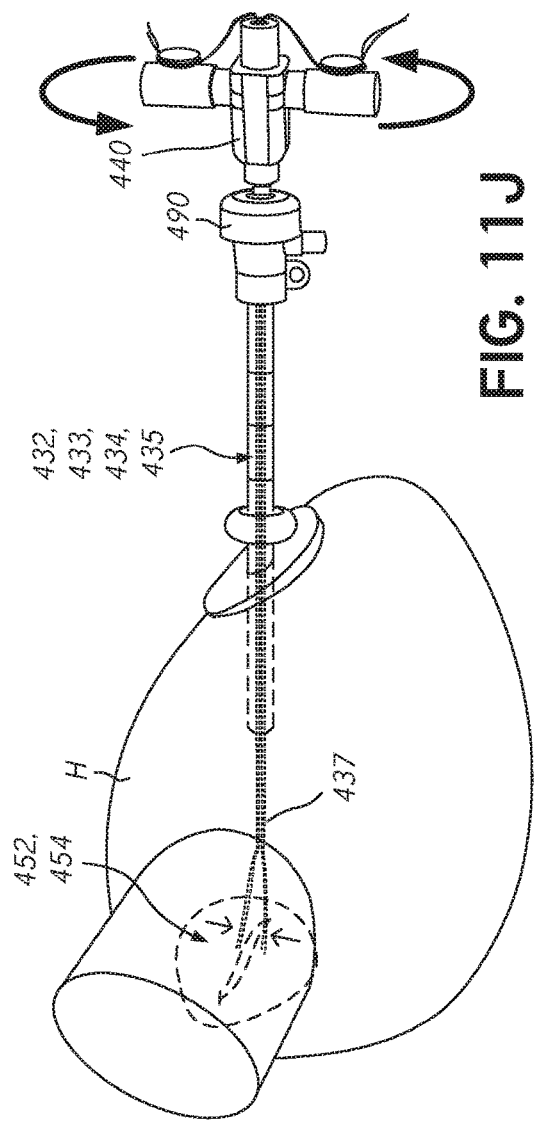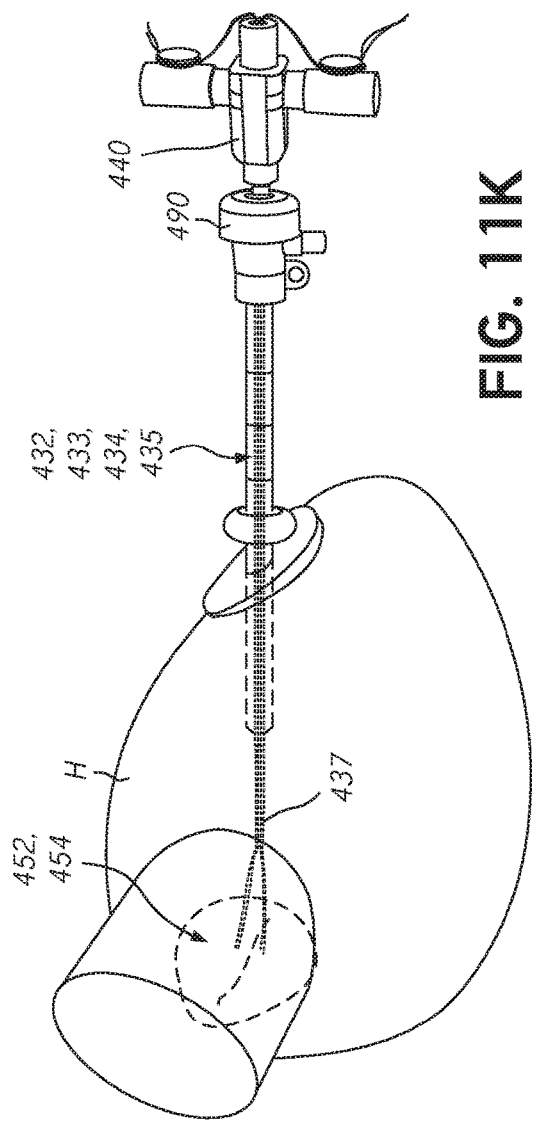

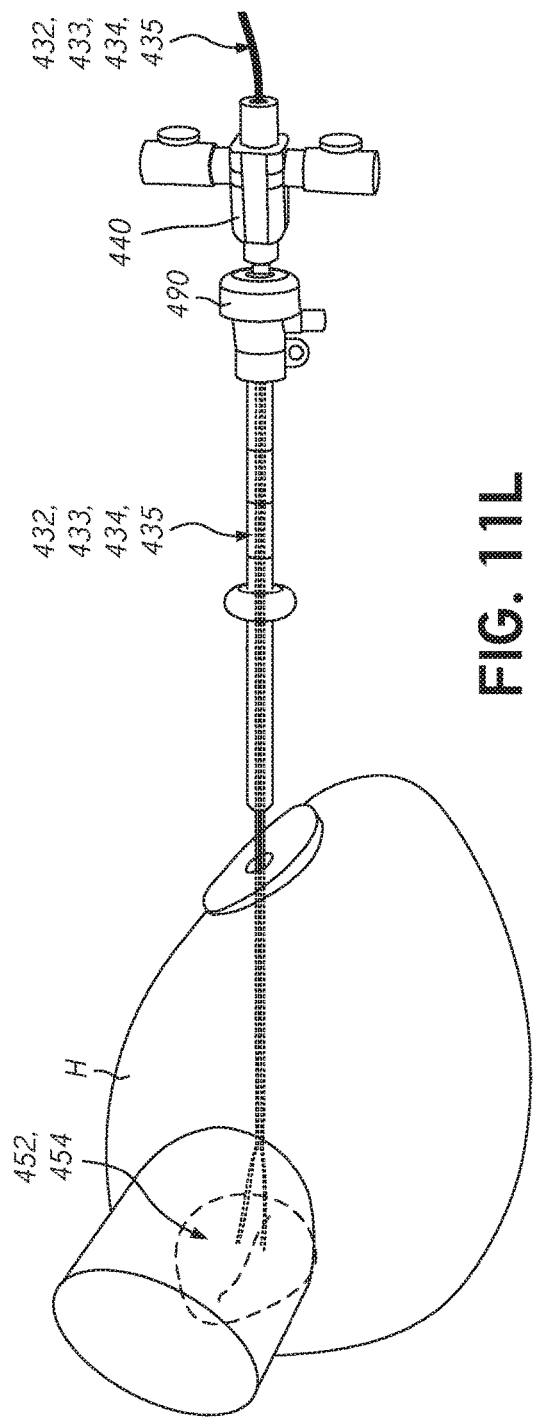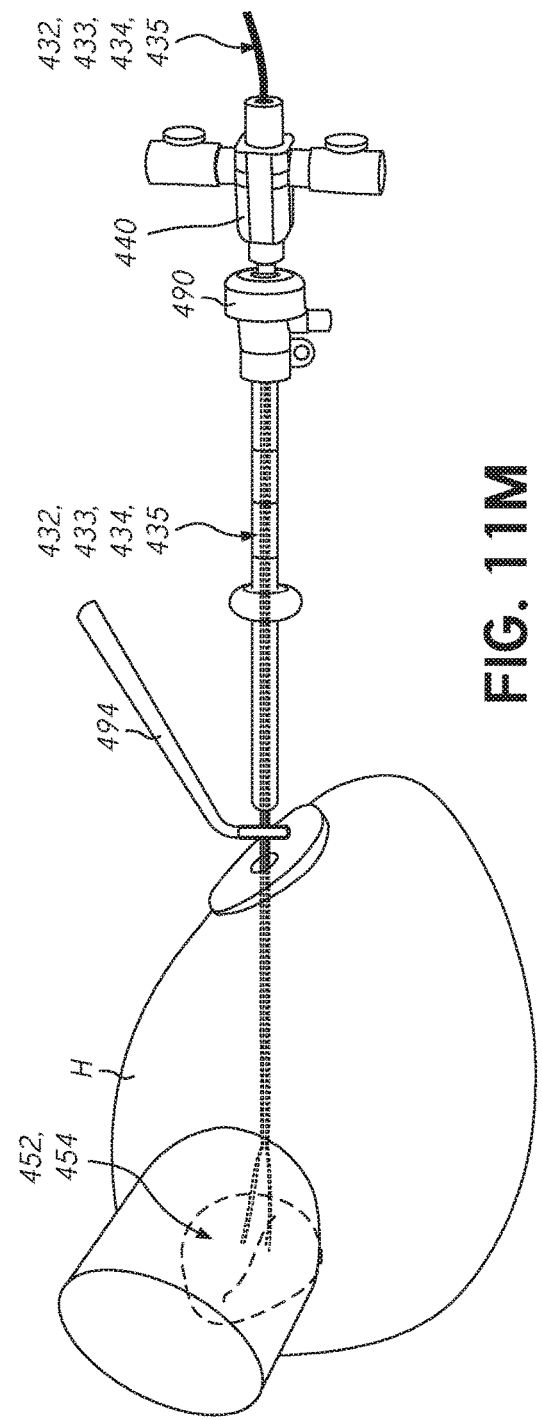

METHOD AND APPARATUS FOR CARDIAC PROCEDURES

CROSS-REFERENCE TO RELATED APPLICATIONS

This application claims the benefit of U.S. Application No. 62/521,784 entitled "METHOD AND APPARATUS FOR CARDIAC PROCEDURES," filed Jun. 19, 2017, which is expressly incorporated by reference herein in its entirety for all purposes.

BACKGROUND

Field

Some embodiments described herein relate to methods and apparatus for joining two or more sutures together during surgical procedures, such as cardiac valve repairs, and more particularly, methods and apparatus for performing minimally invasive mitral or tricuspid valve repairs.

Description of Related Art

Various disease processes can impair the proper functioning of one or more of the valves of the heart. These disease processes include degenerative processes (e.g., Barlow's Disease, fibroelastic deficiency), inflammatory processes (e.g., Rheumatic Heart Disease), and infectious processes (e.g., endocarditis). Additionally, damage to the ventricle from prior heart attacks (e.g., myocardial infarction secondary to coronary artery disease) or other heart diseases (e.g., cardiomyopathy) can distort the geometry of the heart causing valves in the heart to dysfunction. The vast majority of patients undergoing valve surgery, such as mitral valve surgery, suffer from a degenerative disease that causes a malfunction in a leaflet of the valve, which results in prolapse and regurgitation.

Generally, a heart valve may malfunction in two different ways. One possible malfunction, valve stenosis, occurs when a valve does not open completely and thereby causes an obstruction of blood flow. Typically, stenosis results from buildup of calcified material on the leaflets of the valves causing the leaflets to thicken, thereby impairing their ability to fully open and permit adequate forward blood flow.

Another possible malfunction, valve regurgitation, occurs when the leaflets of the valve do not close completely thereby allowing blood to leak back into the prior chamber when the heart contracts. There are three mechanisms by which a valve becomes regurgitant or incompetent; they include Carpentier's type I, type II and type III malfunctions. A Carpentier type I malfunction involves the dilation of the annulus such that the area of the valve orifice increases. The otherwise normally functioning leaflets do not have enough surface area to cover the enlarged orifice and fail to form a tight seal (e.g., do not coapt properly) causing regurgitation. Included in a type I mechanism malfunction are perforations of the valve leaflets, as in endocarditis. A Carpentier's type II malfunction involves prolapse of a segment of one or both leaflets above the plane of coaptation. This is the most commonly treated cause of mitral regurgitation, and is often caused by the stretching or rupturing of chordae tendineae normally connected to the leaflet. A Carpentier's type III malfunction involves restriction of the motion of one or more leaflets such that the leaflets are abnormally constrained below the level of the plane of the annulus. Leaflet restriction can be caused by rheumatic heart disease (IIIa) or dilation of the ventricle (IIIb).

Mitral valve disease is the most common valvular heart disorder, with nearly 4 million Americans estimated to have moderate to severe mitral valve regurgitation ("MR"), with similar numbers of individuals impacted outside of the United States. MR results in a volume overload on the left ventricle which in turn progresses to ventricular dilation, decreased ejection performance, pulmonary hypertension, symptomatic congestive heart failure, atrial fibrillation, right ventricular dysfunction and death. Successful surgical mitral valve repair restores mitral valve competence, abolishes the volume overload on the left ventricle, improves symptom status, and prevents adverse left ventricular remodeling. While generally safe and effective, conventional open-heart operations are invasive, result in significant disability, and require extended post-procedure recovery. Patients routinely spend five to seven days in the hospital and often are not able to return to normal daily activities for a month or more.

Malfunctioning valves may either be repaired or replaced. Repair typically involves the preservation and correction of the patient's own valve. Replacement typically involves replacing the patient's malfunctioning valve with a biological or mechanical substitute. Typically, replacement is preferred for stenotic damage sustained by the leaflets because the stenosis is irreversible. The mitral valve and tricuspid valve, on the other hand, are more prone to deformation. Deformation of the leaflets, as described above, prevents the valves from closing properly and allows for regurgitation or back flow of blood from the ventricle into the atrium, which results in valvular insufficiency. Deformations in the structure or shape of the mitral valve or tricuspid valve are often repairable.

In many instances of mitral valve regurgitation, repair is preferable to valve replacement. Mitral valve replacement operations have a 2× higher risk of operative mortality (Risk Standardized Mortality 1.65% vs. 2.96%), 2× higher risk of stroke per year (1.15% vs. 2.2%) and a 10× higher risk of infection per year (0.1% vs. 1.0%). Patients who receive a quality mitral valve repair operation do not require anticoagulation and rarely require reoperation. This is in stark contrast to mechanical valve replacement which mandates lifelong anticoagulation and bioprosthetic valve replacement with the eventual certainty of prosthetic valve dysfunction and reoperation. Compared to mitral valve replacement, mitral valve repair results in improved left ventricular function and has superior long-term survival. Therefore, an improperly functioning mitral valve or tricuspid valve is ideally repaired, rather than replaced. Because of the complex and technical demands of the current repair procedures, however, the mitral valve is still replaced in approximately one third of all mitral valve operations performed in the United States.

Studies suggest that Carpentier type II malfunction, often referred to as "Degenerative," "Primary" or "Organic" MR, accounts for as much as 60% of MR. Resectional mitral valve repair techniques, initially described by Dr. Carpentier, involve cutting out (resecting) a section of the prolapsed leaflet tissue, stitching the remaining tissue together and implanting an annuloplasty ring around the annulus. Removing a portion of one or both of the mitral valve leaflets during such a resectional repair decreases the available leaflet tissue to seal the mitral orifice. To accommodate the decrease caused by the resectional repair, in many instances, an annuloplasty ring must be implanted to decrease the size of the mitral orifice.

Implanting an annuloplasty ring introduces various risks. For example, implanting an annuloplasty ring can increase pressure gradients across the valve. Further, an annuloplasty ring can lead to infection and/or annuloplasty ring dehiscence—a well-documented failure mode of valve repair surgery. Implanting an annuloplasty ring can further impact the dynamic nature of the mitral valve annulus throughout the cardiac cycle. In a healthy person, for example, the mitral valve annulus relaxes during diastole and contracts with the rest of the left ventricle during systole, causing the annulus to expand and contract as the heart beats. Implanting an annuloplasty ring can interfere with such normal functioning of the heart. To combat such interference, flexible annuloplasty rings and partial bands have been developed to minimize the impact a rigid or complete annuloplasty ring can have on the dynamic movement of the mitral annulus. To avoid the aforementioned complications and risks, an effective mitral valve repair procedure that eliminated the need for an annuloplasty ring is desirable, particularly a repair that can be performed minimally-invasively and off-pump in which implanting an annuloplasty ring would be present technical challenges.

More recently many surgeons have moved to a "non-resectional" repair technique where artificial chordae tendineae ("cords") made of expanded polytetrafluoroethylene ("ePTFE") suture, or another suitable material, are placed in the prolapsed leaflet and secured to the heart in the left ventricle, normally to the papillary muscle. Because the native leaflet tissue is maintained in non-resectional repairs, they often result in a larger surface of coaptation between the posterior and anterior mitral valve leaflets, but properly sizing the cords on a flaccid heart can be very challenging, especially for the low volume mitral valve surgeon. Implanting an annuloplasty ring with such non-resectional repairs on a stopped heart is currently the standard of care. Implanting an annuloplasty ring in a beating heart repair is technically challenging and rarely done in practice due in large part to the costs associated with two separate procedures (e.g., cordal repair and annuloplasty). A device that can quickly and easily perform a beating-heart cordal repair while also addressing the mitral annulus would be a major advancement.

Carpentier type I malfunction, sometimes referred to as "Secondary" or "Functional" MR, is associated with heart failure and affects between 1.6 and 2.8 million people in the United States alone. Studies have shown that mortality doubles in patients with untreated mitral valve regurgitation after myocardial infarction. Unfortunately, there is no gold standard surgical treatment paradigm for functional MR and most functional MR patients are not referred for surgical intervention due to the significant morbidity, risk of complications and prolonged disability associated with cardiac surgery. Surgeons use a variety of approaches ranging from valve replacement to insertion of an undersized mitral valve annuloplasty ring for patients suffering from functional MR and the long-term efficacy is still unclear. In a randomized study of on-pump, open-heart mitral valve repair versus mitral valve replacement for functional MR, mitral valve replacement had a similar mortality rate and resulted in significantly less recurrent MR after one year and two years. According to some, a subsequent sub-analysis of subjects in the repair group suggests that the people who received a "good repair" did better than the replacement group but that when the repair arm was compared to mitral valve replacement, the "bad repairs" caused the replacement arm to perform better. Either way, there is a need for better treatment options for functional MR. Less invasive, beating-heart, transcatheter repair and replacement technologies are of particular interest because they do not require cardiopulmonary bypass, cardioplegia, aortic cross-clamping or median sternotomy.

Dr. Alfieri has demonstrated the benefit of securing the midpoint of both leaflets together creating a double orifice valve in patients with MR known as an "Edge-to-Edge" repair or an Alfieri procedure. The ability to combine a neochordal repair with an edge-to-edge repair in degenerative MR patients with a dilated annulus and who do not receive an annuloplasty ring because the repair is done in a minimally-invasive, off-pump procedure, has particular promise. Further, performing a facilitated edge-to-edge repair in which sutures placed on both the posterior and anterior leaflets are secured together and then pulled toward the base of the heart has the potential to improve the overall repair. Performing a facilitated edge-to-edge procedure in a minimally-invasive beating heart procedure is a further advancement. Further, in addition to or instead of creating the edge-to-edge relationship, to promote a larger surface of coaptation between the anterior and posterior leaflets, and thereby to promote proper valve function and limit or prevent undesirable regurgitation, sutures extending from the leaflets can be secured together to pull or to otherwise move the posterior annulus towards the anterior leaflet and/or the anterior annulus towards to posterior leaflet. This reduces the distance between the anterior annulus and the posterior annulus (or the septal-lateral distance) (e.g., by about 10%-30%). Approximating the anterior annulus and the posterior annulus in this manner can decrease the valve orifice, and thereby decrease, limit, or otherwise prevent undesirable regurgitation.

Regardless of whether a replacement or repair procedure is being performed, conventional approaches for replacing or repairing cardiac valves are typically invasive open-heart surgical procedures, such as sternotomy or thoracotomy, which require opening up of the thoracic cavity so as to gain access to the heart. Once the chest has been opened, the heart is bypassed and stopped. Cardiopulmonary bypass is typically established by inserting cannulae into the superior and inferior vena cavae (for venous drainage) and the ascending aorta (for arterial perfusion), and connecting the cannulae to a heart-lung machine, which functions to oxygenate the venous blood and pump it into the arterial circulation, thereby bypassing the heart. Once cardiopulmonary bypass has been achieved, cardiac standstill is established by clamping the aorta and delivering a "cardioplegia" solution into the aortic root and then into the coronary circulation, which stops the heart from beating. Once cardiac standstill has been achieved, the surgical procedure may be performed. These procedures, however, adversely affect almost all of the organ systems of the body and may lead to complications, such as strokes, myocardial "stunning" or damage, respiratory failure, kidney failure, bleeding, generalized inflammation, and death. The risk of these complications is directly related to the amount of time the heart is stopped ("cross-clamp time") and the amount of time the subject is on the heart-lung machine ("pump time").

Thus, there is a significant need to perform mitral valve repairs using less invasive procedures while the heart is still beating. Accordingly, there is a continuing need for new procedures and devices for performing cardiac valve repairs, such as mitral valve repair, which are less invasive, do not require cardiac arrest, and are less labor-intensive and technically challenging.

SUMMARY

Apparatus and methods for repairing a tissue by remotely securing two or more sutures together are described herein.

In some embodiments, apparatus and methods for performing a non-invasive procedure to repair a cardiac valve are described herein. In some embodiments, apparatus and methods are described herein for repairing a mitral valve using an edge-to-edge procedure (also referred to as an Alfieri procedure) to secure the mitral valve leaflets.

In a first aspect, the present disclosure provides a method for twisting sutures together to approximate anchor implants attached to targeted tissue. The method includes attaching two or more cords to targeted tissue, individual cords including a distal anchor implant and a suture extending proximally from the distal anchor implant. The method also includes securing proximal end portions of the two or more sutures to a twister device. The method also includes operating the twister device to cause the two or more sutures to intertwine. The method also includes receiving feedback from a visualization system, the feedback including an approximation of the targeted tissue. The method also includes anchoring the proximal end portions of the two or more sutures to prevent unwinding of the two or more sutures.

In some embodiments of the first aspect, the targeted tissue is within a targeted region and the twister device is operated outside of the targeted region. In further embodiments of the first aspect, the targeted region is the heart. In further embodiments of the first aspect, anchoring the proximal end portions of the two or more sutures includes securing the proximal end portions to an external wall of the heart. In further embodiments of the first aspect, the method further includes inserting a portion of the twister device into a valve introducer that provides access to the targeted tissue within the targeted region.

In some embodiments of the first aspect, the targeted tissue includes a leaflet of a mitral valve. In further embodiments of the first aspect, the targeted tissue includes a posterior leaflet. In further embodiments of the first aspect, the targeted tissue includes an anterior leaflet.

In some embodiments of the first aspect, the method further includes adjusting a tension of the two or more sutures. In further embodiments of the first aspect, adjusting a tension of the two or more sutures occurs simultaneously with operating the twister device to cause the two or more sutures to intertwine.

In some embodiments of the first aspect, operating the twister device to cause the two or more sutures to intertwine results in a point of intersection that approaches the targeted tissue to change a force vector on the two or more cords attached to the targeted tissue.

In a second aspect, the present disclosure provides a twister device that includes a body; a suture management component coupled to the body, the suture management component having one or more features to receive end portions of two or more sutures and to secure the received suture end portions to the body; and a twisting component coupled to the body, the twisting component configured to rotate the suture management component to intertwine the two or more sutures.

In some embodiments of the second aspect, the suture management component includes two or more tie knobs. In further embodiments of the second aspect, the suture management component further includes suture locks configured to releasably engage with the two or more tie knobs to secure the suture end portions to the two or more tie knobs.

In some embodiments of the second aspect, the suture management component includes a rotating spin lock. In further embodiments of the second aspect, the rotating spin lock includes an adjustable leak proof seal configured to grip the suture end portions and to prevent backflow of fluids during operation of the twister device.

In some embodiments of the second aspect, the twister device further includes a side port configured to receive a fluid to prevent blood from clotting.

In some embodiments of the second aspect, the body forms a lumen configured to allow two or more sutures to pass therethrough. In further embodiments of the second aspect, the suture management component is formed on a proximal side of the body and the lumen runs from the proximal side to the distal side of the body. In further embodiments of the second aspect, the suture management component is configured to secure the received suture end portions that are routed from the distal side to the proximal side of the body through the lumen.

For purposes of summarizing the disclosure, certain aspects, advantages and novel features have been described herein. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

BRIEF DESCRIPTION OF THE DRAWINGS

FIGS. 8A and 8B illustrate a perspective view and a side view, respectively, of an example twister device.

FIGS. 11A, 11B, 11C, 11D, 11E, 11F, 11G, 11H, 11I, 11J, 11K, 11L, 11M, 11N, and 11O illustrate an example method using an example twister device to approximate two model valve leaflets disposed within a model heart.

DETAILED DESCRIPTION OF SOME EMBODIMENTS

Figure 1A:
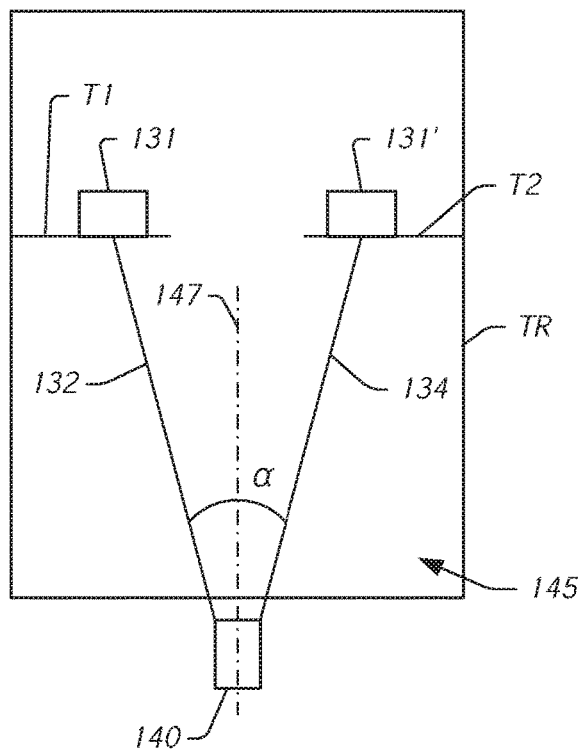
FIGS. 1A, 1B, 1C, and 1D illustrate schematically an example method and device for approximating tissues using a twister device disposed outside a target region.
Figure 1B:
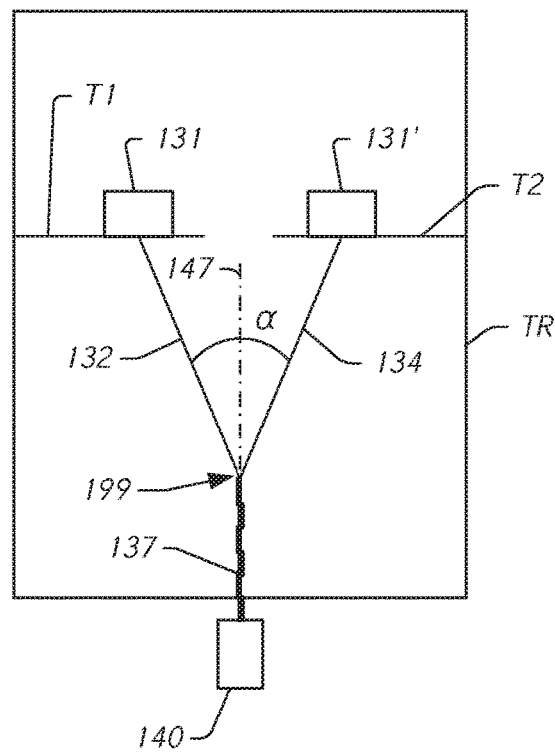
Figure 1C:
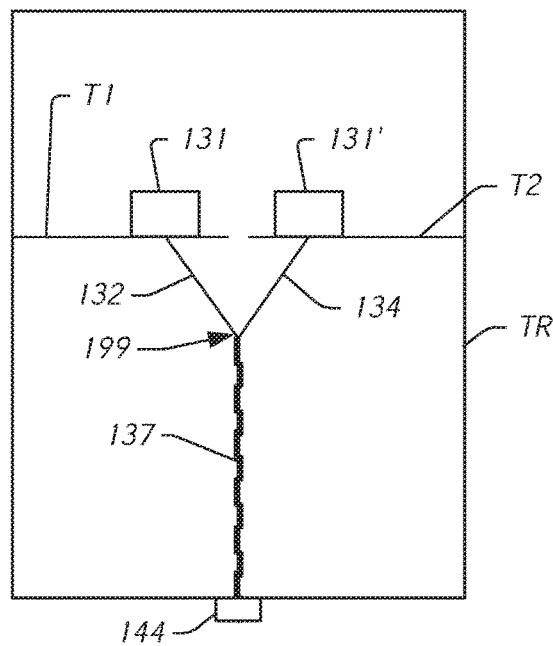

The headings provided herein, if any, are for convenience only and do not necessarily affect the scope or meaning of the claimed invention.

Overview

During conventional, on-pump cardiac operations the heart is stopped and the doctor has vision of and direct access to the internal structures of the heart. In conventional operations, doctors perform a wide range of surgical procedures on a defective valve. In degenerative mitral valve repair procedures, techniques include, for example and without limitation, various forms of resectional repair, chordal implantation, and edge-to-edge repairs. Clefts or perforations in a leaflet can be closed and occasionally the commissures of the valve sutured to minimize or eliminate MR. While some devices have been developed to replicate conventional mitral valve procedures on a beating heart (see, e.g., International Patent Application No. PCT/US2012/043761 (published as WO 2013/003228 A1) (referred to herein as "the '761 PCT Application")) there is a need to expand the "toolbox" available to doctors during these minimally invasive procedures.

The ability to remotely (e.g., from outside the heart during a cardiac valve repair) and adjustably secure two or more otherwise separate strands of suture together within a body has wide ranging applications. One application, for example, is in minimally-invasive, beating-heart, cardiac procedures. The ability to remotely secure two or more suture strands together while the heart is beating should dramatically expand the utility of the devices that have been used in cardiac operations to date.

In some embodiments, a method for repairing tissue includes inserting a delivery device, such as a delivery device described in the '761 PCT Application and/or in International Patent Application No. PCT/US2016/055170 (published as WO 2017/059426A1) (referred to herein as "the '170 PCT Application"), the entire disclosure of each of which is incorporated herein by reference, into a body and extending a distal end of the delivery device to a proximal side of the tissue. Advancement of the delivery device may be performed in conjunction with sonography or direct visualization (e.g., direct transblood visualization), and/or any other suitable remote visualization technique. With respect to cardiac procedures, for example, the delivery device may be advanced in conjunction with transesophageal (TEE) guidance or intracardiac echocardiography (ICE) guidance to facilitate and to direct the movement and proper positioning of the device for contacting the appropriate target cardiac region and/or target cardiac tissue (e.g., a valve leaflet, a valve annulus, or any other suitable cardiac tissue). Typical procedures for use of echo guidance are set forth in Suematsu, Y., *J. Thorac. Cardiovasc. Surg.* 2005; 130:1348-56 ("Suematsu"), the entire disclosure of which is incorporated herein by reference.

A piercing portion of the delivery device can be used to form an opening in the tissue, through which the distal end of the delivery device can be inserted. The delivery device can be used to form or deliver an implant (e.g., a distal anchor) to the distal side of the tissue. The delivery device can be used in this manner to deliver two or more implants to the distal side of the tissue. The implants can be delivered to a single tissue (e.g., a posterior mitral valve leaflet), or one or more implants can be delivered to a first tissue (e.g., a posterior mitral valve leaflet), and one or more other implants can be delivered to a second tissue (e.g., an anterior mitral valve leaflet, a mitral valve annulus, or any other suitable tissue) separate from the first tissue. The delivery device can then be withdrawn, and suture portions extending from the implants can extend to a location (e.g., an outside surface of the heart or other suitable organ) remote from the tissue(s). The remote suture portions can then be coupled to a device that can be operated to twist the remote suture portions together. Advantageously, using the methods and apparatus disclosed herein, introducing additional foreign objects, such as, for example, a securing device, to an area (e.g., the heart) within which the tissues are located, can be avoided. For example, in a non-invasive cardiac procedure to repair cardiac tissue(s) within the heart, the twister device can remain outside the heart and can be used to selectively and remotely secure the suture portions extending form the implants and to selectively, reversibly, and controllably approximate the tissue(s).

FIGS. 1A, 1B, 1C, and 1D illustrate schematically an example method and example device for approximating tissues T1, T2. The method uses a twister device 140 disposed outside a target region TR. As illustrated in FIG. 1A, both a suture portion 132 extending from a first implant 131 and a suture portion 134 extending from a second implant 131' can extend to a location (e.g., an outer surface of the heart) remote from the tissues T1, T2 where the suture portions 132, 134 are coupled to the twister device 140. With each suture portion 132, 134 coupled to the twister device 140 remote from the tissues T1, T2, the twister device 140 (or a portion or component of the twister device 140) can be rotated about an axis 147 that is preferably, but not necessarily, oriented between the axes of the suture portions 132, 134. In some embodiments, the axis 147 may approximately bisect the angle α defined between the axes of the suture portions 132, 134.

Rotation of the twister device 140 (or the portion or component of the twister device 140) can operate to twist, interlace, intertwine, or otherwise secure the suture portions 132, 134 together at a desirable location (e.g., within the heart) relative to the tissues T1, T2. When the suture portions 132, 134 are twisted together, they define a point of intersection 199 of the axes of the suture portions 132, 134. As the suture portions 132, 134 are further twisted together, the point of intersection 199 is moved towards the implants 131, 131' (and thus the tissues T1, T2), the lengths of the suture portions 132, 134 between the point of intersection 199 and the respective tissues T1, T2 shorten, the length of the twisted suture portion 137 proximal to the point of intersection 199 increases, and the angle α defined between the axes of the suture portions 132, 134 increases.

Figure 1D:
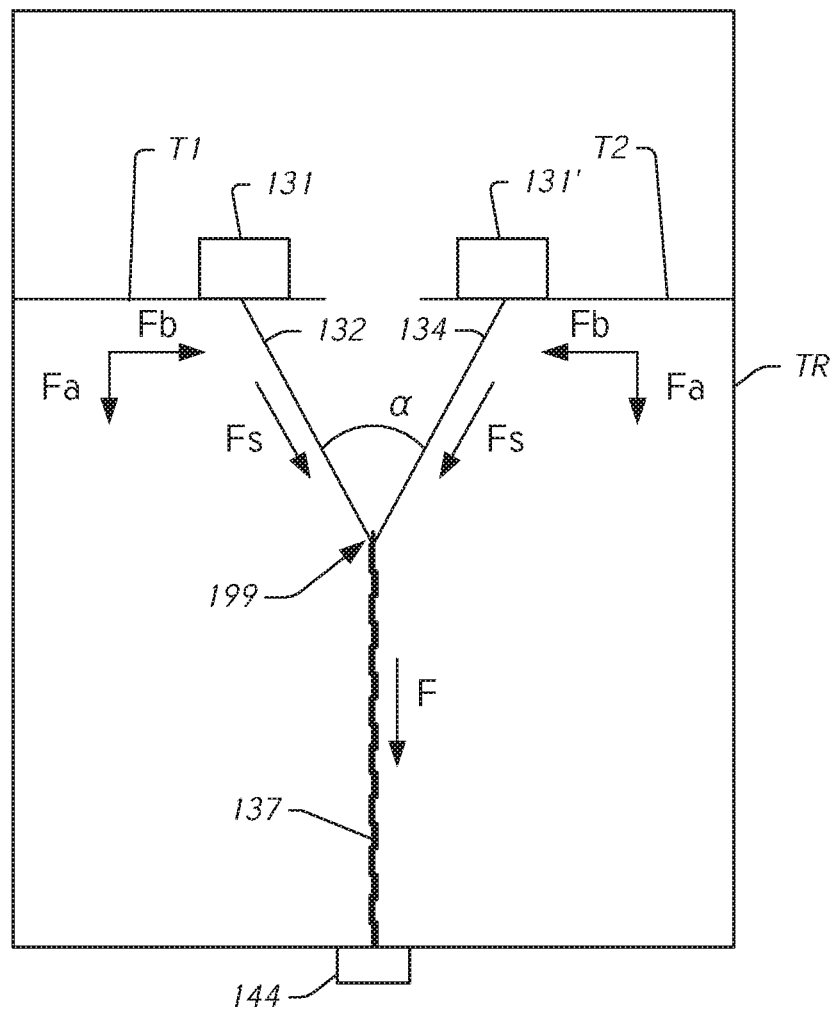

As illustrated in FIG. 1D, a force, F, applied to twisted suture portion 137 is carried to the two suture portions, and considering each suture portion as a pure tension member, an axial force, Fs, carried by each suture portion 132, 134 between the twisted portion 137 and the tissues T1, T2 is carried along the respective axes of suture portion 132, 134. Each axial force, Fs, can be decomposed into a first component, Fa, that is parallel to the axis of the twisted portion 137 and a second component, Fb, that is perpendicular to the axis of the twisted portion. The second component, Fb, of the axial force, Fs, in each suture portion 132, 134 acts to approximate, or draw together, the tissue T1, T2 to which the implants 131, 131' are coupled.

The twister device 140 can be rotated any number of times to further and suitably approximate the implants 131, 131' and the tissues T1, T2 attached thereto. For example, rotating the twister device 140 causes more of the suture portion 132 and the suture portion 134 to become interlaced, thereby increasing the length of the twisted suture portion 137 and further approximating the implants 131, 131', as illustrated schematically in FIG. 1C. Likewise, the twister device 140 can be rotated in the opposite direction to shorten the twisted suture portion 137 to reduce the approximation of the implants 131, 131'. Thus, the degree of approximation can be increased or decreased until the desired or targeted approximation is achieved. The twister device 140 can then be withdrawn from the twisted suture portion 137, and the twisted suture portion 137 can be secured outside the target region in a suitable location (e.g., an outer surface of the heart) with, for example, a proximal anchor 144.

Although the above embodiment describes a method using examples dealing with a cardiac procedure, the methods and devices described herein are readily adaptable for various types of tissue repair procedures. For ease of explanation, embodiments described herein are described with respect to repairing a cardiac mitral valve. It should be understood, however, that the devices and methods described herein can be used to repair other cardiac valves, such as a tricuspid, aortic, or pulmonic valve, or non-cardiac tissues, such as in orthopedic applications where two or more tissues are to be approximated.

In some embodiments, for example, apparatus and methods are described herein for remotely securing two or more sutures together within a non-invasive procedure to repair a cardiac valve. In some embodiments, apparatus and methods are described herein for performing a non-invasive procedure for repairing a mitral valve using an edge-to-edge stitch (also referred to as an Alfieri procedure) to secure two mitral valve leaflets together.

Figure 2:
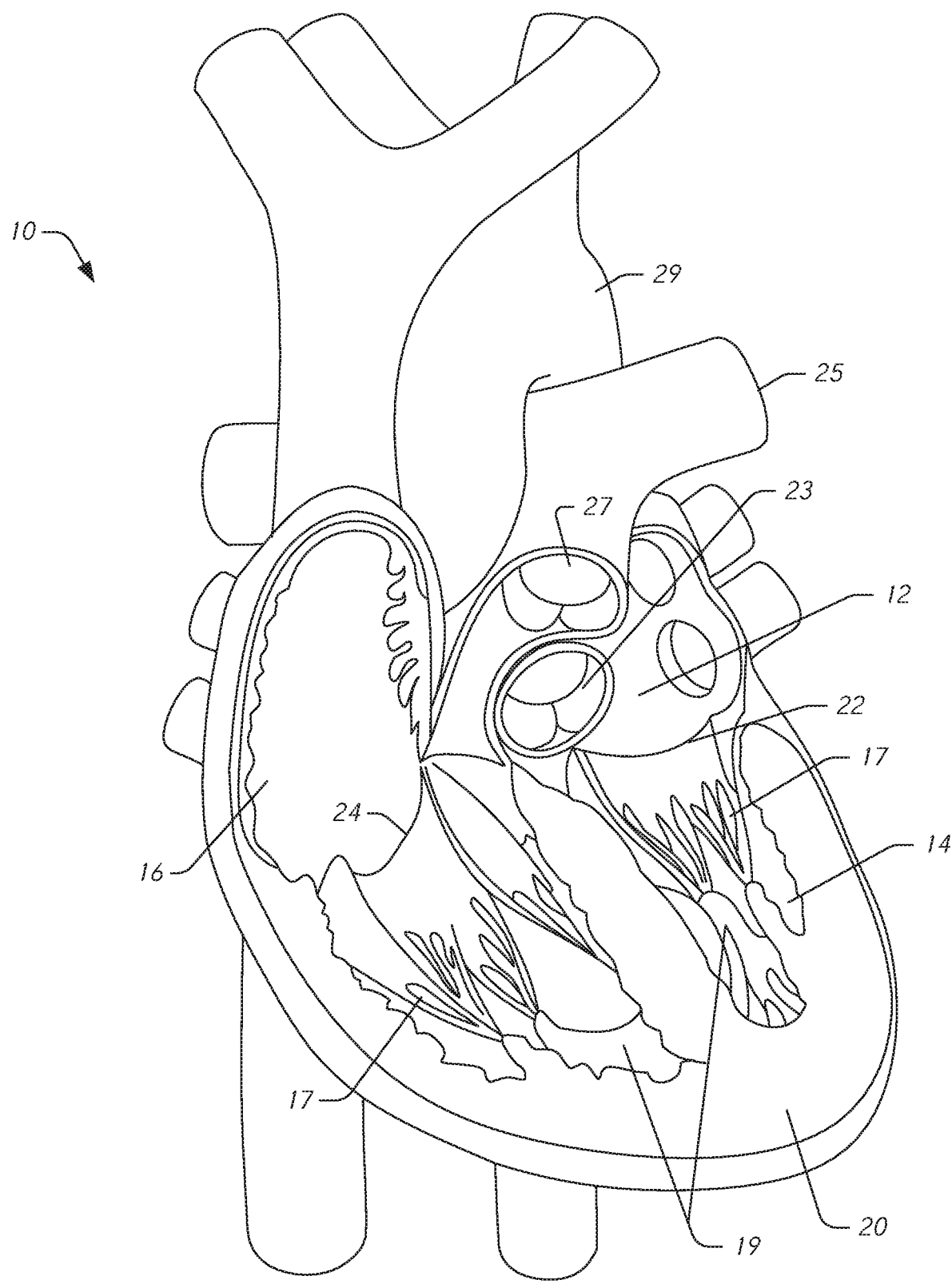
FIG. 2 illustrates a cut-away anterior view of a heart, showing the internal chambers, valves and adjacent structures.

As illustrated in FIG. 2, the human heart 10 has four chambers, which include two upper chambers denoted as atria 12, 16 and two lower chambers denoted as ventricles 14, 18. A septum 20 (see, e.g., FIG. 4) divides the heart 10 and separates the left atrium 12 and left ventricle 14 from the right atrium 16 and right ventricle 18. The heart further contains four valves 22, 23, 26, and 27. The valves function to maintain the pressure and unidirectional flow of blood through the body and to prevent blood from leaking back into a chamber from which it has been pumped.

Two valves separate the atria 12, 16 from the ventricles 14, 18, denoted as atrioventricular valves. The mitral valve 22, also known as the left atrioventricular valve, controls the passage of oxygenated blood from the left atrium 12 to the left ventricle 14. A second valve, the aortic valve 23, separates the left ventricle 14 from the aortic artery (aorta) 29, which delivers oxygenated blood via the circulation to the entire body. The aortic valve 23 and mitral valve 22 are part of the left heart, which controls the flow of oxygen-rich blood from the lungs to the body. The right atrioventricular valve, the tricuspid valve 24, controls passage of deoxygenated blood into the right ventricle 18. A fourth valve, the pulmonary valve 27, separates the right ventricle 18 from the pulmonary artery 25. The right ventricle 18 pumps deoxygenated blood through the pulmonary artery 25 to the lungs wherein the blood is oxygenated and then delivered to the left atrium 12 via the pulmonary vein. Accordingly, the tricuspid valve 24 and pulmonic valve 27 are part of the right heart, which control the flow of oxygen-depleted blood from the body to the lungs.

Both the left and right ventricles 14, 18 constitute pumping chambers. The aortic valve 23 and pulmonic valve 27 lie between a pumping chamber (ventricle) and a major artery and control the flow of blood out of the ventricles and into the circulation. The aortic valve 23 and pulmonic valve 27 have three cusps, or leaflets, that open and close and thereby function to prevent blood from leaking back into the ventricles after being ejected into the lungs or aorta 29 for circulation.

Both the left and right atria 12, 16 are receiving chambers. The mitral valve 22 and tricuspid valve 24, therefore, lie between a receiving chamber (atrium) and a ventricle to control the flow of blood from the atria to the ventricles and prevent blood from leaking back into the atrium during ejection from the ventricle. Both the mitral valve 22 and tricuspid valve 24 include two or more cusps, or leaflets (not shown in FIG. 2), that are encircled by a variably dense fibrous ring of tissues known as the annulus (not shown in FIG. 2). The valves are anchored to the walls of the ventricles by chordae tendineae (chordae) 17. The chordae tendineae 17 are cord-like tendons that connect the papillary muscles 19 to the leaflets (not shown in FIG. 2) of the mitral valve 22 and tricuspid valve 24 of the heart 10. The papillary muscles 19 are located at the base of the chordae tendineae 17 and are within the walls of the ventricles. The papillary muscles 19 do not open or close the valves of the heart, which close passively in response to pressure gradients; rather, the papillary muscles 19 brace the valves against the high pressure needed to circulate the blood throughout the body. Together, the papillary muscles 19 and the chordae tendineae 17 are known as the sub-valvular apparatus. The function of the sub-valvular apparatus is to keep the valves from prolapsing into the atria when they close.

Figure 3A:
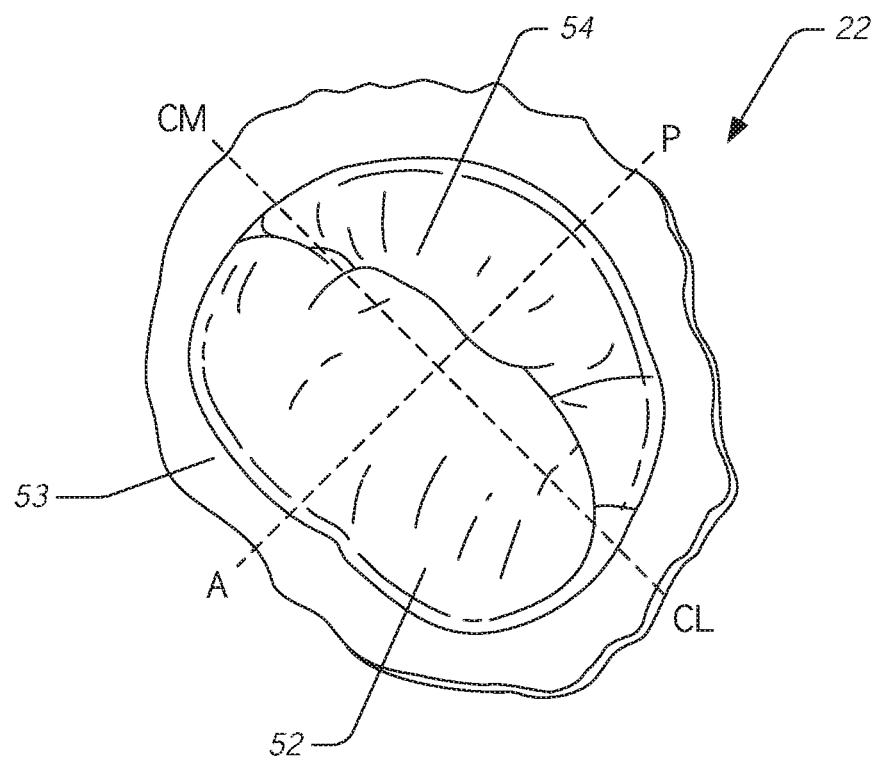
FIG. 3A illustrates a top perspective view of a healthy mitral valve with the mitral leaflets closed.

The mitral valve 22 is illustrated in FIG. 3A. The mitral valve 22 includes two leaflets, the anterior leaflet 52 and the posterior leaflet 54, and a diaphanous incomplete ring around the valve, called the annulus 53. The mitral valve 22 has two papillary muscles 19, the anteromedial and the posterolateral papillary muscles (see, e.g., FIG. 2), which attach the leaflets 52, 54 to the walls of the left ventricle 14 via the chordae tendineae 17 (see, e.g., FIG. 2).

Figure 3B:
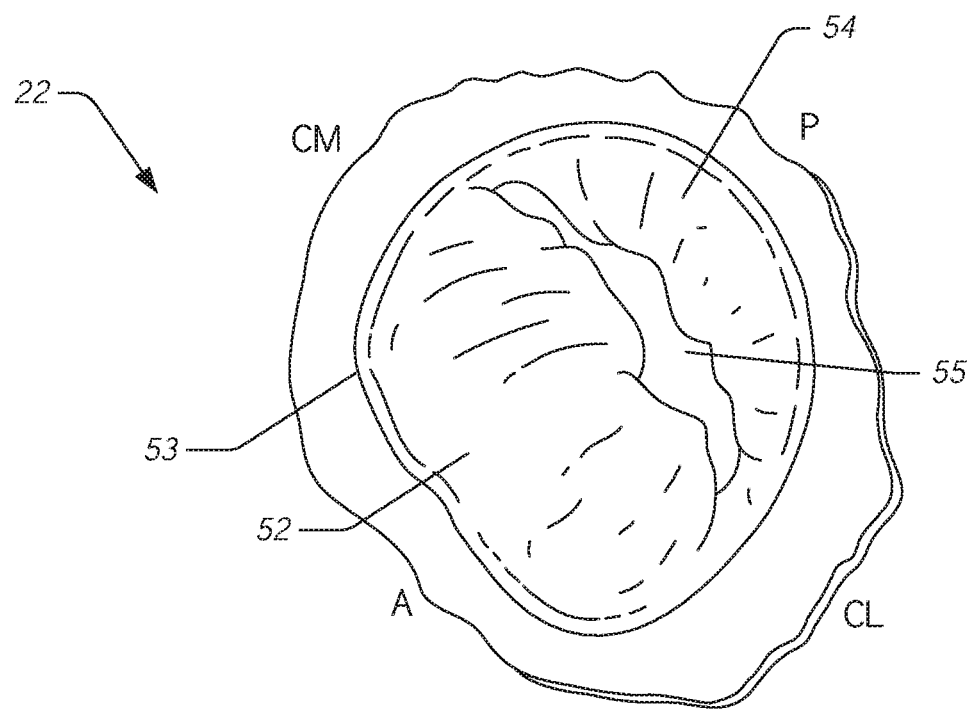
FIG. 3B illustrates a top perspective view of a dysfunctional mitral valve with a visible gap between the mitral leaflets.
Figure 3C:
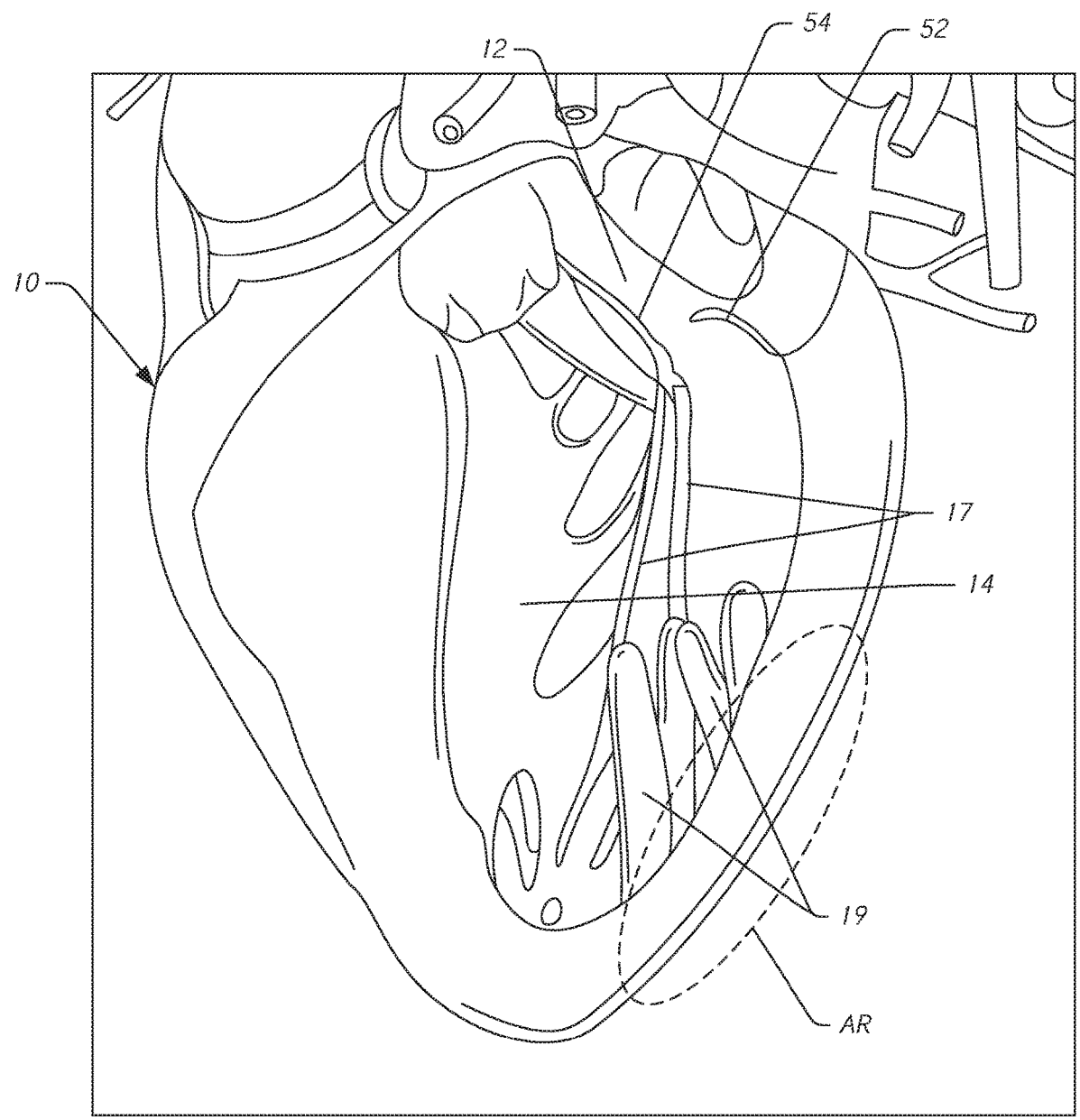
FIG. 3C illustrates a cross-sectional view of a heart illustrating a mitral valve prolapsed into the left atrium.
Figure 3D:
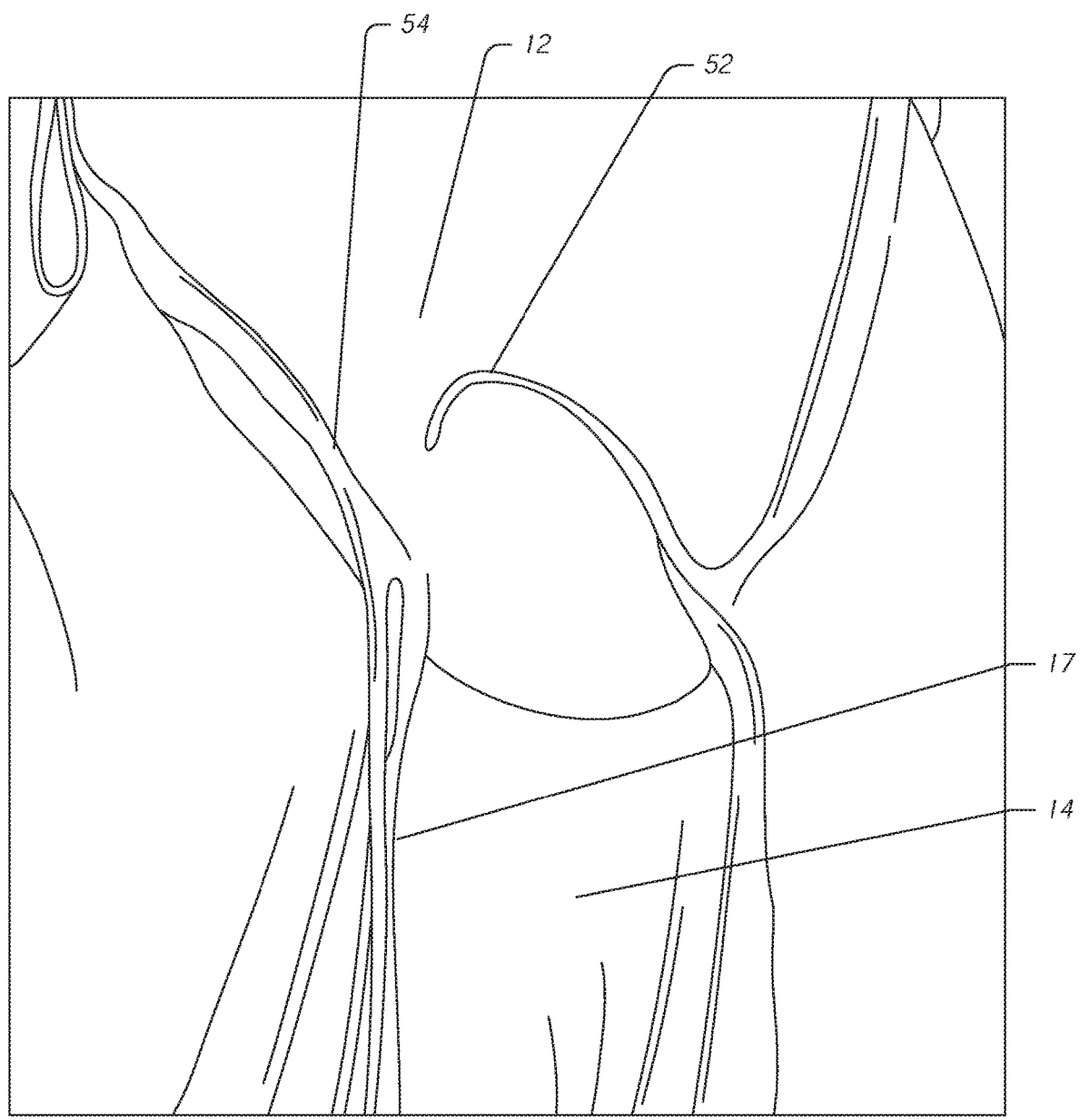
FIG. 3D illustrates an enlarged view of the prolapsed mitral valve of FIG. 3C.

FIG. 3B illustrates a prolapsed mitral valve 22. As can be seen with reference to FIGS. 3B-3D, prolapse occurs when a prolapsed segment of a leaflet 52, 54 of the mitral valve 22 is displaced above the plane of the mitral annulus into the left atrium 12 (see FIGS. 3C and 3D) preventing the leaflets from properly sealing together to form the natural plane or line of coaptation between the valve leaflets during systole. Because one or more of the leaflets 52, 54 malfunctions, the mitral valve 22 does not close properly, and, therefore, the leaflets 52, 54 fail to coapt. This failure to coapt causes a gap 55 between the leaflets 52, 54 that allows blood to flow back into the left atrium, during systole, while it is being ejected by the left ventricle. As set forth above, there are several different ways a leaflet may malfunction, which can thereby lead to regurgitation.

Mitral valve regurgitation increases the workload on the heart and may lead to very serious conditions if left untreated, such as decreased ventricular function, pulmonary hypertension, congestive heart failure, permanent heart damage, cardiac arrest, and ultimately death. Since the left heart is primarily responsible for circulating the flow of blood throughout the body, malfunction of the mitral valve 22 is particularly problematic and often life threatening.

As described in detail in the '761 PCT Application and the '170 PCT Application, methods and devices are provided for performing non-invasive procedures to repair a cardiac valve, such as a mitral valve. Such procedures include procedures to repair regurgitation that occurs when the leaflets of the mitral valve do not coapt at peak contraction pressures, resulting in an undesired back flow of blood from the ventricle into the atrium. As described in the '761 PCT Application and the '170 PCT Application, after the malfunctioning cardiac valve has been assessed and the source of the malfunction verified, a corrective procedure can be performed. Various procedures can be performed in accordance with the methods described therein to effectuate a cardiac valve repair, which will depend on the specific abnormality and the tissues involved.

After prepping and placing the subject under anesthesia, a transesophageal echocardiogram (TEE) (2D or 3D), a transthoracic echocardiogram (TTE), intracardiac echo (ICE), or cardio-optic direct visualization (e.g., via infrared vision from the tip of a 7.5 F catheter) may be performed to assess the heart and its valves.

After a minimally invasive approach is determined to be advisable, one or more incisions are made proximate to the thoracic cavity to provide a surgical field of access. The total number and length of the incisions to be made depend on the number and types of the instruments to be used as well as the procedure(s) to be performed. The incision(s) should be made in such a manner to be minimally invasive. As referred to herein, the term minimally invasive means in a manner by which an interior organ or tissue may be accessed with as little as possible damage being done to the anatomical structure through which entry is sought. Typically, a minimally invasive procedure is one that involves accessing a body cavity by a small incision of, for example, approximately 5 cm or less made in the skin of the body. The incision may be vertical, horizontal, or slightly curved. If the incision is placed along one or more ribs, it should follow the outline of the rib. The opening should extend deep enough to allow access to the thoracic cavity between the ribs or under the sternum and is preferably set close to the rib cage and/or diaphragm, dependent on the entry point chosen.

In one example method, the heart may be accessed through one or more openings made by a small incision(s) in a portion of the body proximal to the thoracic cavity, for example, between one or more of the ribs of the rib cage of a patient, proximate to the xyphoid appendage, or via the abdomen and diaphragm. Access to the thoracic cavity may be sought to allow the insertion and use of one or more thorascopic instruments, while access to the abdomen may be sought so as to allow the insertion and use of one or more laparoscopic instruments. Insertion of one or more visualizing instruments may then be followed by transdiaphragmatic access to the heart. Additionally, access to the heart may be gained by direct puncture (e.g., via an appropriately sized needle, for instance an 18-gauge needle) of the heart from the xyphoid region. Accordingly, the one or more incisions should be made in such a manner as to provide an appropriate surgical field and access site to the heart in the least invasive manner possible. Access may also be achieved using percutaneous methods further reducing the invasiveness of the procedure. See for instance, "Full-Spectrum Cardiac Surgery Through a Minimal Incision Mini-Sternotomy (Lower Half) Technique," Doty et al., *Annals of Thoracic Surgery* 1998; 65(2): 573-7 and "Transxiphoid Approach Without Median Sternotomy for the Repair of Atrial Septal Defects," Barbero-Marcial et al., *Annals of Thoracic Surgery* 1998; 65(3): 771-4, the entire disclosures of each of which are incorporated herein by reference.

Once a suitable entry point has been established, the surgeon can use one or more sutures to make a series of stiches in one or more concentric circles in the myocardium at the desired location to create a "pursestring" closure. The Seldinger technique can be used to access the left ventricle in the area surrounded by the pursestring suture by puncturing the myocardium with a small sharp hollow needle (a "trocar") with a guidewire in the lumen of the trocar. Once the ventricle has been accessed, the guidewire can be advanced, and the trocar removed. A valved-introducer with dilator extending through the lumen of the valved-introducer can be advanced over the guidewire to gain access to the left ventricle. The guidewire and dilator can be removed and the valved-introducer will maintain hemostasis, with or without a suitable delivery device inserted therein, throughout the procedure. Alternatively, the surgeon can make a small incision in the myocardium and insert the valved-introducer into the heart via the incision. Once the valved-introducer is properly placed the pursestring suture is tightened to reduce bleeding around the shaft of the valved-introducer.

A suitable device, such as a delivery device described in the '761 PCT Application and/or the '170 PCT Application, may be advanced into the body and through the valved-introducer in a manner to access the left ventricle. The advancement of the device may be performed in conjunction with sonography or direct visualization (e.g., direct transblood visualization). For example, the delivery device may be advanced in conjunction with TEE guidance or ICE to facilitate and direct the movement and proper positioning of the device for contacting the appropriate apical region of the heart. Typical procedures for use of echo guidance are set forth in Suematsu.

Figure 4:
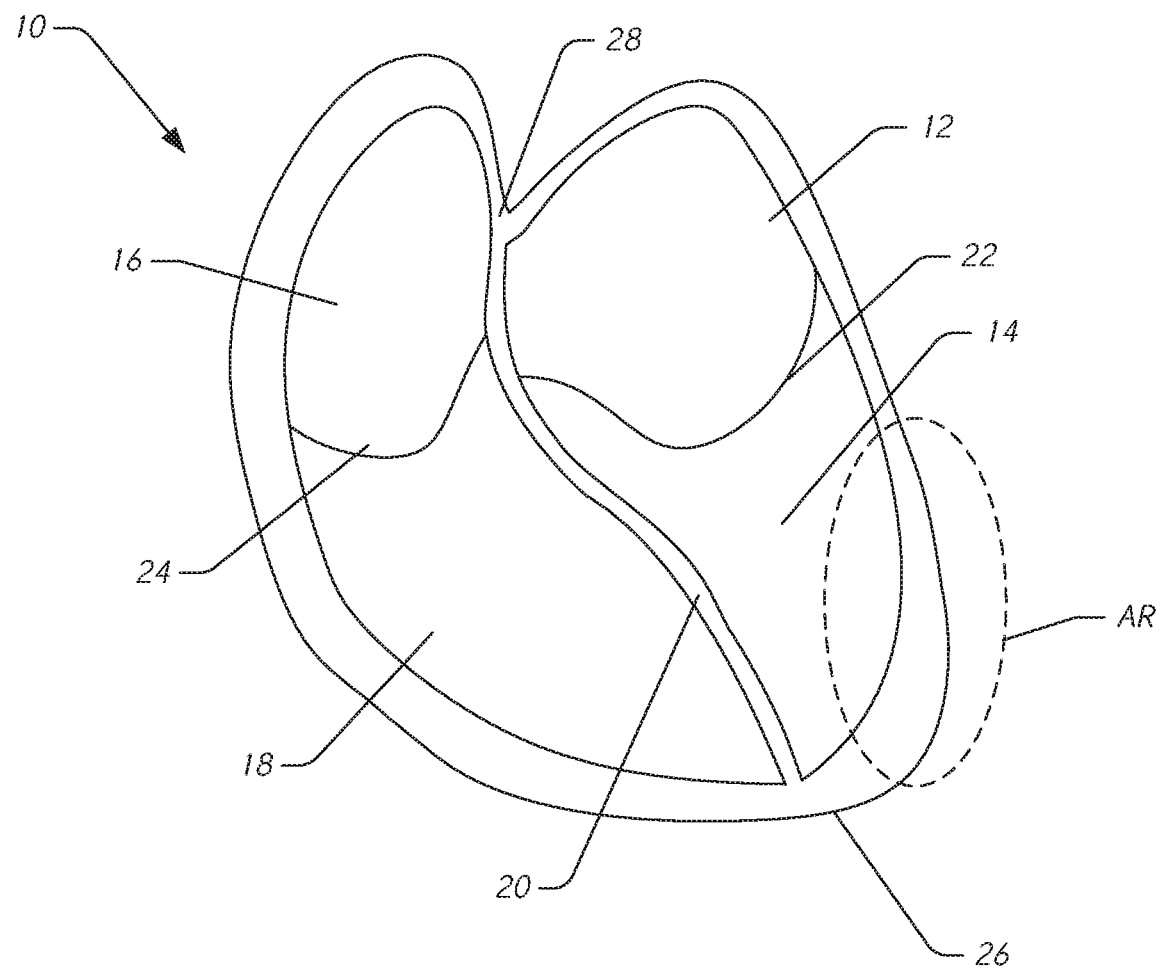
FIG. 4 illustrates a cross-sectional view of a heart showing the left atrium, right atrium, left ventricle, right ventricle and the apex region.

As shown in FIG. 4, one or more chambers, e.g., the left atrium 12, left ventricle 14, right atrium 16, or right ventricle 18 in the heart 10 may be accessed in accordance with the methods disclosed herein. Access into a chamber 12, 14, 16, 18 in the heart 10 may be made at any suitable site of entry but is preferably made in the apex region of the heart, for example, slightly above the apex 26 at the level of the papillary muscles 19 (see also FIG. 3C). Typically, access into the left ventricle 14, for instance, to perform a mitral valve repair, is gained through the process described above performed in the apical region, close to (or slightly skewed toward the left of) the median axis 28 of the heart 10. Typically, access into the right ventricle 18, for instance, to perform a tricuspid valve repair, is gained through the process described above performed in the apical region, close to or slightly skewed toward the right of the median axis 28 of the heart 10. Generally, an apex region of the heart is a bottom region of the heart that is within the left or right ventricular region and is below the mitral valve 22 and tricuspid valve 24 and toward the tip or apex 26 of the heart 10. More specifically, an apex region AR of the heart (see, e.g., FIG. 4) is within a few centimeters to the right or to the left of the septum 20 of the heart 10 at or near the level of the papillary muscles 19. Accordingly, the ventricle can be accessed directly via the apex 26, or via an off-apex location that is in the apical or apex region AR, but slightly removed from the apex 26, such as via a lateral ventricular wall, a region between the apex 26 and the base of a papillary muscle 19, or even directly at the base of a papillary muscle 19 or above. Typically, the incision made to access the appropriate ventricle of the heart is no longer than about, for example, about 0.5 cm. Alternatively, access can be obtained using the Seldinger technique described above.

The mitral valve 22 and tricuspid valve 24 can be divided into three parts: an annulus (see 53 in FIGS. 3A and 3B), leaflets (see 52, 54 in FIGS. 3A and 3B), and a sub-valvular apparatus. The sub-valvular apparatus includes the papillary muscles 19 (see FIG. 2) and the chordae tendineae 17 (see FIG. 2), which can elongate and/or rupture. If the valve is functioning properly, when closed, the free margins or edges of the leaflets come together and form a tight junction, the arc of which, in the mitral valve, is known as the line, plane or area of coaptation. Normal mitral and tricuspid valves open when the ventricles relax allowing blood from the atrium to fill the decompressed ventricle. When the ventricle contracts, chordae tendineae properly position the valve leaflets such that the increase in pressure within the ventricle causes the valve to close, thereby preventing blood from leaking into the atrium and assuring that all of the blood leaving the ventricle is ejected through the aortic valve (not shown) and pulmonic valve (not shown) into the arteries of the body. Accordingly, proper function of the valves depends on a complex interplay between the annulus, leaflets, and sub-valvular apparatus. Lesions in any of these components can cause the valve to dysfunction and thereby lead to valve regurgitation. As set forth herein, regurgitation occurs when the leaflets do not coapt properly at peak contraction pressures. As a result, an undesired back flow of blood from the ventricle into the atrium occurs.

Although the procedures described herein are with reference to repairing a cardiac mitral valve or tricuspid valve by the implantation of one or more artificial chordae, the methods presented are readily adaptable for various types of tissue, leaflet, and annular repair procedures. The methods described herein, for example, can be performed to selectively approximate two or more portions of tissue to limit a gap between the portions. In general, the methods herein are described with reference to a mitral valve 22 but should not be understood to be limited to procedures involving the mitral valve.

Example Methods for Approximating Tissues

Figure 5:
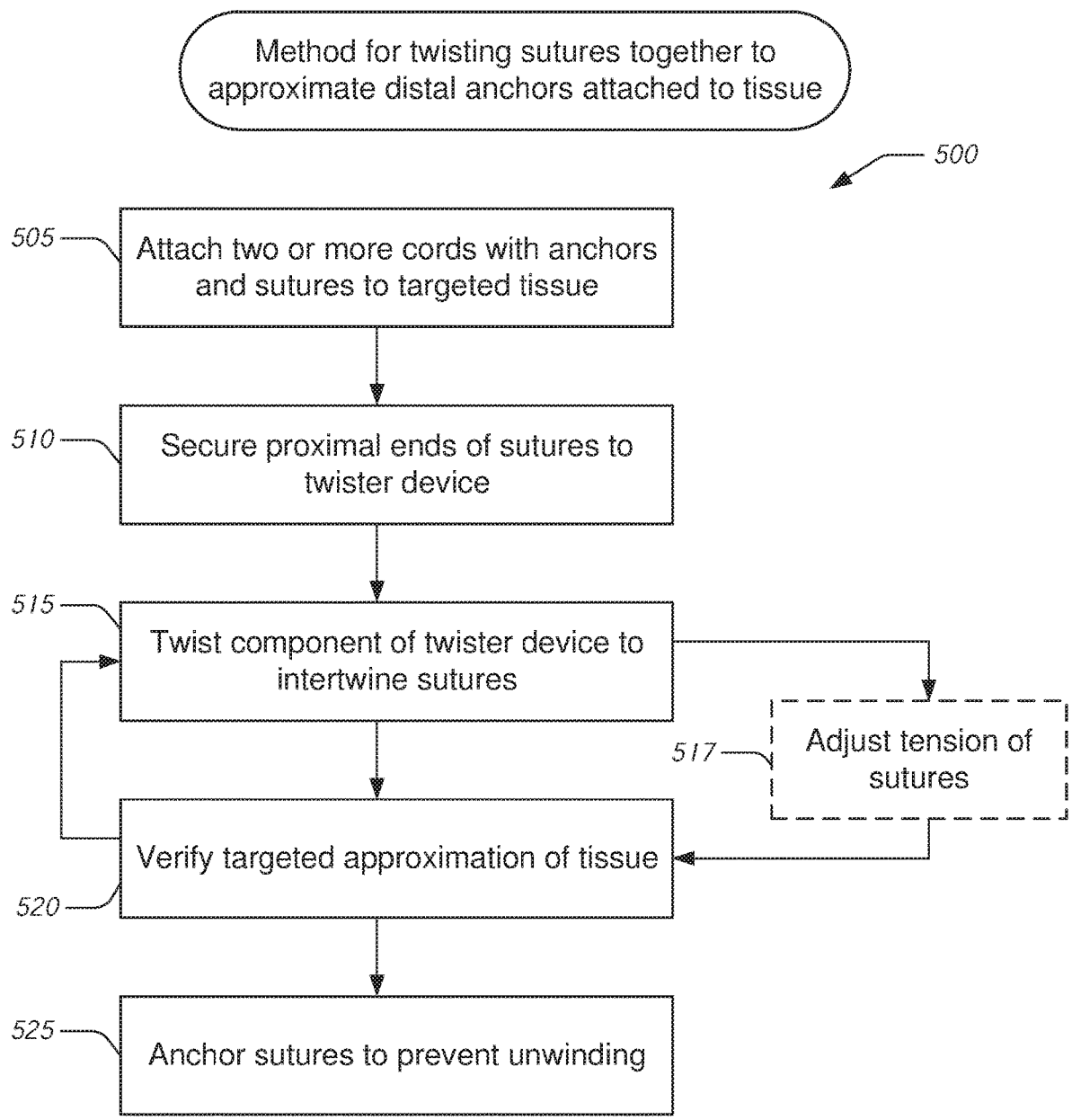
FIG. 5 illustrates an example method for twisting sutures together to approximate distal anchors attached to tissue.

FIG. 5 illustrates an example method 500 for twisting sutures together to approximate distal anchor implants attached to tissue. The method 500 can be used with any of the twister devices disclosed herein. The method 500 can be used to approximate any tissue that can receive an anchor implant (e.g., a bulky knot implant) with a suture attached thereto. Examples provided herein focus on implanting artificial tendineae, but other procedures may utilize the method 500. Where the term anchor is used herein, it is to be understood that an anchor refers to any suitable component or element that serves to anchor a suture to tissue such as, for example and without limitation, hooks, barbs, knots (e.g., bulky knots), and the like.

In some embodiments, the method 500 improves upon existing Alfieri procedures by twisting sutures to adjust the tension and direction of force vectors applied to tissues to be approximated. Advantageously, the method 500 allows an operator (e.g., a physician or surgeon) a way to change force vectors applied by anchor implants in tissue. For example, when implanting artificial tendineae, the knot that coalesces a plurality of the sutures or cords can be adjusted to be at any location from the apex of the heart to the valve with the implanted cords. This can be used to adjust both the angle of the force vectors as well as the magnitude of the force vectors, providing increased control to the operator.

At step 505, two or more artificial cords are attached to targeted tissue. The artificial cords include anchor implants at a distal end that are anchored to the targeted tissue, e.g., a posterior or anterior leaflet. The cords also include sutures extending proximally from the anchor implants. These sutures extend proximally from the implants to a region away and/or outside of the targeted region. In some embodiments, the targeted region is within the heart or within a chamber of the heart (e.g., the left ventricle).

At step 510, the proximal ends or portions of the sutures are secured to a twister device. The sutures can be secured to any portion of the twister device. In some embodiments, the sutures are releasably secured to the twister device to allow for removal of the twister device after approximation of the targeted tissue. In various embodiments, the twister device or the portion of the twister device to which the sutures are attached can be used as a pledget or other anchoring mechanism that is used to anchor the sutures after approximation of the targeted tissue. In such embodiments, the portion of the twister device to which the sutures are anchored is releasable from the main body of the twister device.

At step 515, the twister device is twisted to intertwine the sutures secured to the twister device. In some embodiments, the entire twister device is twisted to intertwine the sutures. In certain embodiments, a portion of the twister device is rotated to cause the portion of the twister device to which the sutures are secured to rotate, thereby causing the sutures to intertwine.

Twisting the twister device to intertwine or interlace the sutures causes the implants (and the tissues) to approximate. By increasing the number of twists, the targeted tissue can be approximated. Similarly, by decreasing the number of twists, the approximation of the tissues can be decreased. Thus, twisting the twister device allows an operator to control approximation of the twister devices.

In addition, twisting the twister device to intertwine or interlace the sutures causes a point of intersection of the sutures to move closer to the targeted tissues. This adjusts the angles of the forces applied to the implants, and therefore to the tissue. In addition, the portion of the sutures that are twisted together can increase in strength relative to individual sutures. This can advantageously result in stronger or more durable artificial tendineae, for example.

At optional step 517, the tension of the sutures can be adjusted. This can be done, for example, by pulling proximally on the intertwined sutures. This can be done in conjunction with the twisting of the twister device to tailor the force vectors on the implants to achieve targeted tissue approximation. For example, twisting (or untwisting) can be done simultaneously with pulling (or releasing tension) on the sutures to achieve targeted force vectors or targeted tissue approximation.

At step 520, imaging or other methods are used to verify that the targeted approximation of the tissues has been achieved. This feedback step allows the operator to iteratively adjust the number of twists applied to the sutures and/or the amount of tension on the sutures (e.g., as provided in optional step 517). The iterative nature of this portion of the method 500 is illustrated using an arrow that goes from step 520 back to step 515. Imaging methods include cardiac ultrasound and echo guidance, as described herein.

Once the targeted approximation of the targeted tissue has been achieved, the intertwined sutures are anchored at step 525. The anchoring step is done to prevent or to reduce the likelihood that the intertwined sutures will unwind. The sutures can be anchored to a tissue wall, such as an external wall of the heart. A pledget can be used as the anchor. For example, PTFE (Teflon®, Dupont, Wilmington, Del.) felt can be used as an anchor where the felt is attached to the tissue wall to prevent rotation of the sutures. In some embodiments, the anchor includes a plurality of holes through which the sutures extend so that the sutures do not unwind. Knots can be used to anchor the sutures to prevent unwinding.

In some embodiments, the sutures can be released from the anchor to allow further twisting and/or tensioning in a separate, later procedure. A new twister device or the previous twister device can be used to twist and/or tension the unanchored sutures. The sutures can then be re-anchored after the force vectors have been adjusted.

Advantageously, the twisting portion of the method 500 can be performed outside of the target region. This can allow greater accessibility and flexibility to operators performing the procedure. Another advantage of the method 500 is that it is adjustable and reversible. Because the method 500 does not require employing a clamping feature, the procedure allows for titration before anchoring of the sutures. The method 500 also allows for real-time adjustment of tissue approximation to achieve coaptation between leaflets because an operator can adjust the tension of the sutures, and by extension the approximation of the implants and targeted tissue, based on feedback from a visualization system (e.g., cardiac ultrasound).

The method 500 also provides other advantages over other approaches to addressing MR. For example, implanting a clip in the mitral valve to address MR does not provide adjustability. In contrast, the method 500 allows for real-time adjustability. Furthermore, the method 500 can be accomplished using real-time imaging or other feedback to reduce or eliminate MR. This allows an operator to see the effects of the procedure in real time allowing for the operator to make adjustments to achieve targeted results. In addition, if reoperation is required the valve is unaffected by the method 500 whereas a mitral valve clip may destroy or damage the tissue. Furthermore, a mitral valve clip is a relatively large amount of hardware to implant in the heart which may increase the risk of embolism and tissue rejection. With the method 500, the only materials implanted in the body are the sutures which present a significantly lower risk to the patient.

Example Devices for Approximating Tissues

FIGS. 6A, 6B, 6C, and 6D illustrate block diagrams of example twister devices that can be used to perform the example method of FIG. 5. It is to be understood, however, that the method 500 can be performed with any suitable device or apparatus. The twister devices described herein are merely examples of devices capable of performing the method 500.

Figure 6A:
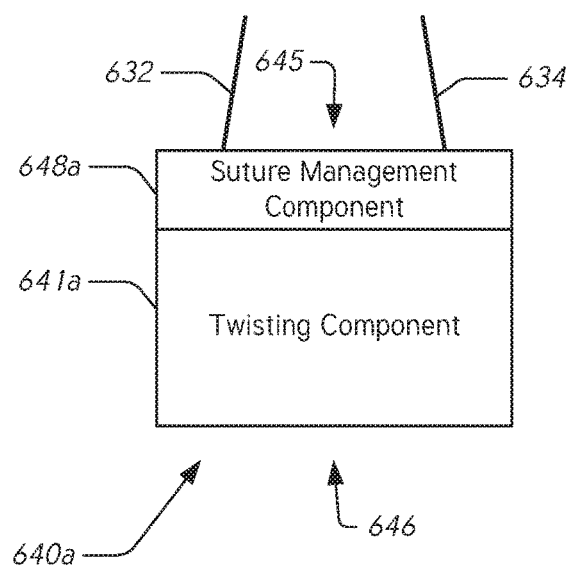
FIGS. 6A, 6B, 6C, and 6D illustrate block diagrams of example twist devices that can be used to perform the example method of FIG. 5.

FIG. 6A illustrates an example twister device 640a that includes a twisting component 641a and a suture management component 648a. The twisting component 641a is configured to cause the suture management component 648a to rotate. Thus, when suture end portions 632, 634 are attached to the suture management component 648a, the sutures become intertwined or interlaced, as described herein. In some embodiments, the twisting component 641a causes the entire twister device 640a to rotate or twist. In some embodiments, the twisting component 641a causes the suture management component 648a to rotate while other components of the twister device 640a remain stationary or do not rotate.

The twisting component 641a can be any suitable mechanical element that can cause the suture management component 648a to rotate about an axis. In some embodiments, the twisting component 641a is manually actuated by an operator (e.g., a handle that is twisted). In certain embodiments, the twisting component 641a is automatically engaged or operated (e.g., similar to a drill being operated using a button or trigger). In some embodiments, the twisting component 641a is integrally formed with the suture management component 648a so that rotation of the twisting component 641a causes rotation of the suture management component 648a. In some embodiments, the suture management component 648a is configured to rotate relative to the twisting component 641a wherein the rotation of the suture management component 648a is controlled by the twisting component 641a. The twisting component 641a can be an ergonomic fitting designed for manual manipulation by an operator.

The suture management component 648a can include one or more features to which suture end portions can be attached. As described herein, the suture management component 648a can include one or more features around which the suture end portions can be wrapped to releasably secure the suture end portions to the suture management component 648a. The suture management component 648a can include one or more such features to allow different suture end portions to be secured to different features of the suture management component 648a. In some embodiments, the suture management component 648a includes locking features that are configured to lock the suture end portions to the suture management component 648a. The purpose of the suture management component 648a is to secure the suture end portions while the twister device 640a is twisted so that the sutures become intertwined.

In some embodiments, the suture end portions 632, 634 can be attached to a distal end 645 of the twister device 640a with the twisting component 641a being at a proximal end 646 of the twister device 640a.

Figure 6B:
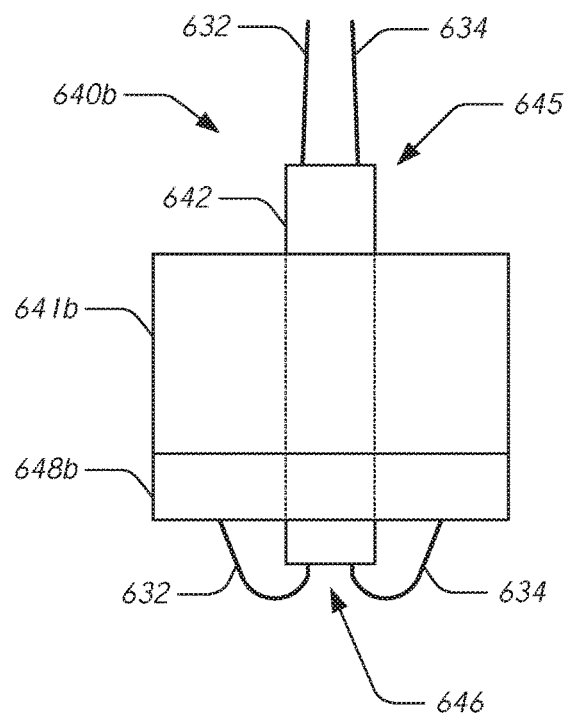

FIG. 6B illustrates another example twister device 640b that is similar to the twister device 640a of FIG. 6A. However, the twister device 640b forms an interior lumen 642 that passes from the distal end 645 to the proximal end 646 of the twister device 640b. The lumen 642 allows the suture end portions 632, 634 to pass through the twister device 640b to be secured to the suture management component 648b (which is similar in design and function to the suture management component 648a of FIG. 6A). The lumen 642 is configured to allow two or more sutures to pass through to the suture management component 648b. As with the twister device 640a of FIG. 6A, the twisting component 641b causes the suture management component 648b to rotate to intertwine the sutures. This can be accomplished in any suitable fashion, as described with reference to FIG. 6A and elsewhere herein.

Figure 6C:
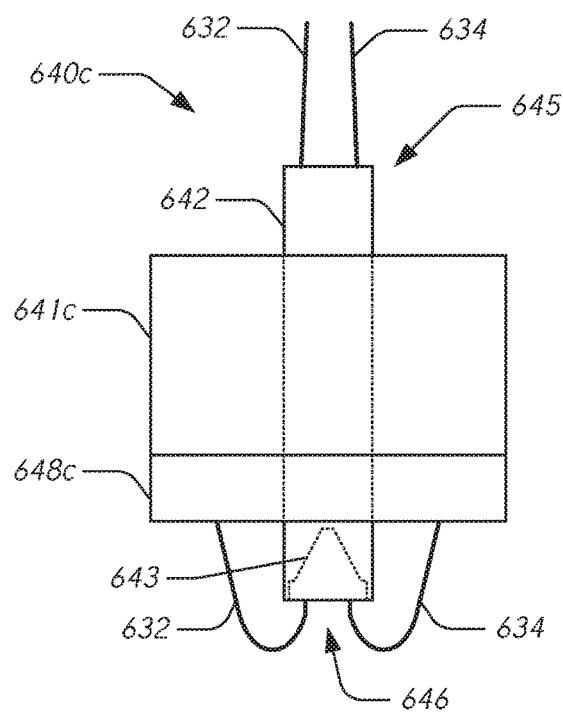

FIG. 6C illustrates another example twister device 640c that includes a valve 643 (e.g., a duckbill valve) to limit and/or to prevent undesirable backflow of blood or other bodily fluids. In all other aspects, the twister device 640c is similar to the twister device 640b of FIG. 6B.

Figure 6D:
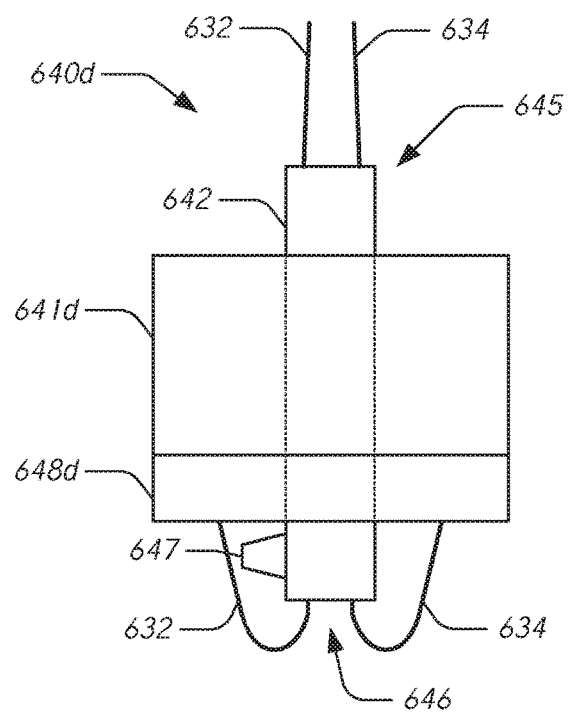

FIG. 6D illustrates another example twister device 640d that includes an access port 647 configured to receive, for example, a heparinized saline solution to limit and/or to prevent undesirable clotting during the procedure. In all other aspects, the twister device 640d is similar to the twister device 640b of FIG. 6B.

Additional Example Methods and Twister Devices

Figure 7:
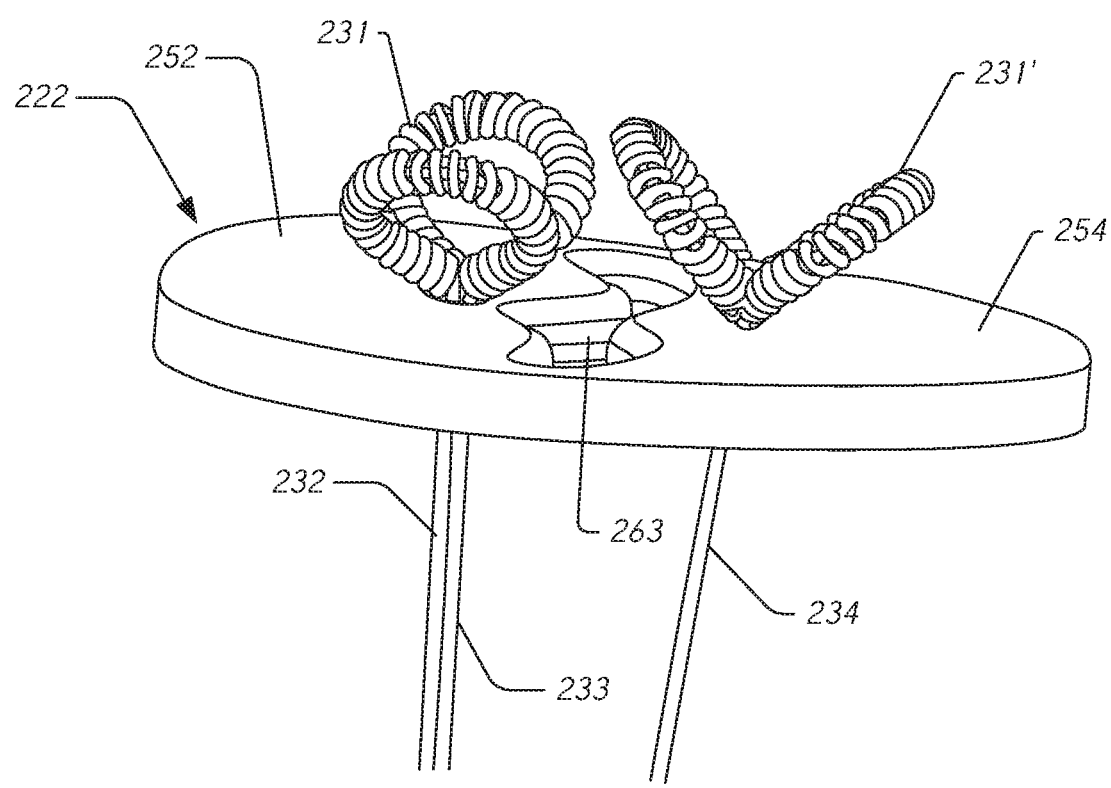
FIG. 7 illustrates a schematic illustration of a mitral valve with leaflets that are separated by a gap.

FIGS. 7, 8A, and 8B illustrate an example method and an example device for securing an artificial tendineae that has been implanted as described in the '761 PCT Application and/or the '170 PCT Application. FIG. 7 illustrates schematically a mitral valve 222 with leaflets 252, 254 that are separated by a gap 263. Two anchor implants (e.g., bulky knot implants) 231, 231' are disposed on an atrial, distal, or top side of the leaflets 252, 254, respectively. The implants 231, 231' can be formed with a suture material that forms a loop on the atrial side of the leaflets 252, 254 and extends through the leaflets 252, 254, with two loose suture end portions that extend on the ventricular, proximal, or bottom side of the leaflets 252, 254. The implant 231 has suture end portions 232 and 233, and the implant 231' has suture end portions 234 and 235 (not shown in FIG. 7).

After the implants 231, 231' are in a desired or targeted position (which can be confirmed with imaging, for example), a twister device 240 as illustrated in FIGS. 8A (perspective view) and 8B (side view with suture end portions routed therethrough) can be used during a procedure to secure the implants 231, 231' in the desired position and to secure the valve leaflets 252, 254 in an edge-to-edge relationship. Further, in addition to or instead of creating the edge-to-edge relationship, to promote a larger surface of coaptation, using the twister device 240, the implants 231, 231' can be secured together to pull or to otherwise move the posterior annulus towards the anterior leaflet and/or the anterior annulus towards the posterior leaflet to reduce the distance between the anterior annulus and the posterior annulus, e.g., the septal-lateral distance, by about 10%-40%. Approximating the anterior annulus and the posterior annulus in this manner can decrease the valve orifice, and thereby decrease, limit, or otherwise prevent undesirable regurgitation. This technique can be valuable in both degenerative MR with a prolapsed leaflet where the annulus is dilated and in functional MR where the leaflet function is normal but the annulus has dilated and there is a gap between the leaflets that can be closed by approximating the tissue.

In this embodiment, as illustrated in FIGS. 8A and 8B, the twister device 240 defines a lumen 242 from its distal end 245 to its proximal end 246, and includes tie knobs 248, 248' disposed at the proximal end 246. As described in more detail below, the suture end portions 232, 233, 234, 235 can be passed through the lumen 242 from the distal end 245 to the proximal end 246, and then tied-off, wrapped around, fixed, or otherwise secured to the tie knobs 248, 248'. If one or more of the leaflets is prolapsed, the artificial cord(s) attached to the prolapsed leaflet(s) can be tensioned before being tied-off around the knobs. Similarly stated, the tie knob 248 can be used to hold a suture portion extending from the implant 231, and the tie knob 248' can be used to hold a suture portion extending from the implant 231'. With the suture end portions 232, 233, 234, 235 secured to the respective tie knobs 248, 248', the twister device 240 can be rotated, twisted, or otherwise manipulated to intertwine the suture end portions 232, 233, 234, 235. Intertwining the suture end portions 232, 233, 234, 235 causes the two implants 231, 231' to approximate, in turn causing the leaflets 252, 254 to approximate. This can be done to secure the leaflets 252, 254 in an edge-to-edge relationship, as described in more detail herein. After the leaflets 252, 254 are secured in an edge-to-edge relationship in a desirable manner, the lengths of the suture end portions 232, 233, 234, 235 can be further adjusted until the desired length is established. The proximal end portions of the suture end portions 232, 233, 234, 235 can then be secured to an outer surface of the heart at, for example, the apex region with a proximal anchor (examples of which are described herein with reference to FIGS. 1A-1D).

FIGS. 9A-9M illustrate an example method similar to the method described above with respect to FIGS. 7, 8A, and 8B using the twister device 240 to approximate two model valve leaflets 252, 254 disposed within a model heart H. The example method illustrated in FIGS. 9A-9M uses a valved-introducer 290 to gain access to the model heart H and to deliver the implants (not shown) to the model leaflets 252, 254. With implants secured to the model leaflets 252, 254, and the suture end portions 232, 233, 234, 235 extending from the implants through the model heart H and the valved-introducer 290, extending outside the model heart H, the suture end portions 232, 233, 234, 235 can be operably coupled to the twister device 240.

Figure 9A:
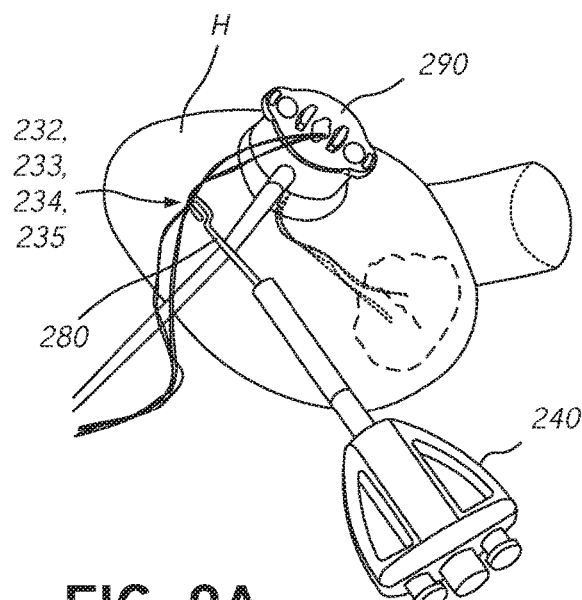
FIGS. 9A, 9B, 9C, 9D, 9E, 9F, 9G, 9H, 9I, 9J, 9K, 9L, and 9M illustrate an example method using an example twister device to approximate two model valve leaflets disposed within a model heart.
Figure 9B:
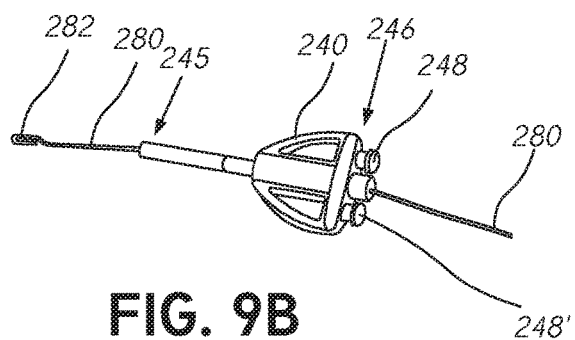
Figure 9C:
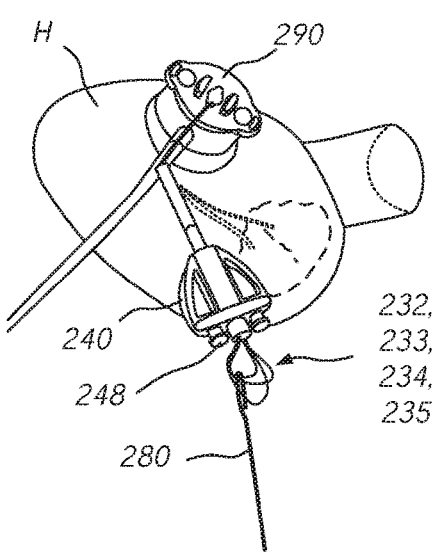
Figure 9D:
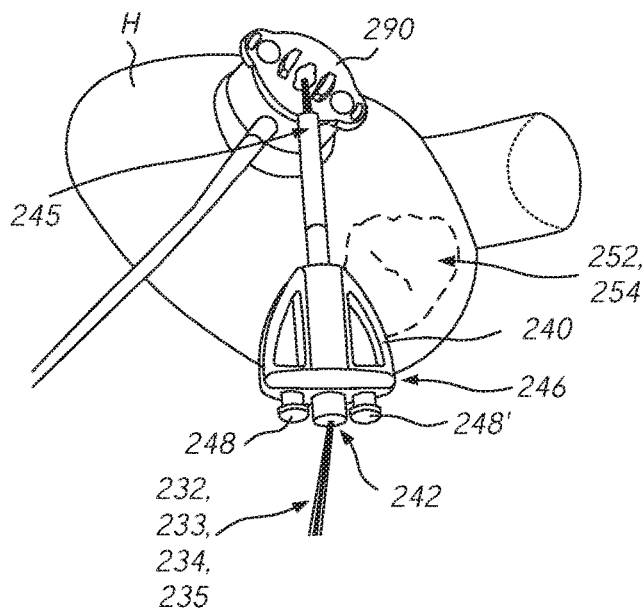
Figure 9E:
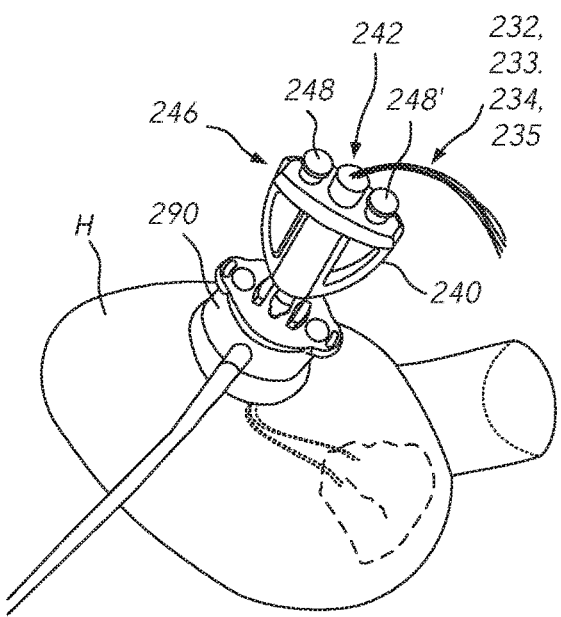
Figure 9F:
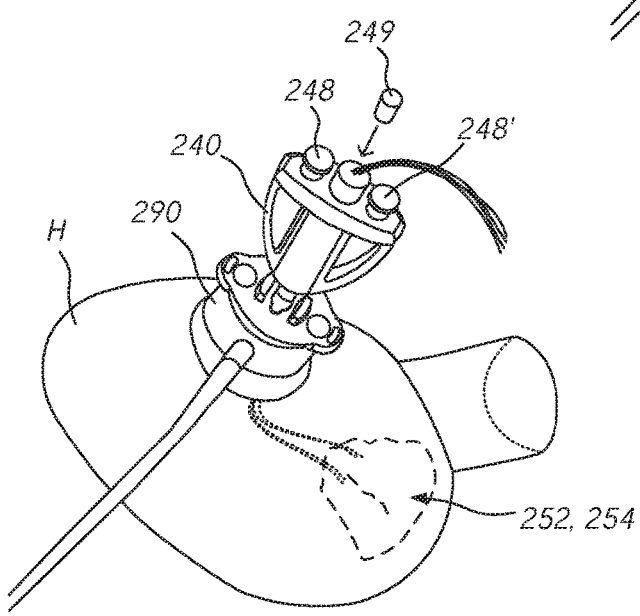
Figure 9G:
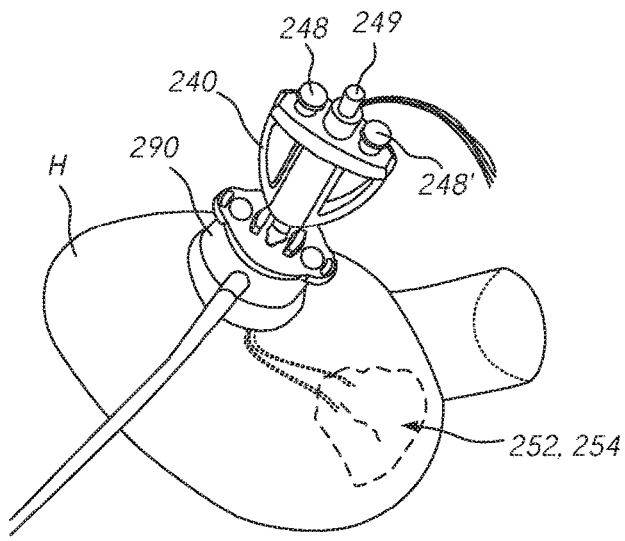
Figure 9H:
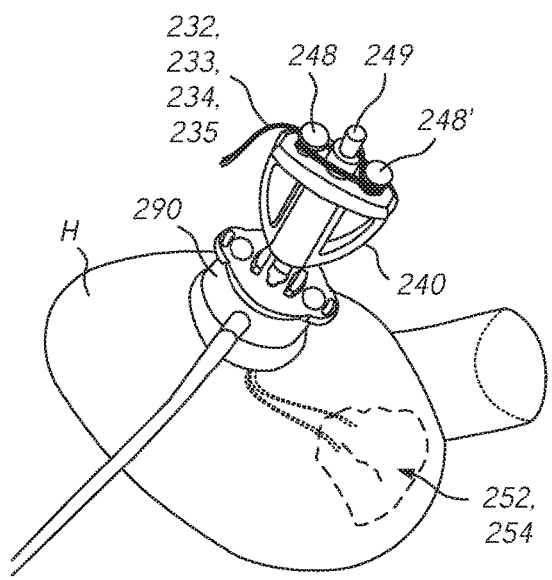

To operably couple the suture end portions 232, 233, 234, 235 to the twister device 240, a snare or threader 280 can be used to thread the suture end portions 232, 233, 234, 235 through the lumen 242 of the twister device 240. As illustrated in FIG. 9B, the threader 280 can be inserted through the lumen 242 of the twister device 240. The threader 280 defines a terminal end 282 (see, e.g., FIG. 9B) configured to be coupled to the suture end portions 232, 233, 234, 235, as illustrated in FIG. 9A. With the suture end portions 232, 233, 234, 235 extending outside the model heart H from the valved-introducer 290 and coupled to the terminal end 282 of the threader 280, the suture end portions 232, 233, 234, 235 can be threaded through the lumen 242 of the twister device 240 from its distal end 245 to its proximal end 246, as illustrated in FIG. 9C. The distal end 245 of the twister device 240 can then be inserted into the valved-introducer 290, as illustrated in FIG. 9D. With the distal end 245 of the twister device 240 inserted into the valved-introducer 290, the suture end portions 232, 233, 234, 235 can be pulled proximally and a vascular cap or boot 249 can be used to plug the lumen 242 of the twister device 240 at its proximal end 246, as illustrated in FIGS. 9E-9G. The cap 249 can be used to limit and/or to prevent an undesirable backflow of blood. Alternatively, a valve (e.g., a hemostatic valve) can be positioned within the lumen 242 of the twister device 240 to reduce, minimize, or eliminate blood loss, examples of which are described herein. As illustrated in FIG. 9H, the suture end portions 232, 233, 234, 235 can then be secured to the twister device 240 by, for example, wrapping the suture end portions 232, 233, 234, 235 around the tie knobs 248, 248'.

Figure 9I:
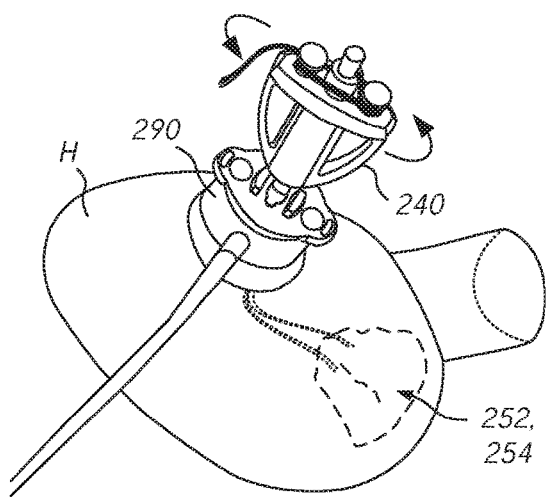
Figure 9J:
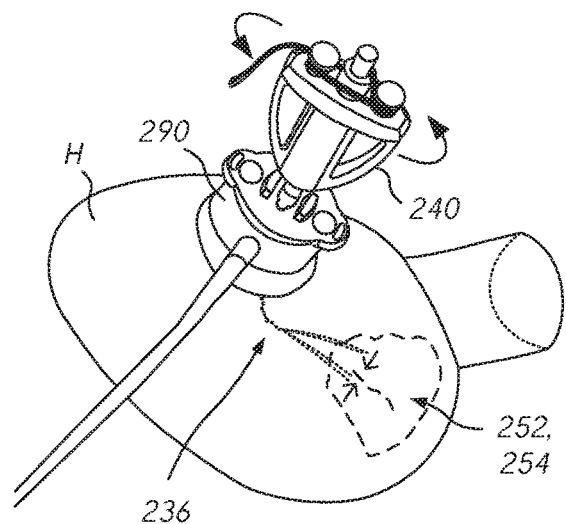
Figure 9K:
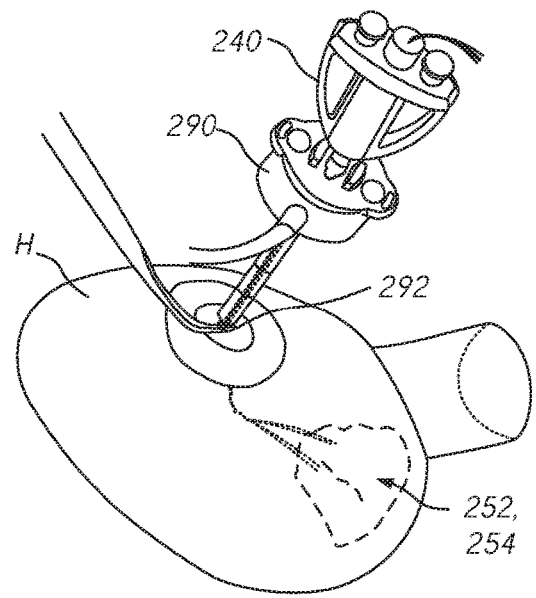

With the suture end portions 232, 233, 234, 235 fixedly coupled to the twister device 240, the twister device 240 can be rotated to twist, intertwine, and/or interlace a portion 236 of the suture end portions 232, 233, 234, 235 within the model heart H to approximate the implants and, consequently, the valve leaflets 252, 254 to which the implants are anchored, as illustrated in FIGS. 9I and 9J. Controlling the number of turns or twists of the twister device 240 allows the user to precisely approximate the valve leaflets 252, 254. Control of the approximation can be aided using, for example, echo guidance, which can be used to determine in real time with a beating heart a targeted reduction or elimination of mitral valve regurgitation. The twisting can be performed by hand or using an automated device to rotate the twister device 240. The appropriate amount of twisting can be determined visually using echo guidance, by determining an appropriate number of twists, by measuring the force required to rotate the twister device 240, or any other suitable method. Once the desired or targeted result (e.g., a suitable reduction in mitral valve regurgitation) is achieved (e.g., confirmed by remote visualization), the suture end portions 232, 233, 234, 235 can be released from the tie knobs 248, 248' of the twister device 240. Then the valved-introducer 290 and the twister device 240 can be slidably withdrawn along the suture end portion 232, 233, 234, 235, leaving the suture end portions 232, 233, 234, 235 extending from the model heart H through which the valved-introducer 290 was previously disposed, as illustrated in FIG. 9K.

Figure 9L:
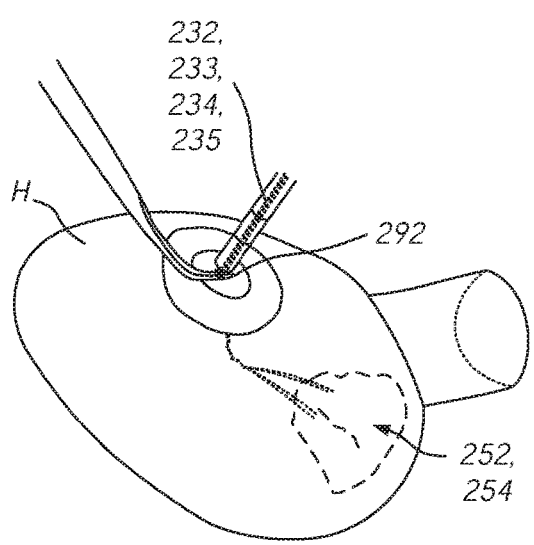
Figure 9M:
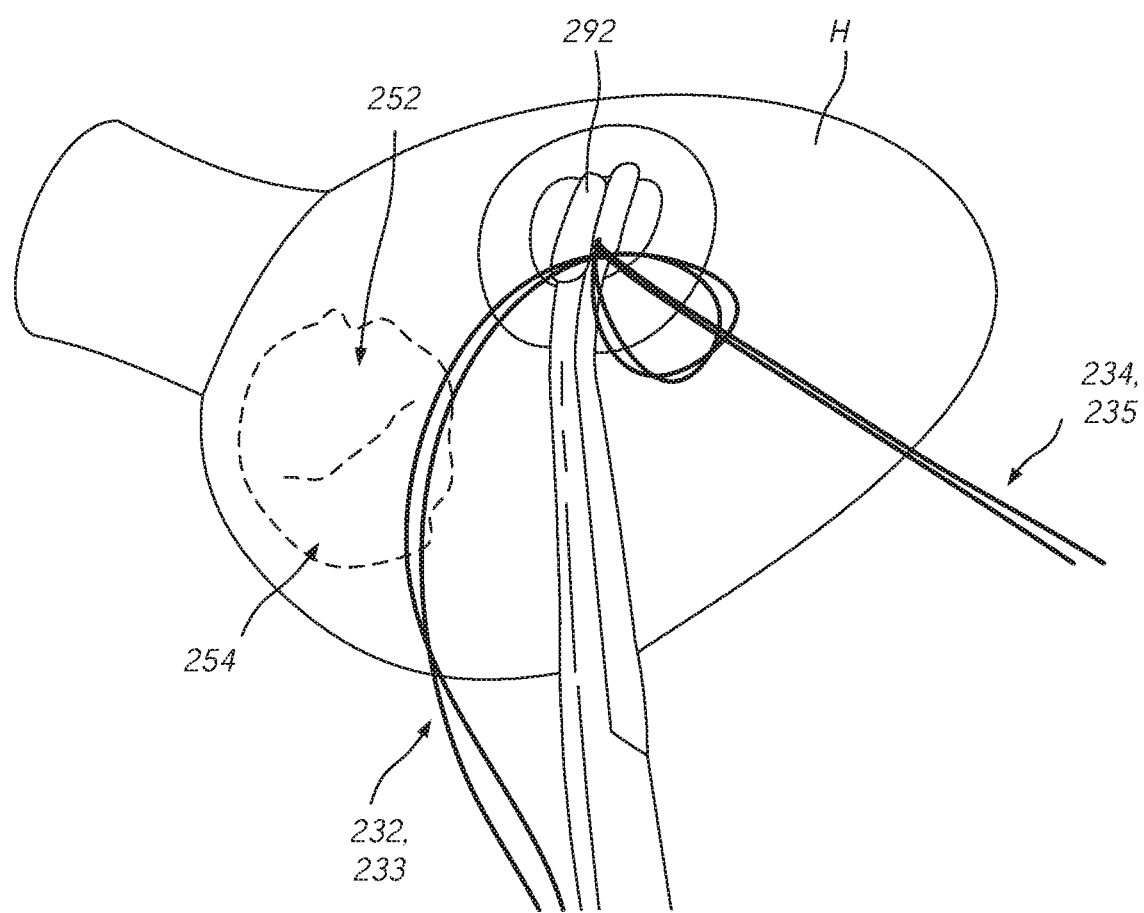

To prevent undesirable unwinding of the intertwined suture pairs during removal of the valved-introducer 290 and the twister device 240, a clamp 292 can be used to clamp suture end portions 232, 233, 234, 235, as illustrated in FIG. 9L. The suture end portions 232, 233, 234, 235 can then be anchored outside the apex of the ventricle by tying knots, using a pledget, or any other suitable anchoring mechanism, as illustrated in FIG. 9M.

FIGS. 10A-10J illustrate an example method and an example device for securing artificial tendineae that has been implanted as described in the '761 PCT Application and/or the '170 PCT Application. Similar to the method and device described with respect to FIG. 7, two implants 331, 331' can be delivered and disposed on an atrial, distal, or top side of leaflets 352, 254, respectively. The implants 331, 331' can be formed with a suture material that forms a loop on the atrial side of the leaflets 352, 354 and extends through the leaflets 352, 354, with two loose suture end portions that extend on the ventricular, proximal, or bottom side of the leaflets 352, 354. The implant 331 has suture end portions 332 and 333, and the implant 331' has suture end portions 334 and 335. In some embodiments, implants can be formed separate from the suture end portions and then attached thereto. In this manner, the implants can be attached to the suture material, deployed on the atrial side of the leaflets, and the suture end portions can extend from the implants and through the leaflets to the ventricular side of the leaflets, and then anchored outside the heart H as described in further detail herein.

Figure 10A:
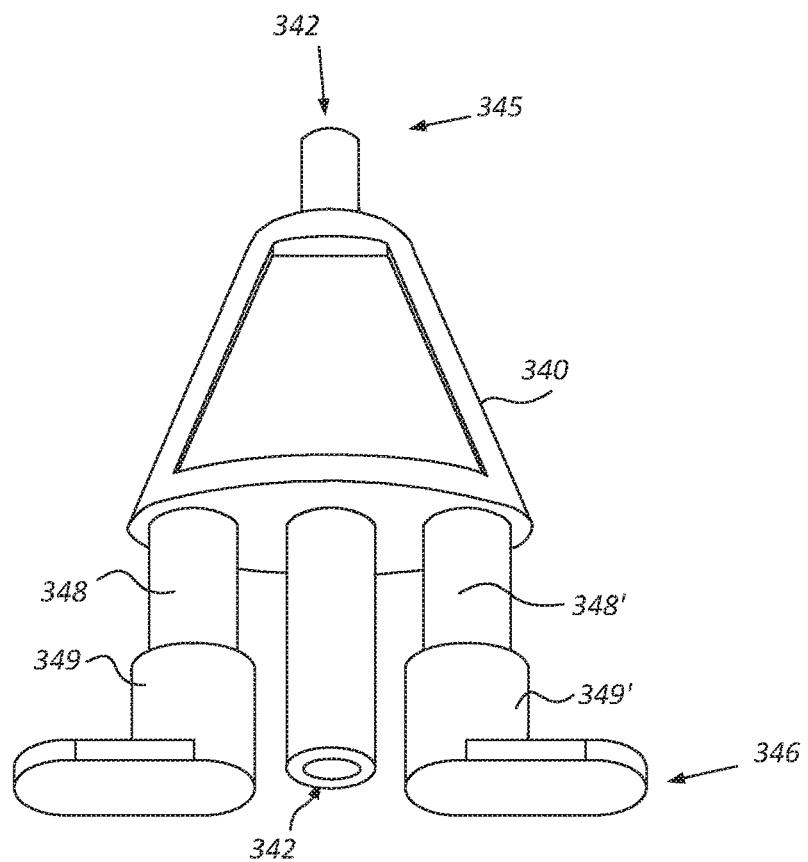
FIGS. 10A, 10B, 10C, 10D, 10E, 10F, 10G, 10H, 10I, 10J, and 10K illustrate an example method using an example twister device to approximate two model valve leaflets disposed within a model heart.
Figure 10B:
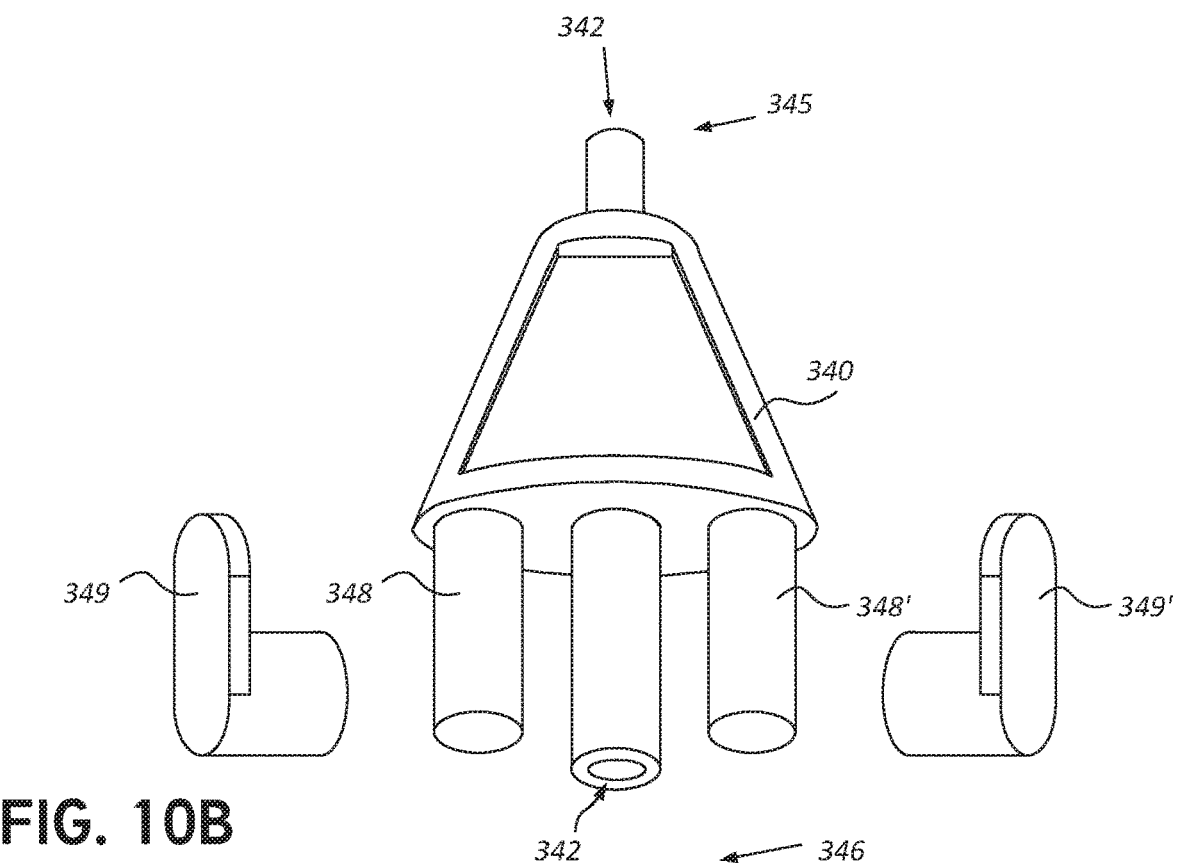

After the implants 331, 331' are in a desired or targeted position (which can be confirmed using imaging, for example), a twister device 340 as illustrated in FIGS. 10A and 10B can be used during a procedure to secure the implants 331, 331' in the desired position and to secure the valve leaflets 352, 354 in an edge-to-edge relationship. For example, using the twister device 340, the implants 331, 331' can be secured together to decrease the septal-lateral distance of the mitral valve annulus.

As illustrated in FIGS. 10A and 10B, the twister device 340 defines a lumen 342 from its distal end 345 to its proximal end 346. The twister device 340 includes tie knobs 348, 348' disposed at the proximal end 346. The twister device 340 further includes suture locks 349, 349' configured to releasably engage with the tie knobs 348, 348', respectively, to secure the suture end portions 332, 333, 334, 335 to the tie knobs 348, 348'. Although not shown, the twister device 340 further includes a valve (e.g., a duckbill valve) configured to limit and/or to prevent undesirably backflow of blood or other bodily fluids. In some instances, the twister device 340 can further include an access port configured to receive, for example, a heparinized saline to limit and/or prevent undesirable clotting during the procedure.

As described in more detail herein, the suture end portions 332, 333, 334, 335 can be passed through the lumen 342 from the distal end 345 to the proximal end 346, and then tied-off, wrapped around, fixed, or otherwise secured to the tie knobs 348, 348'. In some embodiments, the tie knob 348 can be used to hold a suture portion extending from the implant 331, and the tie knob 348' can be used to hold a suture portion extending from the implant 331'. With the suture end portions 332, 333, 334, 335 secured to the respective tie knobs 348, 348', and the suture locks 349, 349' disposed in an engaged position with the tie knobs 348, 348', respectively, the twister device 340 can be rotated, twisted, or otherwise manipulated to approximate the two implants 331, 331' and in turn the leaflets 352, 354, to secure the leaflets 352, 354 in the edge-to-edge relationship, as described in more detail herein. After the leaflets 352, 354 are secured in an edge-to-edge relationship in a desirable manner, the lengths of the suture end portions 332, 333, 334, 335 can be adjusted until the desired length is established. The proximal end portions of the suture end portions 332, 333, 334, 335 can then be secured to an outer surface of the heart H at, for example, the apex region, Ap, with a proximal anchor.

Figure 10C:
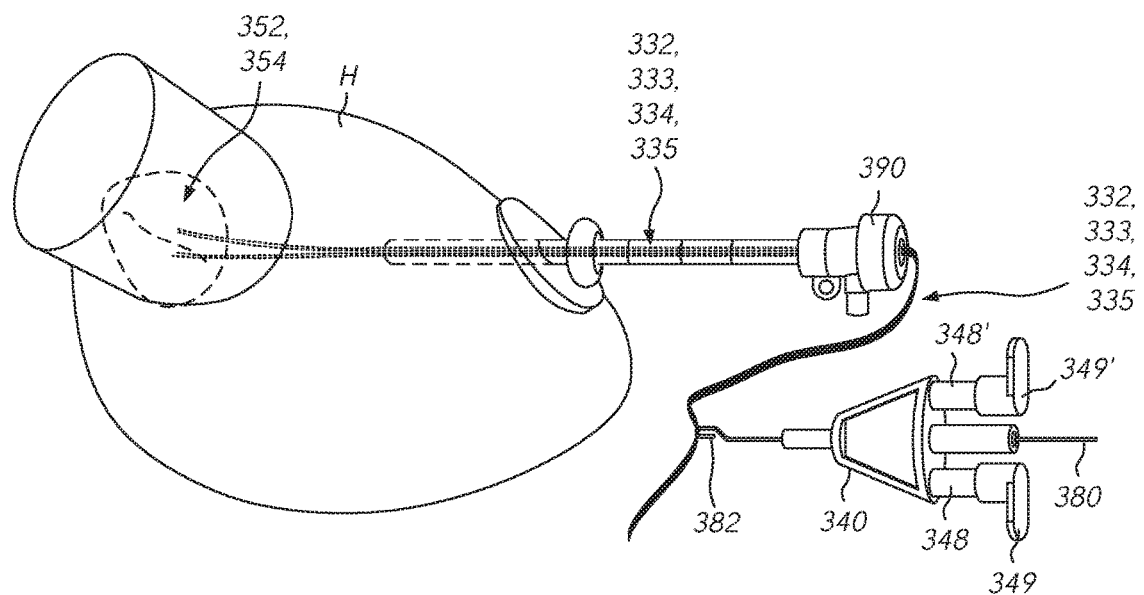

FIGS. 10C-10J illustrate a method using the twister device 340 to approximate two model valve leaflets 352, 354 disposed within a model heart H. As illustrated in FIG. 10C using the model heart H, a valved-introducer 390 is used to gain access to the model heart H and to deliver the implants 331, 331' (illustrated in FIG. 10K) to the model leaflets 352, 354. With the implants 331, 331' secured to the model leaflets 352, 355, and the suture end portions 332, 333, 334, 335 extending from the implants 331, 331' through the model heart and the valved-introducer 390, and outside the model heart H, the suture end portions 332, 333, 334, 335 can be operably coupled to the twister device 340.

Figure 10D:
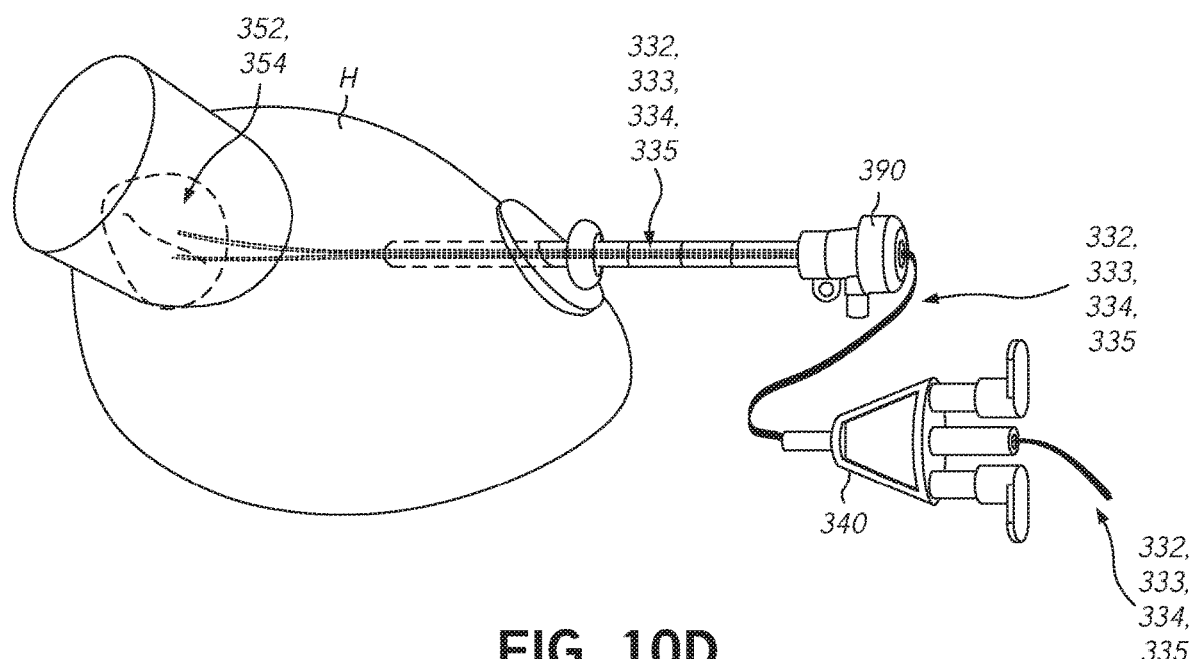
Figure 10E:
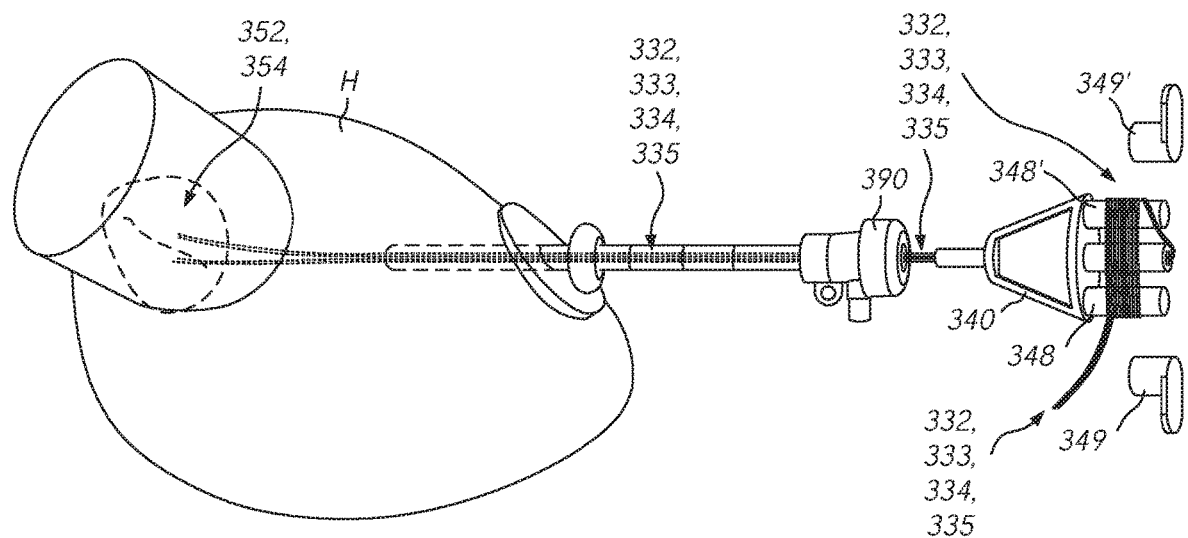
Figure 10F:
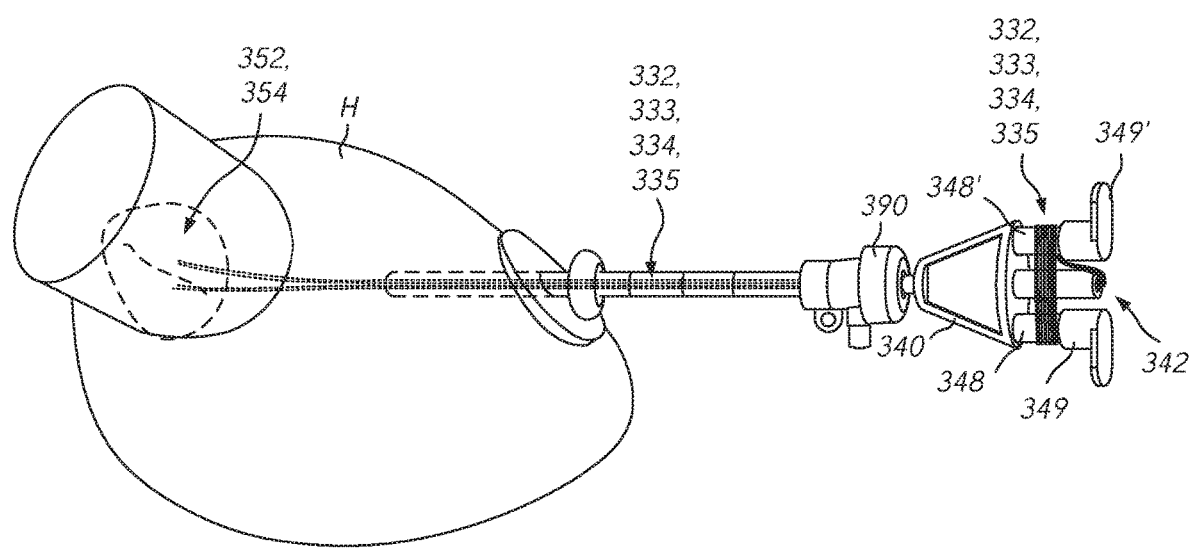

To operably couple the suture end portions 332, 333, 334, 335 to the twister device 340, a threader or snare 380 can be used to thread the suture end portions 332, 333, 334, 335 through the lumen 342 of the twister device 340. The threader 380 can be inserted through the lumen 342 of the twister device 340. The threader 380 defines a terminal end 382 configured to be coupled to the suture end portions 332, 333, 334, 335. With the suture end portions 332, 333, 334, 335 extending outside the model heart H from the valved-introducer 390 and coupled to the terminal end 382 of the threader 380, the suture end portions 332, 333, 334, 335 can be threaded through the lumen 342 of the twister 380 from its distal end 345 to its proximal end 346, as illustrated in FIG. 10D. As illustrated in FIG. 10E, the suture end portions 332, 333, 334, 335 can then be secured to the twister device 340 by, for example, wrapping the suture end portions 332, 333, 334, 335 around the tie knobs 348, 348'. With the suture end portions 332, 333, 334, 335 coupled to the tie knobs 348, 348', the suture locks 349, 349' can be moved to their respective locked positions, as illustrated in FIG. 10F, in which each suture lock 349, 349' engages with a respective tie knob 348, 348' to secure the suture end portions 332, 333, 334, 335 to the tie knobs 348, 348'. The distal end 345 of the twister device 340 can then be inserted into the valved-introducer 390, as illustrated in FIG. 10F.

Figure 10G:
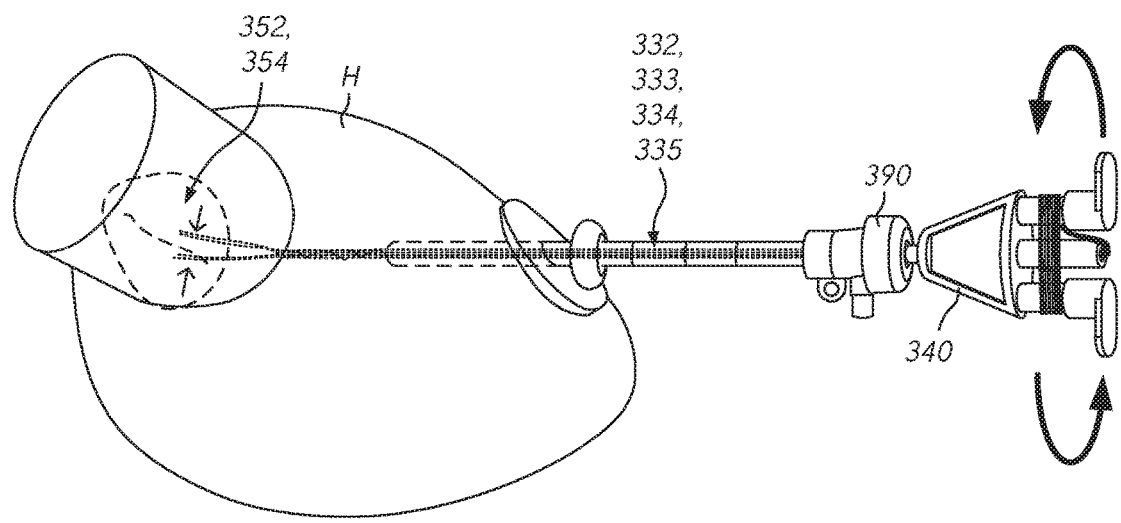
Figure 10H:
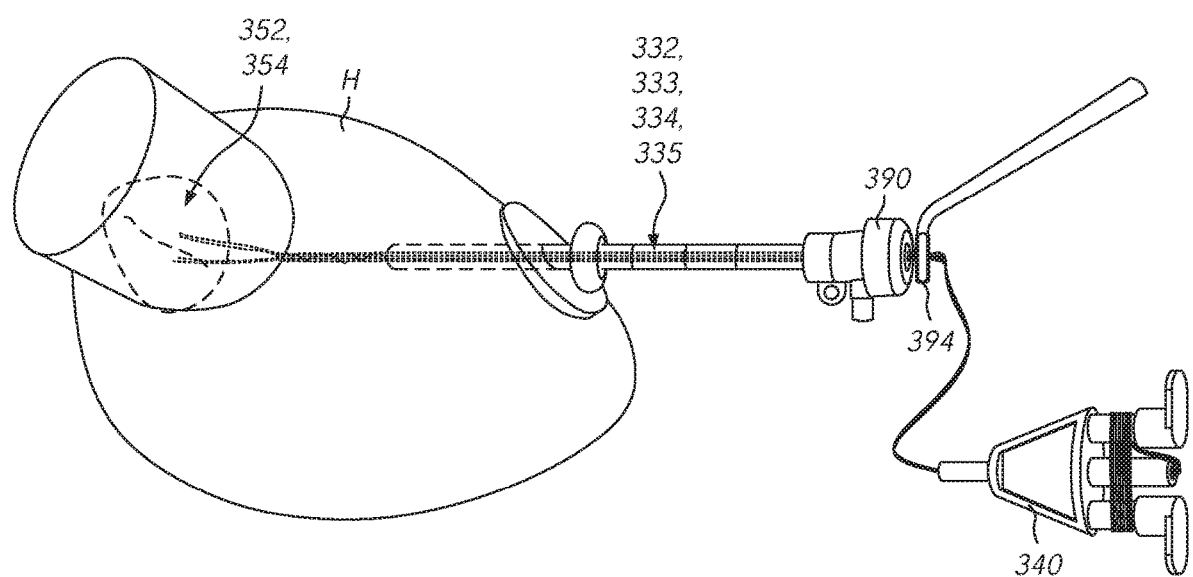
Figure 10I:
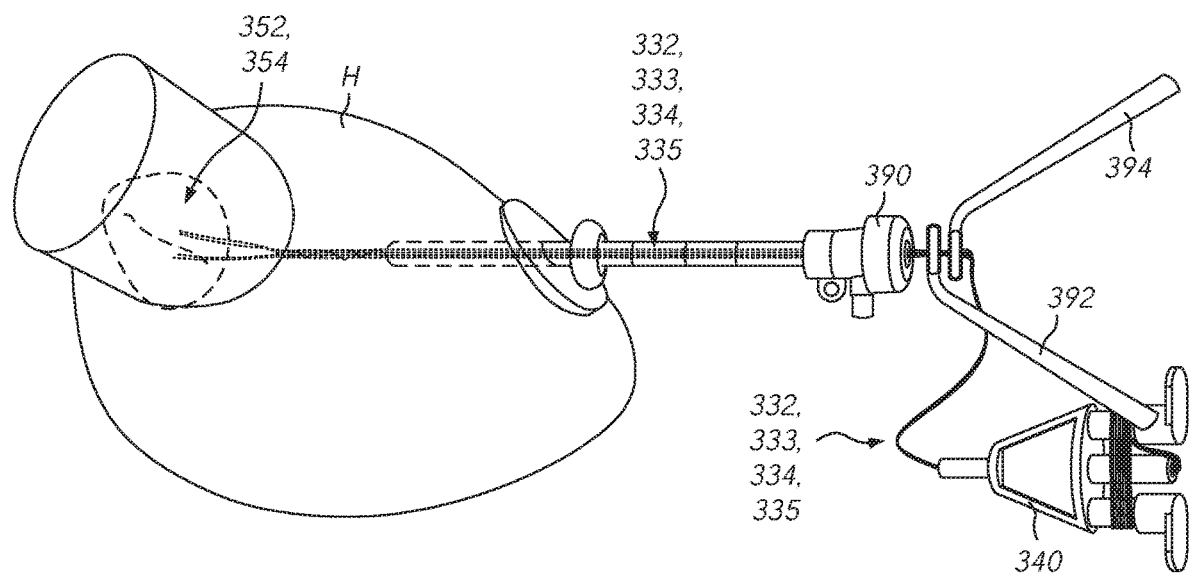
Figure 10J:
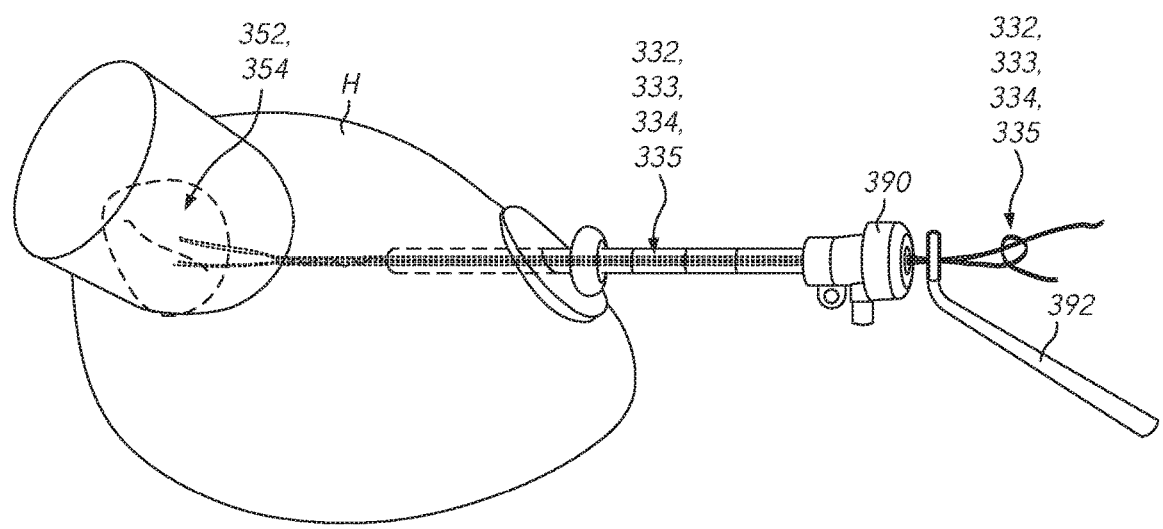
Figure 10K:
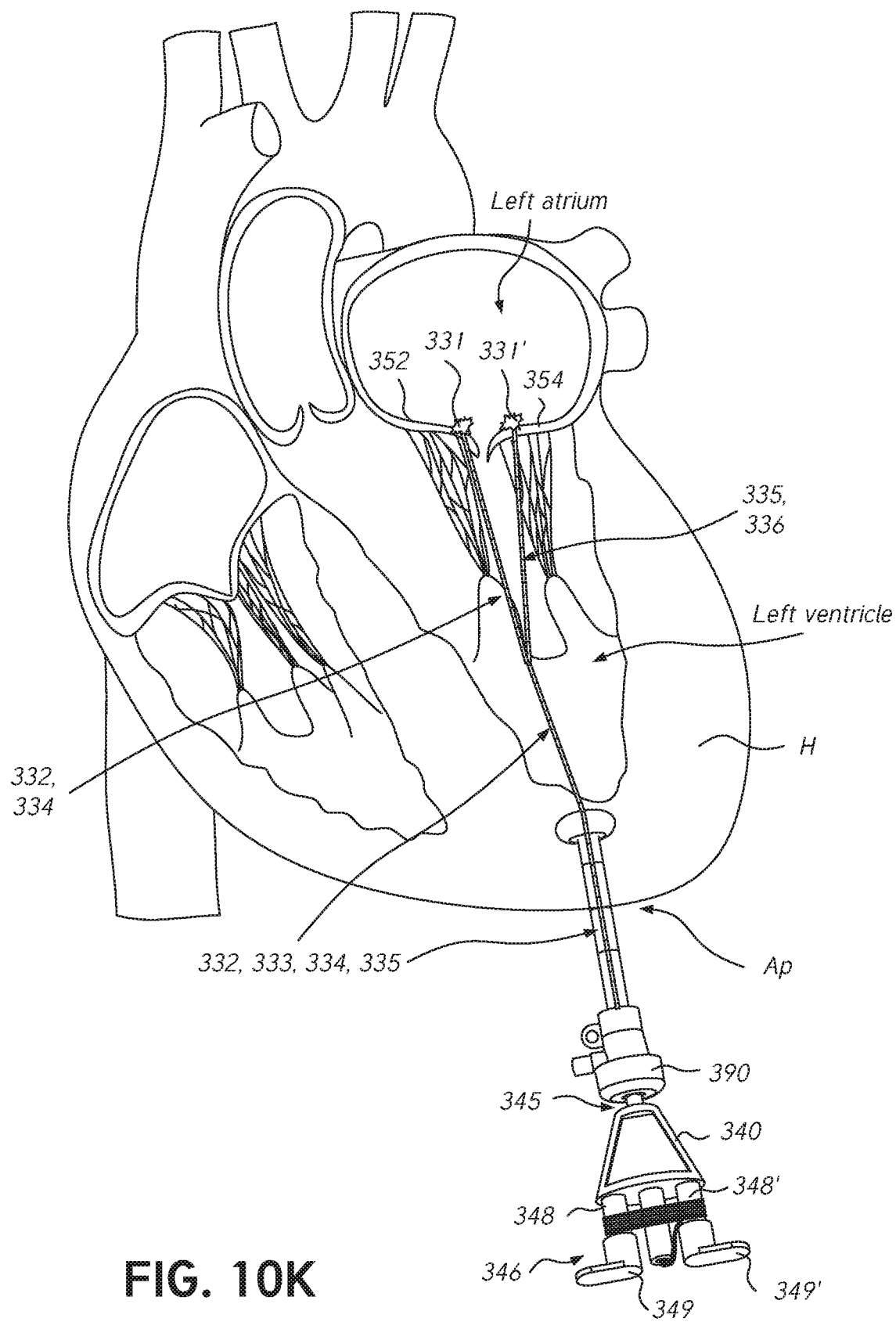

With the suture end portions 332, 333, 334, 335 fixedly coupled to the twister device 340, the twister device 340 is rotated to twist, intertwine, and/or interlace a portion of the suture end portions 332, 333, 334, 335 within the model heart H to approximate the implants 331, 331' and the valve leaflets 352, 354 to which the implants 331, 331' are anchored, as illustrated in FIG. 10G with respect to the model heart H, and as further illustrated in FIG. 10K with respect to a cross-section of a representation of a human heart.

Controlling the number of turns or twists of the twister device 340 allows the user to precisely approximate the valve leaflets 352, 354. Control of the approximation can be aided using, for example, echo guidance, which can be used to determine in real time with a beating heart a targeted reduction or elimination of mitral valve regurgitation. Once the desired result (e.g., a suitable reduction in mitral valve regurgitation) is achieved (e.g., confirmed by remote visualization), the suture end portions 332, 333, 334, 335 can be released from the tie knobs 348, 348' of the twister device 340. Then the twister device 340 can be removed by slidably withdrawing it along the suture end portions 332, 333, 334, 335 to leave the suture end portions 332, 333, 334, 335 extending proximally from the valved-introducer 390, as illustrated in FIG. 10H. With the twister device 340 removed from the valved-introducer 390, a first clamp 394 is used to clamp the suture end portions 332, 333, 334, 335 such that slidable movement of the suture end portions 332, 333, 334, 335 relative to the valved-introducer 390 is limited and/or prevented, as illustrated in FIG. 10H. With the first clamp 394 engaged with the suture end portions 332, 333, 334, 335, the suture end portions 332, 333, 334, 335 can be selectively tensioned (e.g., pulled proximally while monitoring the valve leaflets 353, 354 and any associated regurgitation). After confirming the desirable or targeted tension, a second clamp 392 can then be used to clamp the suture end portions 332, 333, 334, 335, the first clamp 394 can be removed, and knots can be tied using the suture end portions 332, 333, 334, 335 to prevent the twisted sutures from unraveling, as illustrated in FIGS. 10I and 10J. With one or two knots in place to prevent the rotations from untwisting, the second clamp 392 can be removed and the valved-introducer 390 can be removed. The suture end portions 332, 333, 334, 335 can then be anchored outside the apex of the ventricle using the knots, a pledget, or any other suitable anchoring mechanism. In some instances, for example, 16 knots (or 8 square knots) can be used to prevent such undesirable unraveling.

Although in this embodiment the method includes withdrawing the twister device 340 from the valved-introducer 390, and clamping the suture end portions 332, 333, 334, 335 at the proximal end of the valved-introducer 390, in some implementations, once suitable reduction in mitral valve regurgitation is achieved (e.g., confirmed by remote visualization such as echo guidance) and the suture end portions 332, 333, 334, 335 are released from the tie knobs 348, 348' of the twister device 340, both the twister device 340 and the valved-introducer 390 can be slidably withdrawn proximally along the suture end portions 332, 333, 334, 335. In such implementations, the first clamp 394 can be used to clamp the suture end portions 332, 333, 334, 335 near the heart (e.g., between the ventricle and the distal end of the valved-introducer 390).

Figure 11A:
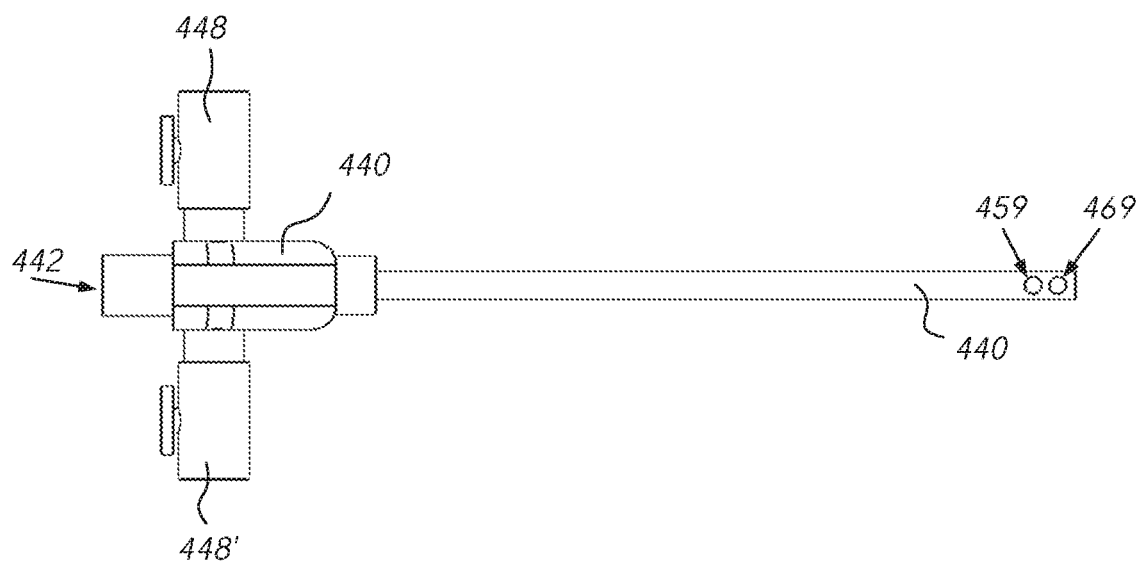
Figure 11B:
Figure 11C:
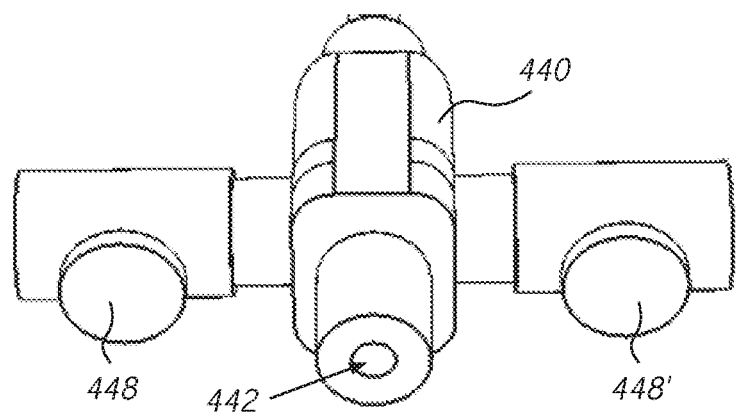
Figure 11D:
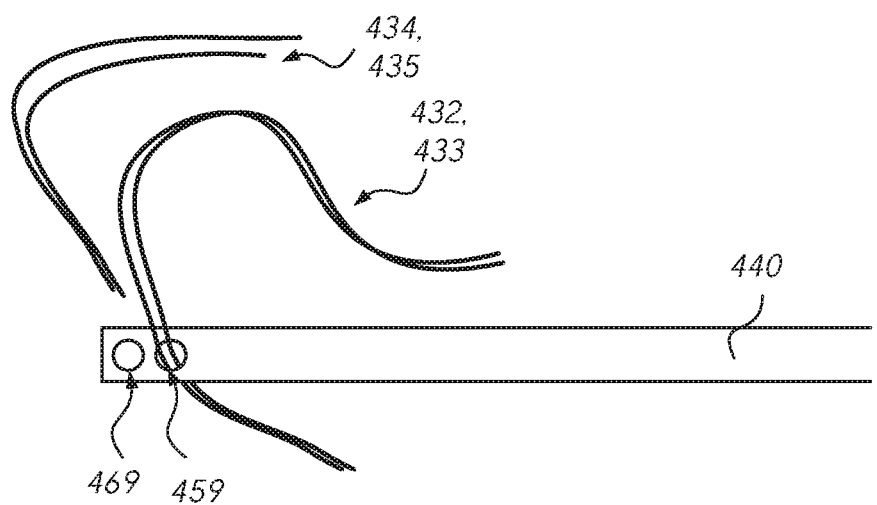
Figure 11E:
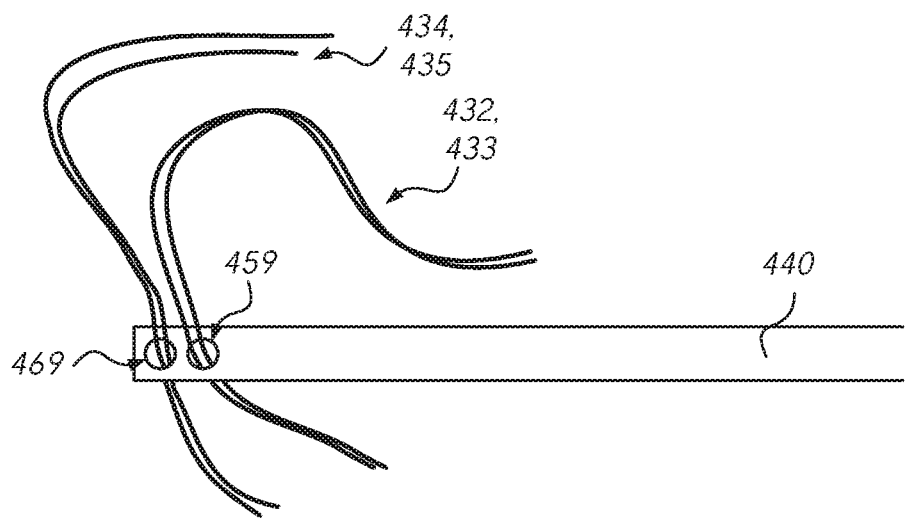
Figure 11F:
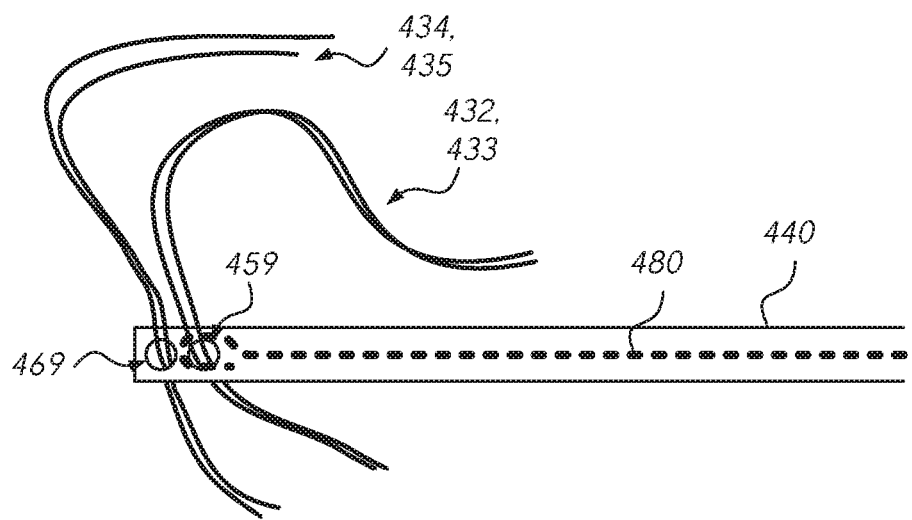
Figure 11G:
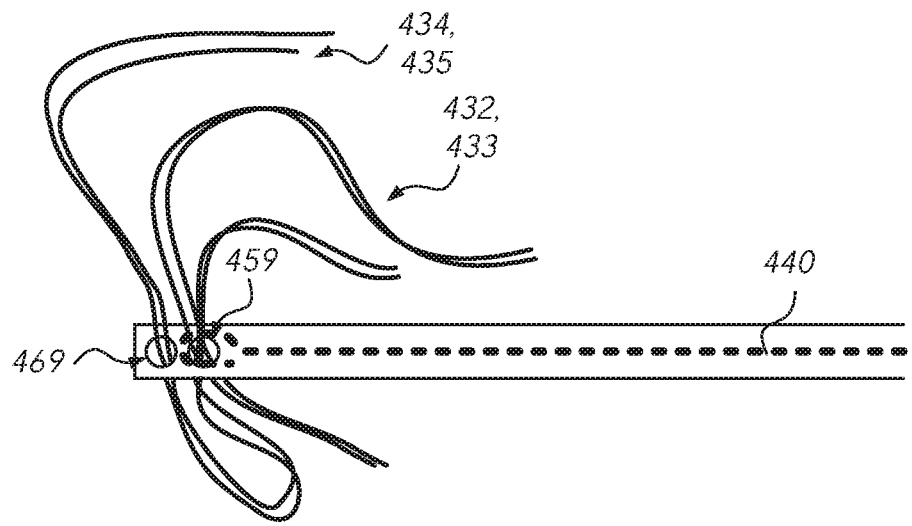
Figure 11N:
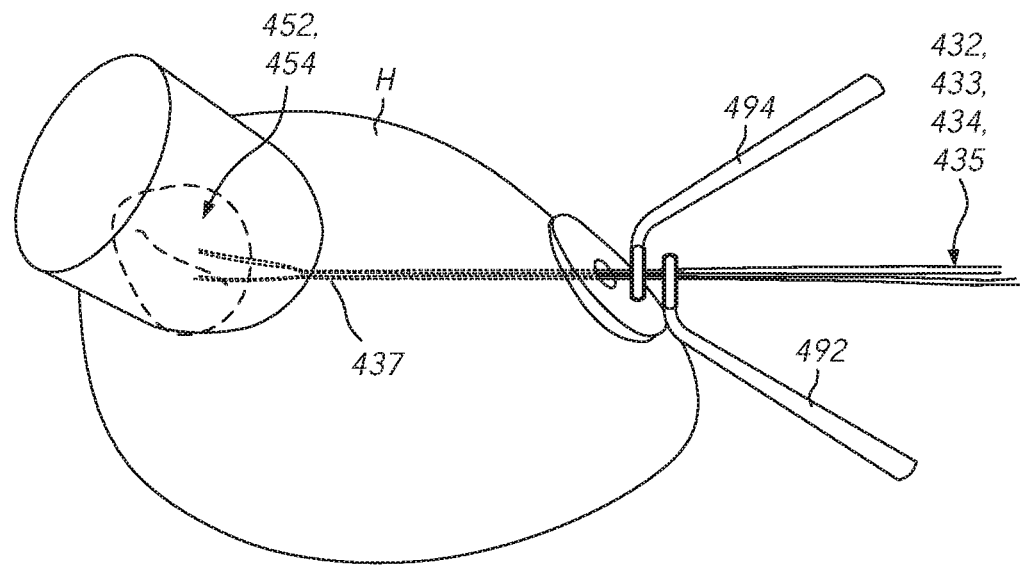
Figure 11O:
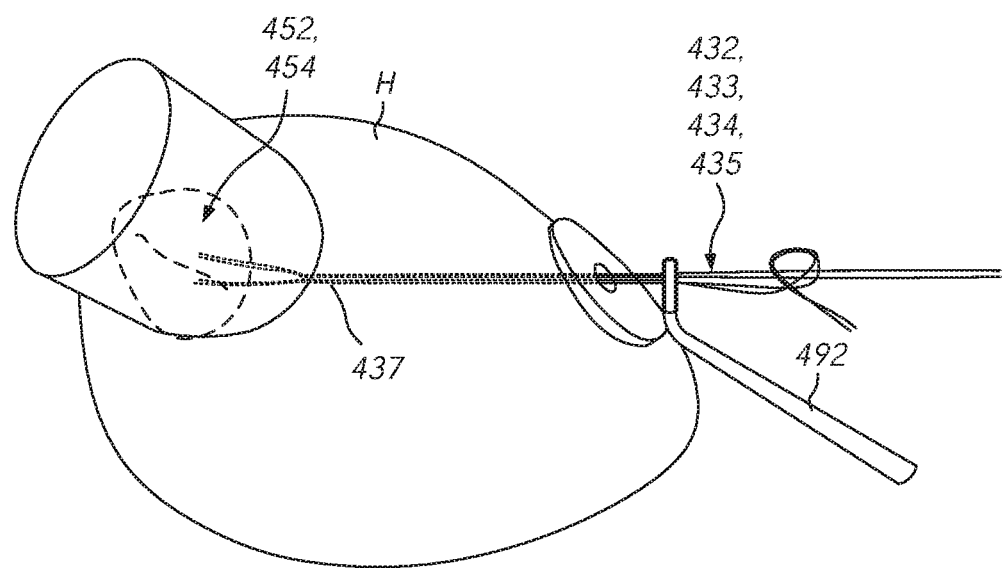

FIGS. 11A-11O illustrate an example method and an example device for securing an artificial tendineae that has been implanted as described in the '761 PCT Application and/or the '170 PCT Application. Similar to previous embodiments described herein, two implants can be delivered and disposed on an atrial, distal, or top side of leaflets 452, 454, respectively. The implants can be formed with a suture material that forms a loop on the atrial side of the leaflets 452, 454 and extends through the leaflets 452, 454, with two loose suture end portions that extend on the ventricular, proximal, or bottom side of the leaflets 452, 454. A first implant has suture end portions 432 and 433, and a second implant has suture end portions 434 and 435. In some embodiments, implants can be formed separate from the suture end portions and then attached thereto. In this manner, the implants can be attached to the suture material, deployed on the atrial side of the leaflets, and the suture end portions can extend from the implants and through the leaflets to the ventricular side of the leaflets, and then anchored outside the heart H as described in further detail herein.

After the implants are in a desired or targeted position (which can be confirmed using imaging, for example), a twister device 440 as illustrated in FIG. 11A can be used during a procedure to secure the implants in the desired or targeted position and to secure the valve leaflets 452, 454 in an edge-to-edge relationship. Further, in addition to or instead of creating the edge-to-edge relationship, to promote a larger surface of coaptation, using the twister device 440, the implants can be secured together to pull or otherwise move the posterior annulus towards the anterior leaflet and/or the anterior annulus towards to posterior leaflet, thereby reducing the distance between the anterior annulus and the posterior annulus, e.g., the septal-lateral distance, by about 10%-40%. Approximating the anterior annulus and the posterior annulus in this manner can decrease the valve orifice, and thereby decrease, limit, or otherwise prevent undesirable regurgitation.

The twister device 440 defines a lumen 442 from its distal end 445 to its proximal end 446, and includes tie knobs 448, 448' (illustrated in the partial detailed view of FIG. 11C) disposed at the proximal end 446. The twister device 440 further includes a valve (e.g., a duckbill valve) configured to limit and/or prevent undesirably backflow of blood or other bodily fluids. In some instances, the twister device 440 can further include an access port configured to receive, for example, a heparinized saline to limit and/or prevent undesirable clotting during the procedure. As illustrated in the partial detailed view of FIG. 11B, the distal end 445 of the twister device 440 defines a first hole 459 and a second hole 469 both configured to receive the suture end portions 432, 433, 434, 435.

As described in more detail herein, the suture end portions 432, 433, 434, 435 can be passed through the lumen 442 from the distal end 445 to the proximal end 446, and then tied-off, wrapped around, fixed, or otherwise secured to the tie knobs 448, 448'. Similarly stated, the tie knob 448 can be used to hold a suture portion extending from a first implant, and the tie knob 448' can be used to hold a suture portion extending from a second implant. With the suture end portions 432, 433, 434, 435 secured to the respective tie knobs 448, 448', the twister device 440 can be rotated, twisted, or otherwise manipulated to approximate the two implants and in turn the leaflets 452, 454, to secure the leaflets 452, 454 in the edge-to-edge relationship, as described in more detail herein. After the leaflets 452, 454 are secured in an edge-to-edge relationship in a desirable manner, the lengths of the suture end portions 432, 433, 434, 435 can be adjusted until the desired or targeted length is established. The proximal end portions of the suture end portions 432, 433, 434, 435 can then be secured to an outer surface of the heart H at, for example, the apex region, with a proximal anchor.

FIGS. 11D-11O illustrate a method using the twister device 440 to approximate two model valve leaflets 452, 454 disposed within a model heart H. As illustrated in FIG. 11I using the model heart H, a valved-introducer 490 is used to gain access to the model heart H and deliver the implants to the model leaflets 452, 454. With the implants secured to the model leaflets 452, 454, and the suture end portions 432, 433, 434, 435 extending from the implants through the model heart and the valved-introducer 490, extending outside the model heart H, the suture end portions 432, 433, 434, 435 can be operably coupled to the twister device 440.

To operably couple the suture end portions 432, 433, 434, 435 to the twister device 440, a threader or snare 480 can be used to thread the suture end portions 432, 433, 434, 435 through the lumen 442 of the twister device 440. With the suture end portions 432, 433, 434, 435 extending outside the model heart H from the valved-introducer 490, the free ends of the suture end portions 432, 433 are inserted through the first hole 459, as illustrated in FIG. 11D, and the free ends of the suture end portions 434, 435 are inserted through the second hole 469, as illustrated in FIG. 11E. Next, the threader 480 is inserted into the lumen 442 from the proximal end 446 to the distal end 445 such that a loop defined by the threader 480 is lined up with the first hole 459, as illustrated in FIG. 11F. With the threader 480 lined up in this manner, the free ends of the suture end portions 432, 433, 434, 435 are inserted through the first hole 459 and through the loop of the threader 480, as illustrated in FIG. 11G. Next, the threader 480 is withdrawn proximally towards the proximal end 446 of the twister device 440, pulling the suture end portions 432, 433, 434, 435 therewith until the free ends of the suture end portions 432, 433, 434, 435 extend through and out of the lumen 442 at the proximal end 446 of the twister device 440, as illustrated in FIG. 11H. In this manner, the operator can selectively control twisting of the suture end portions 432, 433, 434, 435 while limiting and/or preventing the suture end portions 432, 433, 434, 435 from bunching up, e.g., in the valved-introducer 490.

With the suture end portions 432, 433, 434, 435 threaded through the twister device 440 in this manner, the distal end 445 of the twister device 440 can be inserted into the valved-introducer 490, and positioned exactly where the operator wants the twisting to start. Then the suture end portions 432, 433, 434, 435 can then be secured to the twister device 440 by, for example, wrapping the suture end portions 432, 433, 434, 435 around the tie knobs 448, 448', as shown in FIG. 11I. With the suture end portions 432, 433, 434, 435 fixedly coupled to the twister device 440, and the distal end 444 of the twister device 440 inserted through the valved-introducer 490 and into the ventricle of the model heart H, the twister device 440 is rotated to twist, intertwine, and/or interlace a portion of the suture end portions 432, 433, 434, 435 within the model heart H to approximate the implants and the valve leaflets 452, 454 to which the implants are anchored, as illustrated in FIGS. 11J and 11K.

In some instances, with the suture end portions 432, 433, 434, 435 fixedly coupled to the twister device 440, the operator can rotate the twister device 440 to twist, intertwine, and/or interlace a portion of the suture end portions 432, 433, 434, 435. The suture end portions 432, 433, 434, 435 can then be released from the twister device 440 (e.g., released from the tie knobs 448, 448'), and the twister device 440 can be slid or otherwise moved proximally along or about the suture end portions 432, 433, 434, 435. The suture end portions 432, 433, 434, 435 can then be secured again to the twister device 440 which can be further rotated to further twist, intertwine, and/or interlace a portion of the suture end portions 432, 433, 434, 435. This process can be repeated any suitable number of times, e.g., until the twister device 440 has been withdrawn completely from the valved-introducer 490, leaving a sufficient interlaced portion of the suture end portions 432, 433, 434, 435. FIG. 11J illustrates the twisted portion 437 of the suture end portions 432, 433, 434, 435 within the model heart H, and FIG. 11K illustrates the valve leaflets 452, 454 in the approximated position.

Controlling the number of turns or twists of the twister device 440 allows the user to precisely approximate the valve leaflets 452, 454. Control of the approximation can be aided using, for example, echo guidance, which can be used to determine in real time with a beating heart a targeted reduction or elimination of mitral valve regurgitation. Once the desired or targeted result (e.g., a suitable reduction in mitral valve regurgitation) is achieved (e.g., confirmed by remote visualization), the suture end portions 432, 433, 434, 435 can be released from the tie knobs 448, 448' of the twister device 440. Then the twister device 440 and the valved-introducer 490 can be slidably withdrawn along the suture end portions 432, 433, 434, 435. Once a portion of the suture end portions 432, 433, 444, 445 disposed between the outer surface of the heart and the distal end of one or both of the valved-introducer 490 and/or the twister device 440 are exposed to the operator, as illustrated in FIG. 11L, a first clamp 494 can be used to clamp the suture end portions 432, 433, 434, 435 such that both slidable movement of the suture end portions 432, 433, 434, 435 relative to the valved-introducer 490 and unwinding of the interlaced portion is limited and/or prevented, as illustrated in FIG. 11M.

With the first clamp 494 engaged with the suture end portions 432, 433, 434, 435, the suture end portions 432, 433, 434, 435 can be selectively tensioned (e.g., pulled proximally while monitoring the valve leaflets 452, 454 and any associated regurgitation). After confirming the desirable tension, a second clamp 492 can then be used to clamp the suture end portions 432, 433, 434, 435 near or adjacent to the outside surface of the heart, as illustrated in FIG. 11N, the first clamp 494 can be removed, and knots can be tied using the suture end portions 432, 433, 434, 435 to prevent the twisted sutures from unraveling, as illustrated in FIG. 11O. In some instances, for example, 16 knots (or 8 square knots) can be used to prevent such undesirable unraveling. The suture end portions 432, 433, 434, 435 can then be anchored outside the apex of the ventricle using the knots, a pledget, or any other suitable anchoring mechanism.

While in various embodiments described herein, methods have included removing a twister device from the cords or sutures after the cords were interlaced, it should be understood that for any of these embodiments, the process of interlacing the cords is adjustable (including reversible) in real-time. In this manner, if an operator applies too many twists (e.g., identified as such under remote visualization), the operator can simply rotate or twist the twister device in an opposite direction to partially or fully unlace or unravel the cords. The operator could then optionally begin interlacing the cords again until the suitable number of twists is achieved.

Figure 12A:
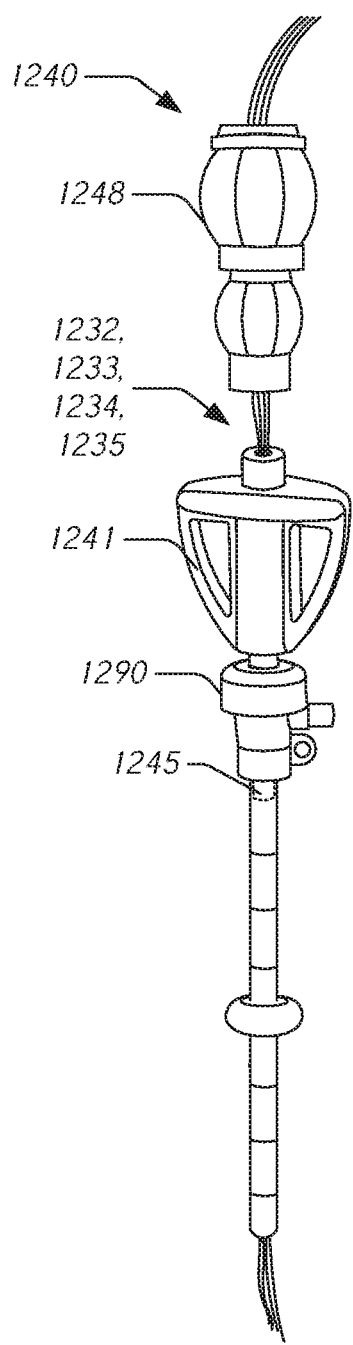
FIGS. 12A and 12B illustrate another example twister device with a rotating spin lock.
Figure 12B:
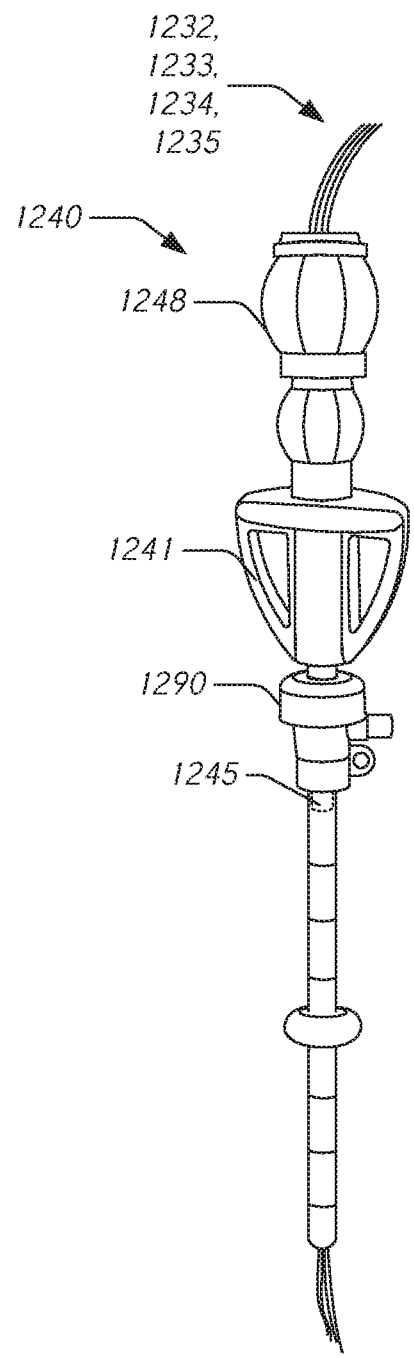

FIGS. 12A and 12B illustrate another example twister device 1240 with a rotating spin lock 1248. The rotating spin lock 1248 can be used to secure suture end portions 1232, 1233, 1234, 1235 to the twister device 1240 so that upon rotation of the twisting component 1241, the sutures intertwine. The rotating spin lock 1248 can be beneficial for hemostasis and suture management. The rotating spin lock 1248 is an adjustable leak proof seal configured to grip the suture end portions 1232, 1233, 1234, 1235 and to prevent backflow of blood during the procedure.

The rotating spin lock 1248 allows for unimpeded threading of the suture end portions 1232, 1233, 1234, 1235 in an open position. Once the suture end portions 1232, 1233, 1234, 1235 are pulled through, the rotating spin lock 1248 is partially closed to reduce the gap sufficient for the suture end portions 1232, 1233, 1234, 1235 to be adjusted and pulled through simultaneously as the tubular end 1245 of the twister device 1240 is inserted into the introducer 1290. This can result in minimal blood reflux.

Once the twister device 1240 is fully inserted in the valve introducer 1290, the rotating spin lock 1248 is rotated to a fully closed position. The rotating spin lock 1248 includes a valve that clamps down on the suture end portions 1232, 1233, 1234, 1235 with a firm grip to prevent the suture end portions 1232, 1233, 1234, 1235 from slipping and tangling as the twisting component 1241 is rotated. In some embodiments, a side port can be added to the rotating spin lock 1248 to allow for continuous pressurized flow of heparinized saline to reduce or to prevent blood from clotting and to reduce or prevent aspiration of air into the system.

Repairing a cardiac valve (e.g., a mitral valve) by implanting a distal anchor or implant, as described herein, is often influenced by a patient's particular anatomy. When the combined length of the posterior leaflet and the anterior leaflet is significantly larger than the A-P dimension of the mitral valve, the likelihood of a successful repair is significantly higher. For example, a patient having a large posterior leaflet is desirable, as a large posterior leaflet provides a large surface of coaptation with the anterior leaflet, thereby providing a sufficient seal when the leaflets coapt, e.g., to limit regurgitation. Conversely, a patient having a small posterior leaflet will have a relatively smaller surface of coaptation. Similarly, a patient having a large anterior leaflet can help lead to a desirable and successful repair. Ultimately, the effectiveness and durability of a repair of this nature is influenced greatly by the amount of anterior and posterior leaflet tissue coapting together during systole. As another example, some patients have a relatively large valve orifice (e.g., the orifice may dilate over time due to illness), and as a result are prone to less leaflet coaptation and increased regurgitation. Ensuring sufficient coaptation is addressed by various embodiments described herein, including the following examples.

While various embodiments described above include interlacing cords extending from implants deployed near the free edge of mitral valve leaflets to perform an edge-to-edge or Alfieri procedure, in some implementations, the implants can be alternatively or additionally deployed in other locations to facilitate other types of cardiac repairs necessitated by various cardiac issues (e.g., small posterior leaflet, large orifice, leaflet clefts, etc.), some of which are described below.

In some embodiments, for example, the implants can be placed near the free edge of the anterior and posterior leaflets, and the cords extending therefrom can be interlaced using the methods and devices described above to improve coaptation of the anterior and posterior leaflets. For example, in a patient who has a relatively large valve orifice (e.g., due to dilation of the orifice over time due to illness), and as a result is prone to less leaflet coaptation and increased regurgitation, approximating the implants can increase available leaflet surfaces for coaptation. Additionally, the interlaced cord can be suitably tensioned and/or pulled towards the access site and into the ventricle of the heart, resulting in a larger surface area of coaptation, and improved coaptation between the leaflets.

Further, to promote a larger surface of coaptation, in some embodiments, implants can be deployed in the body of the leaflets and/or at or near the annulus of the anterior and posterior leaflets, and the cords extending therefrom can be interlaced to pull or otherwise move the posterior annulus towards the anterior leaflet and/or the anterior annulus towards the posterior leaflet, thereby reducing the distance between the anterior annulus and the posterior annulus, e.g., the septal-lateral distance, by about 10%-40%. Said another way, approximating the anterior annulus and the poster annulus in this manner can decrease the valve orifice, and thereby decrease, limit, or otherwise prevent undesirable regurgitation.

While various embodiments described herein have included two implants and two sets of cords, in various implementations, any suitable number of implants and any suitable number of sets of cords can be delivered, deployed, and interlaced to approximate various portions of the heart to combat the cardiac issues described herein. For example, in some embodiments, three or more sets of cords can be twisted or interlaced to approximate three or more implants.

In some instances, for example, the heart can be effectively re-shaped (e.g., improve orifice geometry, improve relative leaflet geometry, etc.) by strategically deploying multiple implants and securing multiple cords extending therefrom using the methods and devices described herein.

As another example, in some instances, it may be desirable to decrease a gap between a valve commissure (e.g., the edge of the valve where the leaflets come together). In such instances, a first implant can be deployed on the posterior leaflet near the commissure and a second implant can be deployed on the anterior leaflet near the commissure. With both the first implant and second implant deployed in this manner, the cords extending therefrom can be interlaced to approximate the first implant and the second implant such that the gap between the commissure is limited, decreased, or eliminated.

As another example, in some instances in which a patient has a clefted leaflet, two or more implants can be deployed on either side of the cleft. The cords extending therefrom can then be interlaced to approximate the implants such that the cleft in the leaflet is limited, decreased, or eliminated.

Figure 13:
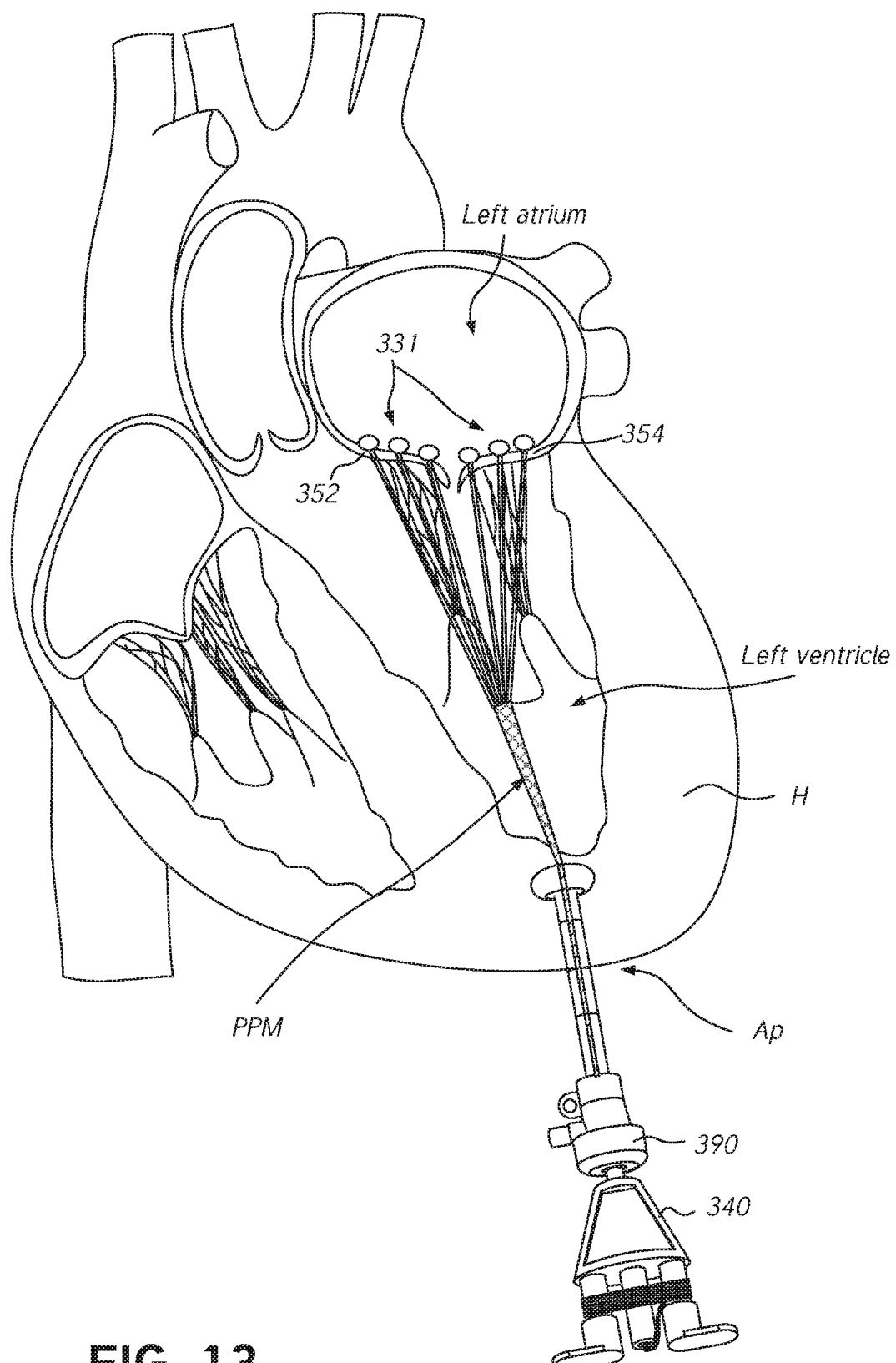
FIG. 13 illustrates a cross-sectional view of a heart having implant and interlaced chords deployed therein and coupled to the example twister device of FIGS. 11A-11O.

As another example, the valve annulus and/or orifice can be optimized and/or reduced in size by deploying multiple anchors and cords extending therefrom in various locations within the heart to effectively deliver the equivalent of an additional papillary muscle or a prosthetic papillary muscle (PPM). Such an embodiment is illustrated in FIG. 13 using, as an example, the twister device 340 described above with respect to FIGS. 10A-10J. As shown, six implants 331 are deployed to the mitral valve, and all the cords extending from the six implants 331 are interlaced to effectively create a single anchor common to all of the cords. Deploying multiple implants and securing or approximating the cords in this manner can provide the functionality otherwise provided by a properly functioning papillary muscle.

In some embodiments, a plurality of cords with implants at distal ends thereof can be attached to the posterior leaflet. In such embodiments, one or more of the sutures extending from the implants can be twisted, intertwined, or interlaced using the methods and devices described herein. Similarly, in such embodiments, any portion of the sutures extending from implants in the posterior leaflet can be twisted, intertwined, or interlaced using the methods and devices described herein, wherein the portion can be more than one suture, less than all of the sutures, or all of the sutures. A plurality of chords can be attached to the posterior leaflet to reduce cord failures by creating a thicker, stronger base.

In some embodiments, a plurality of cords with implants at distal ends thereof can be attached to the anterior leaflet. In such embodiments, one or more of the sutures extending from the implants can be twisted, intertwined, or interlaced using the methods and devices described herein. Similarly, in such embodiments, any portion of the sutures extending from implants in the anterior leaflet can be twisted, intertwined, or interlaced using the methods and devices described herein, wherein the portion can be more than one suture, less than all of the sutures, or all of the sutures. A plurality of chords can be attached to the anterior leaflet to reduce cord failures by creating a thicker, stronger base.

In some embodiments, a plurality of cords with implants at distal ends thereof can be attached to both the anterior leaflet and the posterior leaflet. In such embodiments, one or more of the sutures extending from the implants can be twisted, intertwined, or interlaced using the methods and devices described herein. Similarly, in such embodiments, any portion of the sutures extending from implants in the anterior leaflet and the posterior leaflet can be twisted, intertwined, or interlaced using the methods and devices described herein, wherein the portion can be more than one suture, less than all of the sutures, or all of the sutures.

The above-described procedures can be performed manually, e.g., by a physician, or can alternatively be performed fully or in part with robotic or machine assistance. For example, in some embodiments, a twister device can be configured to twist automatically to provide the desirable amount of interlacing. Further, although not specifically described for some embodiments, in various embodiments, the heart may receive rapid pacing to minimize the relative motion of the edges of the valve leaflets during the procedures described herein (e.g., while the sutures are being interlaced).

Additional Embodiments and Terminology

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components and/or features of the different embodiments described.

The present disclosure describes various features, no single one of which is solely responsible for the benefits described herein. It will be understood that various features described herein may be combined, modified, or omitted, as would be apparent to one of ordinary skill. Other combinations and sub-combinations than those specifically described herein will be apparent to one of ordinary skill, and are intended to form a part of this disclosure. Various methods are described herein in connection with various flowchart steps and/or phases. It will be understood that in many cases, certain steps and/or phases may be combined together such that multiple steps and/or phases shown in the flowcharts can be performed as a single step and/or phase. Also, certain steps and/or phases can be broken into additional sub-components to be performed separately. In some instances, the order of the steps and/or phases can be rearranged and certain steps and/or phases may be omitted entirely. Also, the methods described herein are to be understood to be open-ended, such that additional steps and/or phases to those shown and described herein can also be performed.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." The word "coupled", as generally used herein, refers to two or more elements that may be either directly connected, or connected by way of one or more intermediate elements. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or" in reference to a list of two or more items, that word covers all of the following interpretations of the word: any of the items in the list, all of the items in the list, and any combination of the items in the list.

The disclosure is not intended to be limited to the implementations shown herein. Various modifications to the implementations described in this disclosure may be readily apparent to those skilled in the art, and the generic principles defined herein may be applied to other implementations without departing from the spirit or scope of this disclosure. The teachings of the invention provided herein can be applied to other methods and systems, and are not limited to the methods and systems described above, and elements and acts of the various embodiments described above can be combined to provide further embodiments. Accordingly, the novel methods and systems described herein may be embodied in a variety of other forms; furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure.

What is claimed is:

1. A method for twisting sutures together to approximate anchor implants attached to targeted tissue, the method comprising:
    attaching two or more cords to targeted tissue, each of the two or more cords including a distal anchor implant and a suture extending proximally from the distal anchor implant;
    securing proximal end portions of the sutures of the two or more cords to a twister device;
    operating the twister device to cause the sutures of the two or more cords to intertwine;
    releasing the proximal end portions of the sutures of the two or more cords from the twister device; and
    anchoring the proximal end portions of the sutures of the two or more cords to prevent unwinding of the sutures of the two or more cords.

2. The method of claim 1, wherein the targeted tissue is within the heart and the twister device is positioned outside of the heart so that it is operated outside of the heart.

3. The method of claim 2, wherein anchoring the proximal end portions of the sutures of the two or more cords includes securing the proximal end portions to an external wall of the heart.

4. The method of claim 2 further comprising inserting a portion of the twister device into a valve introducer that provides access to the targeted tissue within the heart.

5. The method of claim 1, wherein the targeted tissue includes a leaflet of a mitral valve.

6. The method of claim 5, wherein the targeted tissue includes a posterior leaflet.

7. The method of claim 5, wherein the targeted tissue includes an anterior leaflet.

8. The method of claim 1 further comprising adjusting a tension of the sutures of the two or more cords.

9. The method of claim 8, wherein adjusting a tension of the sutures of the two or more cords occurs simultaneously with operating the twister device to cause the sutures of the two or more cords to intertwine.

10. The method of claim 1, wherein operating the twister device to cause the sutures of the two or more cords to intertwine results in a point of intersection that approaches the targeted tissue to change a force vector on the two or more cords attached to the targeted tissue.

11. The method of claim 1, wherein the distal anchors of the two or more cords are secured to tissue within a heart and the proximal end portions of the sutures of the two or more cords are anchored to an external wall of the heart.

12. The method of claim 11, wherein a portion of the twister device to which the proximal end portions of the sutures of the two or more cords are secured is located outside of the heart.

13. The method of claim 1, wherein the targeted tissue is within a heart so that the distal anchor implants of the two or more cords are attached to the targeted tissue within the heart and the proximal end portions of the sutures extend outside of the heart.

14. The method of claim 1, wherein operating the twister device to cause the sutures of the two or more cords to intertwine improves coaptation of a mitral valve.

15. The method of claim 1, wherein attaching two or more cords to targeted tissue includes deploying each of the distal anchor implants of the two or more cords on a distal side of the targeted tissue with each of the sutures of the two or more cords passing through the targeted tissue to extend proximally from the targeted tissue.

16. The method of claim 1, wherein anchoring includes tying one or more knots in the proximal end portions of the two or more cords to secure the proximal end portions to anchor tissue.

17. The method of claim 1, wherein anchoring includes securing the proximal end portions of the two or more cords to maintain an axial force on each of the sutures of the two or more cords.

18. The method of claim 17, wherein the axial force is directed proximally from the distal anchor implants of the two or more cords.

19. The method of claim 17, wherein the axial force pulls the distal anchor implants of the two or more cords proximally and toward each other.

* * * * *